(12) United States Patent
Fan et al.

(10) Patent No.: US 11,286,247 B2
(45) Date of Patent: Mar. 29, 2022

(54) ACRYLOYL-CONTAINING NUCLEAR TRANSPORT REGULATORS AND USES THEREOF

(71) Applicant: WIGEN BIOMEDICINE TECHNOLOGY (SHANGHAI) CO., LTD., Shanghai (CN)

(72) Inventors: Houxing Fan, Shanghai (CN); Yuli Xie, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/071,949

(22) Filed: Oct. 15, 2020

(65) Prior Publication Data
US 2021/0053945 A1    Feb. 25, 2021

Related U.S. Application Data

(63) Continuation of application No. PCT/CN2020/076525, filed on Feb. 25, 2020.

(30) Foreign Application Priority Data

Feb. 26, 2019 (CN) .......................... 201910144005.4

(51) Int. Cl.
| | | |
|---|---|---|
| C07D 403/12 | (2006.01) | |
| C07D 491/00 | (2006.01) | |
| C07D 471/10 | (2006.01) | |
| C07D 471/08 | (2006.01) | |
| C07D 471/04 | (2006.01) | |
| C07D 413/12 | (2006.01) | |
| C07D 487/04 | (2006.01) | |
| A61P 35/04 | (2006.01) | |
| C07D 403/14 | (2006.01) | |
| C07D 487/10 | (2006.01) | |
| C07D 491/107 | (2006.01) | |
| A61K 9/00 | (2006.01) | |

(52) U.S. Cl.
CPC ............ *C07D 403/12* (2013.01); *A61P 35/04* (2018.01); *C07D 403/14* (2013.01); *C07D 413/12* (2013.01); *C07D 471/04* (2013.01); *C07D 471/08* (2013.01); *C07D 471/10* (2013.01); *C07D 487/04* (2013.01); *C07D 487/10* (2013.01); *C07D 491/107* (2013.01); *A61K 9/0053* (2013.01); *C07B 2200/07* (2013.01); *C07B 2200/13* (2013.01)

(58) Field of Classification Search
CPC combination set(s) only.
See application file for complete search history.

(56) References Cited

FOREIGN PATENT DOCUMENTS

| CN | 103842340 A | 6/2014 |
|---|---|---|
| CN | 103874690 A | 6/2014 |
| CN | 105339358 A | 2/2016 |
| WO | 2014144772 A1 | 9/2014 |
| WO | 2014205393 A1 | 12/2014 |

*Primary Examiner* — Samira J Jean-Louis
(74) *Attorney, Agent, or Firm* — SZDC Law P.C.

(57) ABSTRACT

The invention relates to a series of novel compounds containing acryloyl group. In particular, the invention relates to acryloyl group-containing compounds shown in formula (1) and the preparation method thereof, and application of the compounds shown in formula (1) and pharmaceutically acceptable salts thereof in preparation of medicaments for treating, regulating and/or preventing diseases related to physiological conditions related to CRM1 protein.

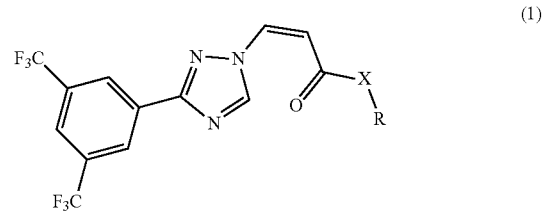

(1)

11 Claims, 1 Drawing Sheet

ACRYLOYL-CONTAINING NUCLEAR TRANSPORT REGULATORS AND USES THEREOF

RELATED APPLICATION

This application is a Continuation Application of PCT/CN2020/076525, filed on Feb. 25, 2020, which claims the benefits of Chinese Patent Application No. 2019101440054, filed on Feb. 26, 2019, which is incorporated herein by reference in its entirety.

FIELD OF THE INVENTION

The invention belongs to the fields of pharmaceuticals, medicinal chemistry and pharmacology, and more specifically, relates to a kind of acryl-containing CRM1 protein regulators, the preparation methods and the uses thereof.

BACKGROUND OF THE INVENTION

Appropriate cellular location is essential for proper protein functions. Among which, the entry and exit of proteins from the nucleus is crucial for maintaining homeostasis within cells. Traffic between cytosol and nucleus relies on specific transport proteins including importins and exportins that transport cargos into and out of the nucleus respectively. Exportin 1 also known as CRM1 or XPO1 mediates the nuclear export of over 200 proteins, the majority of which are tumor suppressors and regulators of cell cycle and apoptosis, such as p53, p21, Rb1, APC, BCR-ABL, FOXO, cyclin B1 and survinvin1. In normal cells, regulated nuclear export of these proteins controls their activation or inactivation. Whereas, in tumor cells, excessive export of these proteins promotes oncogenic transformation. [Current Medicinal Chemistry, 2008, 15(26): 2648-2655].

CRM1 is overexpressed in a plethora of tumor types including breast cancer [Cancer, 2008, 112(8): 1733-1743], cervical cancer [International Journal of Cancer, 2009, 124 (8): 1829-1840], gastric cancer[Medical Oncology, 2013, 30(4): 726], osteoarcoma [Oncology Reports, 2009, 21(1): 229-235], glioblastoma [Neurosurgery, 2009, 65(1): 153-160], lung cancer [British Journal of Cancer (2014) 111, 281-291], pancreatic cancer [Gastroenterology, 2013, 144 (2): 447-456], liver cancer [Cancer Chemother Pharmacol, 2014, 74(3): 487-495], renal cancer[Journal of Urology, 2013, 189(6): 2317-2326], esophagus cancer [Oncology Report, 2014, 32(2): 730-738], lymphoma [Blood, 2012, 120(23): 4621-4634], multiple myeloma [Leukemia, 2014, 28(1):155-165] and leukemia [Blood, 2013, 121(20): 41664174], and high expression of CRM1 correlates with poor prognosis. CRM1 overexpression results in the transport of tumor suppressors to the cytosol, leading to their degradation and consequent inactivation, and this is regarded to be one of the mechanisms, by which tumor cells evade apoptosis [Biochemical Pharmacology, 2012, 83(8): 1021-1032; Seminars in Cancer Biology, 2014, 27:74-86]. In addition, mutations in KRAS render lung cancer cells more vulnerable to CRM1 inhibitors including KPT-185 和 KPT-330, whereas, lung cancer cells without KRAS mutations are more resistant. Comparative gene set analysis reveals NF-κB activation may underlie the increased sensitivity of KRAS mutant lung cancer to CRM1 inhibition [Nature, 2016, 538:114-117].

In addition to tumor suppressors, CRM1 mediates the nuclear export of many key proteins in inflammation and immunity, including IκB, NF-κB, Cox-2, RXRα, Commd1, HIF1, HMGB1, FOXO and FOXP. IκB is an inhibitor of NF-κB. It binds to and inactivates NF-κB in the nucleus and thereby regulates the activation of the NF-κB pathway, intimately intertwined with inflammation and immunity. CRM1 transports IκB to the cytosol, where it is degraded and cannot inhibit NF-κB [Journal of Biological Chemistry, 1999, 274(13):9108-9115; Shock, 2008, 29(2):160-166]. The essential role of CRM1-mediated nuclear export in the NF-κB, HIF-1 and RXRα signal transduction pathways suggest that blockage of nuclear export might be beneficial for the treatment of a variety of inflammatory diseases, afflicting multiple tissues and organs including vasculitis, arteritis, atherosclerosis, psoriasis, arthritis, lupus, and Scleroderma.

The assembly and maturation of multiple viruses such as human immunodeficiency virus (HIV), influenza virus (HIN1), Hepatitis B virus (HBV), Hepatitis C protein (HCV), Human papilloma (HPV), respiratory syncytial virus (RSV), dengue fever virus (Dungee), severe acute respiratory syndrome coronavirus (SARS), West Nile virus (WNE), herpes simplex virus (HSV) and Merkel Cell polyomavirus (MCV) also require CRM1 [Proceedings of the National Academy of Sciences, 2002, 99(22): 14440-14445; Journal of Virology, 2008, 82(21): 10946-10952; Journal of Biological Chemistry, 2009, 284(23): 15589-15597; Journal of Virology, 2009, 83(11):5353-5362]. Many of these viruses are linked to cancer development. For example, chronic infection of HBV or HCV leads to hepatic cell carcinoma, and HPV infection causes cervical cancer. Thus, inhibition of CRM1 can block virus infection and impede malignant transformation by viruses.

The natural product leptomycin B (LMB) has been widely used as a CRM1 inhibitor in many studies. Although LMB exhibits potent activity towards tumor cells, it is poorly tolerated in animal studies. A Phase I trial of LMB was early terminated due to its overt toxicity [Trends in Cell Biology, 2007, 17(4): 193-201]. Based on the hydrophobic pocket of NES domain of XPO1, a series of compounds were designed by Karyopharm through molecular docking and their antitumor activities were evaluated. Several slowly reversible CRM1 inhibitors with better water solubility and defined configuration emerged including KPT-185, KPT-276, KPT-330 (Selinexor) and KPT-251 [WO2012099807; WO2013019548; WO2013019561; WO2013170068]. Their chemical structures are listed below:

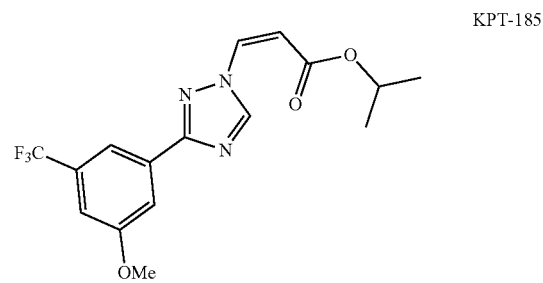

KPT-185

KPT-276

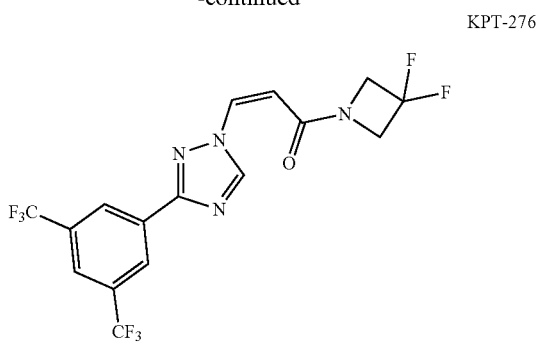

KPT-335

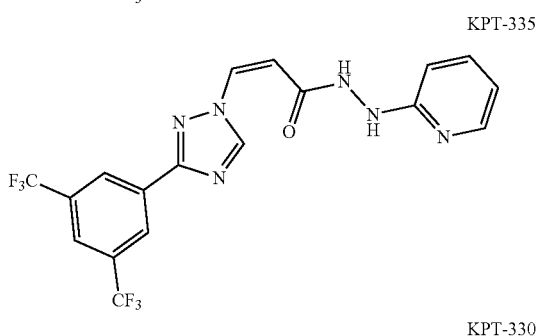

KPT-330

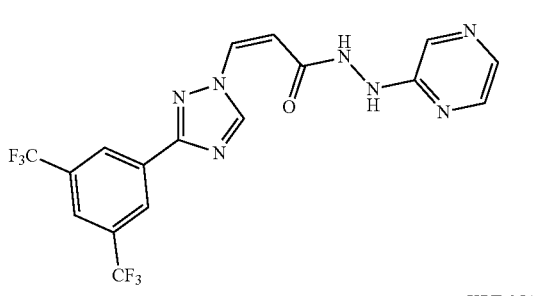

KPT-251

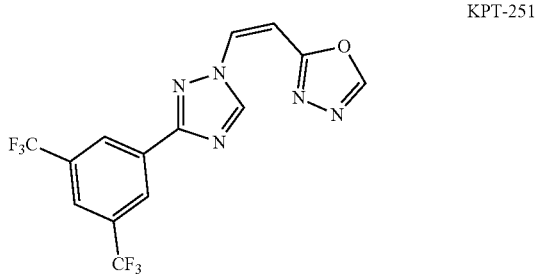

Compared to KPT-276 and KPT-251, KPT-330 showed improved oral bioavailability, and pharmacokinetic, pharmacodynamic and safety profiles. KPT-330 is now under the clinical development for the treatment of acute myeloid (AML), multiple myeloma (MM), diffused large B cell lymphoma (DLBCL), glioblastoma multiforme (GBM), Gynecological cancer, prostate cancer and head and neck squamous cell carcinoma (HNSCC). However, KPT-330 can cross blood brain barrier and is associated with pharmaeoinetic and safety liabilities. The current invention provides a new generation of CRM1 inhibitors with better aqueous solubility, pharmacokinetic properties and safety profiles.

SUMMARY OF THE INVENTION

The present invention provides a compound of general formula (1), an optical isomer, a crystalline form, a pharmaceutically acceptable salt, a hydrate or a solvate thereof:

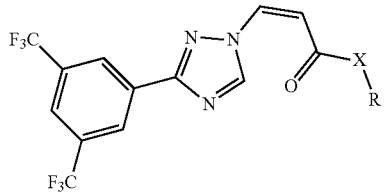

(1)

In formula (1):
X is —NH— or a bond;
when X is —NH—, R is —NR$^1$COR$^2$, wherein R$^1$ and R$^2$ together with an amide group connected thereto form a 4-7 membered saturated, unsaturated or partially saturated heterocycle, the heterocycle is optionally substituted by 1-2 groups selected from the group consisting of halogen, CN, CF$_3$, CH$_2$CF$_3$, CH$_2$CN, OCF$_3$, OCH$_2$CF$_3$, OH, R$^3$, OR$^3$ and NR$^3$R$^{3'}$; wherein R$^3$ and R$^{3'}$ independently selected from the group consisting of H, substituted or unsubstituted C1-C3 alkyl, and substituted or unsubstituted C3-C6 cycloalkyl; or
R$^1$ and R$^2$ together with the amide group connected thereto form a 5-7 membered non-aromatic heterocycle fused with a 5-6 membered aromatic heterocycle, a 5-7 membered non-aromatic heterocycle fused with a 3-6 membered non-aromatic heterocycle, a spiro ring formed by a 5-7 membered non-aromatic heterocycle and a 3-6 membered non-aromatic heterocycle, or a bridged ring formed by a 5-7 membered non-aromatic heterocycle and a 3-6 membered non-aromatic heterocycle; the fused 5-7 membered non-aromatic heterocycle, the fused 5-7 membered non-aromatic heterocycle, the spiro ring, and the bridged ring are optionally substituted by 1-2 groups selected from the group consisting of halogen, CN, CF$_3$, OCF$_3$, OCH$_2$CF$_3$, OH, R$^3$ and OR$^3$; wherein R$^3$ is substituted or unsubstituted C1-C3 alkyl, or substituted or unsubstituted C3-C6 cycloalkyl;
when X is a bond, R is —NR$^4$NR$^5$COR$^6$, wherein R$^5$ is selected from the group consisting of H, substituted or unsubstituted C1-C3 alkyl, substituted or unsubstituted C3-C6 cycloalkyl, alkoxy substituted C1-C3 alkyl, cycloalkyl substituted C1-C3 alkyl, substituted or unsubstituted 5-7 membered heteroaryl, and substituted or unsubstituted 5-7 membered non-aromatic heterocycle; R$^4$ and R$^6$ together with a hydrazide group connected thereto form a 5-7 membered non-aromatic heterocycle, which is optionally substituted by 1-2 groups selected from the group consisting of halogen, CN, OH, R$^3$ or OR$^3$; and R$^3$ is substituted or unsubstituted C1-C3 alkyl, or substituted or unsubstituted C3-C6 cycloalkyl; or
when X is a bond, R is the following group:

wherein, n is 1 or 2:
Y is selected from the group consisting of a bond, —CH$_2$—, —CH$_2$CH$_2$—, —CO—, —SO$_2$—, —SO—, —CON(R$^8$)—, —SO$_2$N(R$^8$)—, and —COCON(R$^8$)—, wherein R$^8$ is H, substitution or unsubstituted C1-C3 alkyl, or substituted or unsubstituted C3-C6 cycloalkyl;

R[7] is selected from the group consisting of H, substituted or unsubstituted C1-C3 alkyl, substituted or unsubstituted C1-C3 alkoxy, substituted or unsubstituted C3-C6 cycloalkyl, substituted or unsubstituted 5-7 membered heteroaryl, and substituted or unsubstituted 5-7 membered non-aromatic heterocycle.

In a preferred embodiment, the compound of general formula (1) is represented by the following formula (1A):

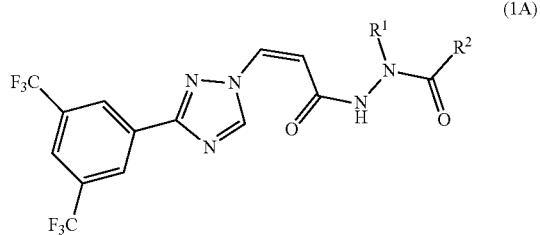

(1A)

or a pharmaceutically acceptable salt thereof, wherein:

R[1] and R[2] together with the amide group connected thereto form a 4-7 membered saturated, unsaturated or partially saturated heterocycle, the heterocycle is optionally substituted by halogen, CN, $CF_3$, $CH_2CF_3$, $CH_2CN$, $OCF_3$, $OCH_2CF_3$, OH, R[3], OR[3] or NR[3]R[3']; wherein R[3] and R[3'] are independently selected from the group consisting of H, substituted or unsubstituted C1-C3 alkyl, and substituted or unsubstituted C3-C6 cycloalkyl; or R[1] and R[2] together with the amide group connected thereto form a 5-7 membered non-aromatic heterocycle fused with a 5-6 membered aromatic heterocycle, a 5-7 membered non-aromatic heterocycle fused with a 3-6 membered non-aromatic heterocycle, a spiro ring formed by a 5-7 membered non-aromatic heterocycle and a 3-6 membered non-aromatic heterocycle, a bridged ring formed by a 5-7 membered non-aromatic heterocycle and a 3-6 membered non-aromatic heterocycle, and the fused 5-7 membered non-aromatic heterocycle, the fused 5-7 membered non-aromatic heterocycle, the spiro ring, and the bridged ring are optionally by 1-2 groups selected from the group consisting of halogen, CN, CF $OCF_3$, $OCH_2CF_3$, OH, R[3] or OR[3]; wherein R[3] is substituted or unsubstituted C1-C3 alkyl, or substituted or unsubstituted C3-C6 cycloalkyl.

In another preferred embodiment, the compound of general formula (1) is represented by the following formula (1B):

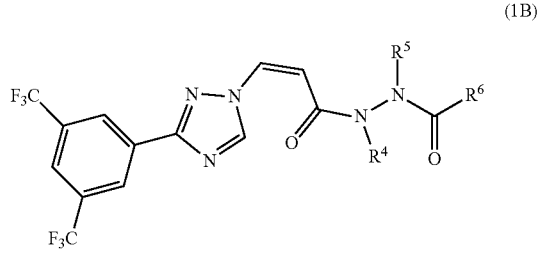

(1B)

or a pharmaceutically acceptable salt thereof, wherein:

R[5] is selected from the group consisting of H, substituted or unsubstituted C1-C3 alkyl, substituted or unsubstituted C3-C6 cycloalkyl, alkoxy substituted C1-C3 alkyl, cycloalkyl substituted C1-C3 alkyl, substituted or unsubstituted 5-7 membered heteroaryl, and substituted or unsubstituted 5-7 membered non-aromatic heterocycle; R[4] and R[6] together with the hydrazide group connected thereto form a 5-7 membered non-aromatic heterocycle, the heterocycle is optionally substituted by 1-2 groups selected from the group consisting of halogen, CN, OH, R[3] and OR[3]; wherein R[3] is substituted or unsubstituted C1-C3 alkyl, or substituted or unsubstituted C3-C6 cycloalkyl.

In another preferred embodiment, the compound of general formula (1) is represented by the following formula (1C):

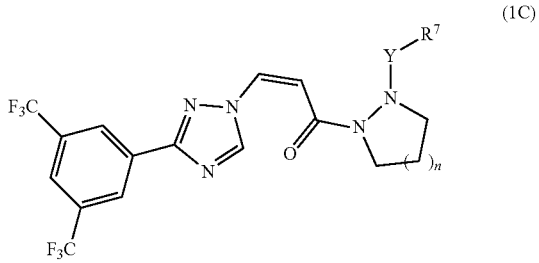

(1C)

or a pharmaceutically acceptable salt thereof, wherein:

n is 1 or 2;

Y is selected from the group consisting of a bond, —$CH_2$—, —$CH_2CH_2$—, —CO—, —$SO_2$—, —SO—, —CON(R[8])—, —$SO_2$N(R[8])—, and —COCON(R[8])—; wherein R[8] is H, substituted or unsubstituted C1-C3 alkyl, or substituted or unsubstituted C3-C6 cycloalkyl; and R[7] is selected from the group consisting of H, substituted or unsubstituted C1-C3 alkyl, substituted or unsubstituted C1-C3 alkoxy, substituted or unsubstituted C3-C6 cycloalkyl, substituted or unsubstituted 5-7 membered heteroaryl, and substituted or unsubstituted 5-7 membered non-aromatic heterocycle.

In another preferred embodiment, the compound of formula (1A) is represented by the following formula (1AA):

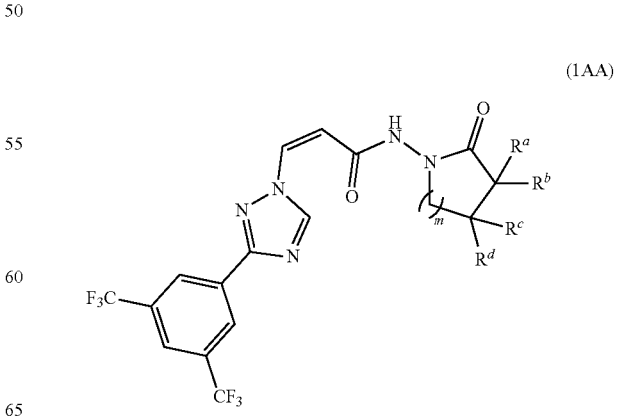

(1AA)

or a pharmaceutically acceptable salt thereof, wherein:

m is 0, 1, 2 or 3;

$R^a$, $R^b$, $R^c$ and $R^d$ are independently selected from the group consisting of H, halogen, CN, $CF_3$, $OCF_3$, $OCH_2CF_3$, OH, $NMe_2$, $R^3$ and $OR^3$; wherein $R^3$ is C1-C3 alkyl group or C3-C6 cycloalkyl group; or $R^a$ and $R^b$ together with a carbon atom connected thereto form a C3-C6 cycloalkyl group or a 3-6 membered non-aromatic heterocycle; or $R^c$ and $R^d$ together with a carbon atom connected thereto form a C3-C6 cycloalkyl group or a 3-6 membered non-aromatic heterocycle; or $R^a$ (or $R^b$) and $R^c$ (or $R^d$) together with a C—C bond connected thereto form a C3-C6 cycloalkyl or 3-6 membered non-aromatic heterocycle;

the 3-6 membered non-aromatic heterocycle is optionally substituted by 1-2 groups selected from the group consisting of halogen, CN, OH, $R^3$ and $OR^3$; wherein $R^3$ is substituted or unsubstituted C1-C3 alkyl, or substituted or unsubstituted C3-C6 cycloalkyl.

In another preferred embodiment, the compound of formula (1A) is represented by the following formula (1AB):

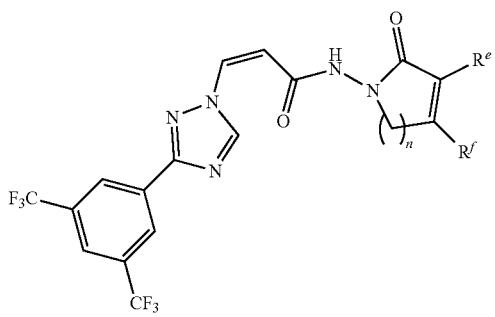

(1AB)

or a pharmaceutically acceptable salt thereof, wherein:

n is 1 or 2;

$R^e$ and $R^f$ are independently selected from group consisting of H, OH, $OCH_2CF_3$, $R^3$ and $OR^3$; wherein $R^3$ is substituted or unsubstituted C1-C3 alkyl, or substituted or unsubstituted C3-C6 cycloalkyl.

In another preferred embodiment, the compound of general formula (1A) is represented by the following formula (1AC):

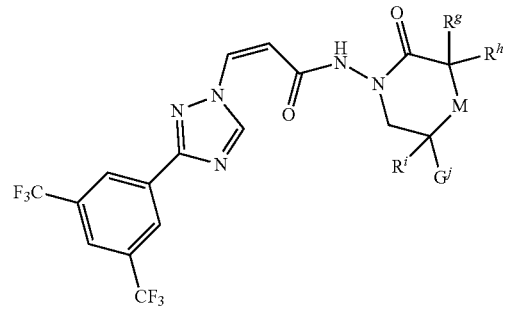

(1AC)

or a pharmaceutically acceptable salt thereof, wherein:

M is —O—, —S—, —$NR^3$— or —$CONR^3$—, wherein $R^3$ is C1-C3 alkyl or C3-C6 cycloalkyl;

$R^g$, $R^h$, $R^i$ and $R^j$ are independently selected from the group consisting of H, $R^3$ and $OR^3$; wherein $R^3$ is substituted or unsubstituted C1-C3 alkyl, or substituted or unsubstituted C3-C6 cycloalkyl; or $R^g$ and $R^h$ together represent a —CO— group, or $R^g$ and $R^h$ together with a carbon atom connected thereto form a C3-C6 cycloalkyl; or $R^i$ and $R^j$ together represent a —CO— group, or $R^i$ and $R^j$ together with a carbon atom connected thereto form a C3-C6 cycloalkyl.

In another preferred embodiment, the compound of formula (1B) is represented by the following formula (1BA):

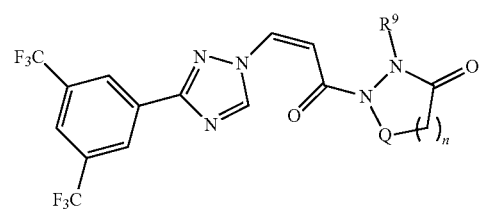

(1BA)

or a pharmaceutically acceptable salt thereof, wherein:

n is 1 or 2;

Q is —$CH_2$— or —CO—;

$R^9$ is selected from the group consisting of H, C1-C3 alkyl, deuterated C1-C3 alkyl, C3-C6 cycloalkyl, amino substituted C1-C3 alkyl-amino, alkoxy substituted C1-C3 alkyl, cycloalkyl substituted C1-C3 alkyl, 5-7 membered heteroaryl, and 5-7 membered non-aromatic heterocycle.

In another preferred embodiment, the compound of general formula (1) is selected from the compounds listed in Table 1.

TABLE 1

Compounds of the invention (1)

| Compound | Structure | Name |
|---|---|---|
| 1 | 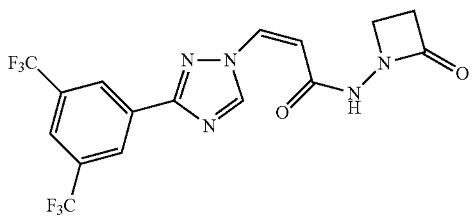 [SMILES: O=C(/C=C\n1cnc(-c2cc(C(F)(F)F)cc(C(F)(F)F)c2)n1)NN1CCC1=O] | (Z)-3-(3-(3,5-bis(trifluoromethyl)phenyl)-1H-1,2,4-triazol-1-yl)-N-(2-oxoazetidin-1-yl)acrylamide |
| 2 | 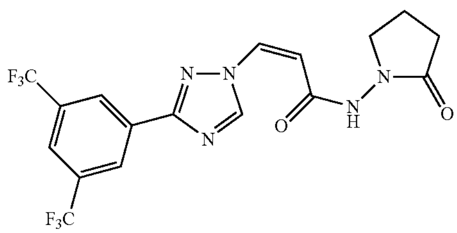 [SMILES: O=C(/C=C\n1cnc(-c2cc(C(F)(F)F)cc(C(F)(F)F)c2)n1)NN1CCCC1=O] | (Z)-3-(3-(3,5-bis(trifluoromethyl)phenyl)-1H-1,2,4-triazol-1-yl)-N-(2-oxopyrrolidin-1-yl)acrylamide |
| 3 | 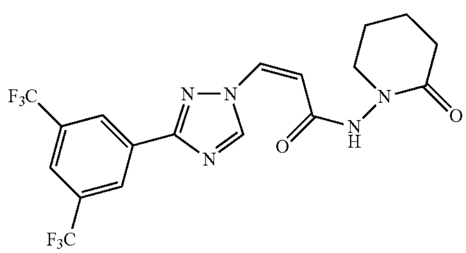 [SMILES: O=C(/C=C\n1cnc(-c2cc(C(F)(F)F)cc(C(F)(F)F)c2)n1)NN1CCCCC1=O] | (Z)-3-(3-(3,5-bis(trifluoromethyl)phenyl)-1H-1,2,4-triazol-1-yl)-N-(2-oxopiperidin-1-yl)acrylamide |
| 4 | 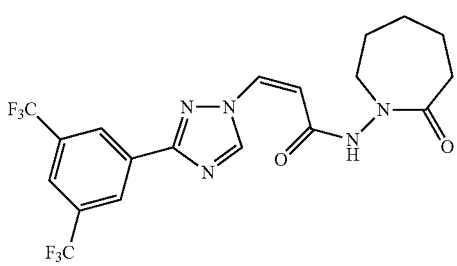 [SMILES: O=C(/C=C\n1cnc(-c2cc(C(F)(F)F)cc(C(F)(F)F)c2)n1)NN1CCCCCC1=O] | (Z)-3-(3-(3,5-bis(trifluoromethyl)phenyl)-1H-1,2,4-triazol-1-yl)-N-(2-oxoazepan-1-yl)acrylamide |
| 5 | 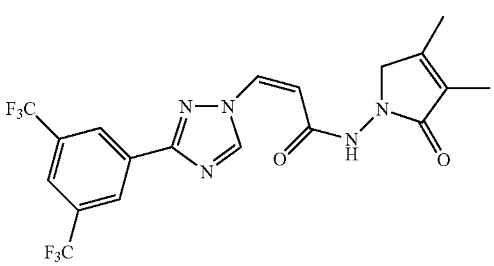 [SMILES: CC1=C(C)C(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(3,4-dimethyl-2-oxo-2,5-dihydro-1H-pyrrol-1-yl)acrylamide |

TABLE 1-continued

Compounds of the invention (1)

| Compound | Structure | Name |
|---|---|---|
| 6 | 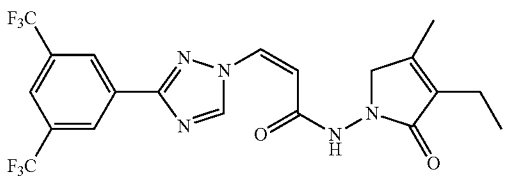 [SMILES: CCC1=C(C)CN(NC(=O)/C=C\n2cnc(-c3cc(C(F)(F)F)cc(C(F)(F)F)c3)n2)C1=O] | (Z)-3-(3-(3,5-bis(trifluoromethyl)phenyl)-1H-1,2,4-triazol-1-yl)-N-(3-ethyl-4-methyl-2-oxo-2,5-dihydro-1H-pyrrol-1-yl)acrylamide |
| 7 | 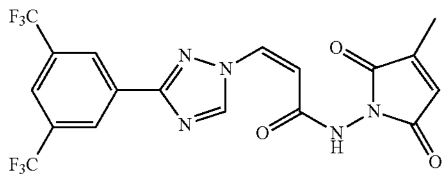 [SMILES: CC1=CC(=O)N(NC(=O)/C=C\n2cnc(-c3cc(C(F)(F)F)cc(C(F)(F)F)c3)n2)C1=O] | (Z)-3-(3-(3,5-bis(trifluoromethyl)phenyl)-1H-1,2,4-triazol-1-yl)-N-(3-methyl-2,5-dioxo-2,5-dihydro-1H-pyrrol-1-yl)acrylamide |
| 8 | 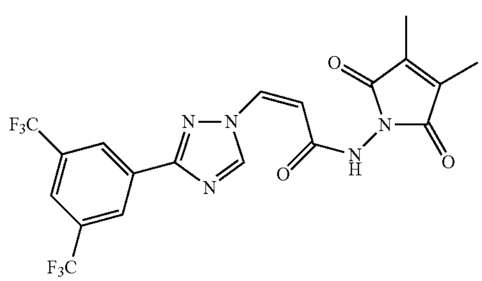 [SMILES: CC1=C(C)C(=O)N(NC(=O)/C=C\n2cnc(-c3cc(C(F)(F)F)cc(C(F)(F)F)c3)n2)C1=O] | (Z)-3-(3-(3,5-bis(trifluoromethyl)phenyl)-1H-1,2,4-triazol-1-yl)-N-(3,4-dimethyl-2,5-dioxo-2,5-dihydro-1H-pyrrol-1-yl)acrylamide |
| 9 | 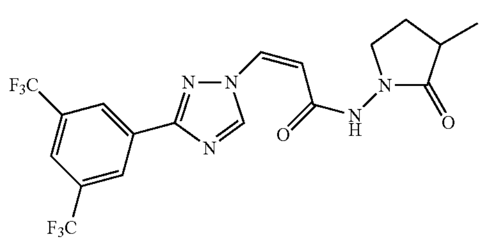 [SMILES: CC1CCN(NC(=O)/C=C\n2cnc(-c3cc(C(F)(F)F)cc(C(F)(F)F)c3)n2)C1=O] | (Z)-3-(3-(3,5-bis(trifluoromethyl)phenyl)-1H-1,2,4-triazol-1-yl)-N-(3-methyl-2-oxopyrrolidin-1-yl)acrylamide |
| 10 | 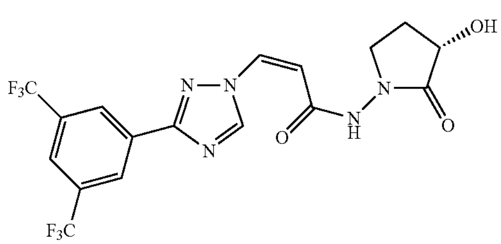 [SMILES: O=C(/C=C\n1cnc(-c2cc(C(F)(F)F)cc(C(F)(F)F)c2)n1)NN1CC[C@H](O)C1=O] | (S,Z)-3-(3-(3,5-bis(trifluoromethyl)phenyl)-1H-1,2,4-triazol-1-yl)-N-(3-hydroxy-2-oxopyrrolidin-1-yl)acrylamide |

TABLE 1-continued

Compounds of the invention (1)

| Compound | Structure | Name |
|---|---|---|
| 11 | 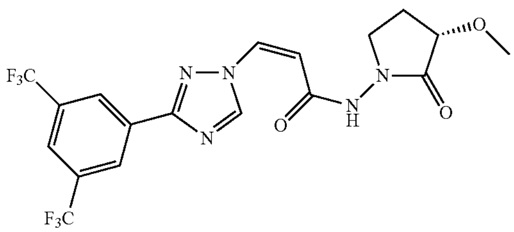 [SMILES: CO[C@H]1CCN(NC(=O)/C=C\n2cnc(-c3cc(C(F)(F)F)cc(C(F)(F)F)c3)n2)C1=O] | (S,Z)-3-(3-(3,5-bis(trifluoromethyl)phenyl)-1H-1,2,4-triazol-1-yl)-N-(3-methoxy-2-oxopyrrolidin-1-yl)acrylamide |
| 12 | 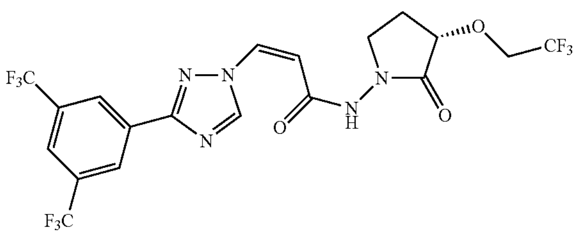 [SMILES: O=C(/C=C\n1cnc(-c2cc(C(F)(F)F)cc(C(F)(F)F)c2)n1)NN1CC[C@H](OCC(F)(F)F)C1=O] | (S,Z)-3-(3-(3,5-bis(trifluooromethyl)phenyl)-1H-1,2,4-triazol-1-yl)-N-(2-oxo-3-(2,2,2-trifluoroethoxy)pyrrolidin-1-yl)acrylamide |
| 13 | 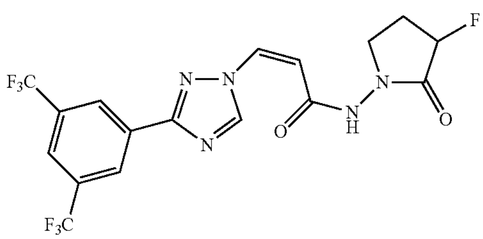 [SMILES: O=C(/C=C\n1cnc(-c2cc(C(F)(F)F)cc(C(F)(F)F)c2)n1)NN1CCC(F)C1=O] | (Z)-3-(3-(3,5-bis(trifluoromethyl)phenyl)-1H-1,2,4-triazol-1-yl)-N-(3-fluoro-2-oxopyrrolidin-1-yl)acrylamide |
| 14 | 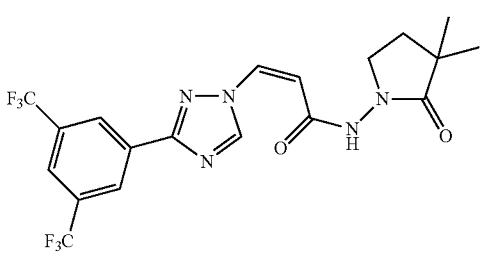 | (Z)-3-(3-(3,5-bis(trifluoromethyl)phenyl)-1H-1,2,4-triazol-1-yl)-N-(3,3-dimethyl-2-oxopyrrolidin-1-yl)acrylamide |
| 15 | 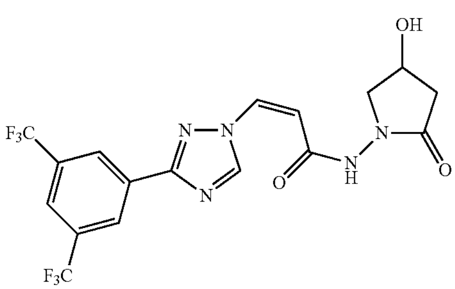 [SMILES: O=C(/C=C\n1cnc(-c2cc(C(F)(F)F)cc(C(F)(F)F)c2)n1)NN1CC(O)CC1=O] | (Z)-3-(3-(3,5-bis(trifluoromethyl)phenyl)-1H-1,2,4-triazol-1-yl)-N-(4-hydroxy-2-oxopyrrolidin-1-yl)acrylamide |

TABLE 1-continued

Compounds of the invention (1)

| Compound | Structure | Name |
|---|---|---|
| 16 | 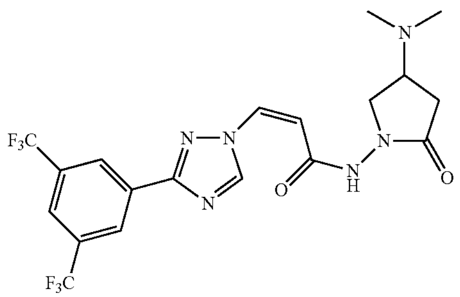 [SMILES: CN(C)C1CC(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(4-(dimethylamino)-2-oxopyrrolidin-1-yl)acrylamide |
| 17 | 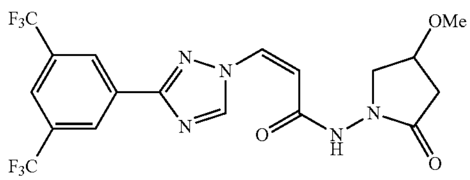 [SMILES: COC1CC(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(4-methoxy-2-oxopyrrolidin-1-yl)acrylamide |
| 18 | 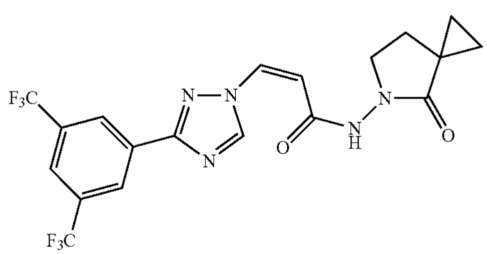 [SMILES: O=C(/C=C\n1cnc(-c2cc(C(F)(F)F)cc(C(F)(F)F)c2)n1)NN1CCC2(CC2)C1=O] | (Z)-3-(3-(3,5-bis(trifluoromethyl)phenyl)-1H-1,2,4-triazol-1-yl)-N-(4-oxo-5-azaspiro[2.4]heptan-5-yl)acrylamide |
| 19 | 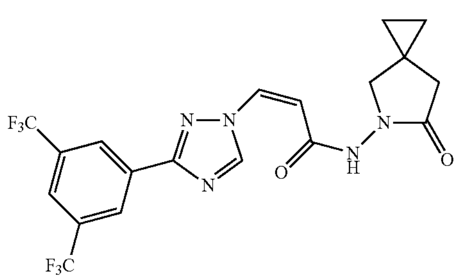 [SMILES: O=C(/C=C\n1cnc(-c2cc(C(F)(F)F)cc(C(F)(F)F)c2)n1)NN1CC2(CC2)CC1=O] | (Z)-3-(3-(3,5-bis(trifluoromethyl)phenyl)-1H-1,2,4-triazol-1-yl)-N-(6-oxo-5-azaspiro[2.4]heptan-5-yl)acrylamide |
| 20 | 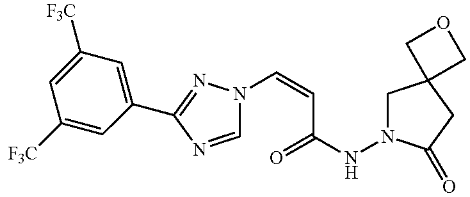 [SMILES: O=C(/C=C\n1cnc(-c2cc(C(F)(F)F)cc(C(F)(F)F)c2)n1)NN1CC2(COC2)CC1=O] | ((Z)-3-(3-(3,5-bis(trifluoromethyl)phenyl)-1H-1,2,4-triazol-1-yl)-N-(7-oxo-2-oxa-6-azaspiro[3.4]octan-6-yl)acrylamide |

TABLE 1-continued

Compounds of the invention (1)

| Compound | Structure | Name |
|---|---|---|
| 21 | | (Z)-3-(3-(3,5-bis(trifluoromethyl)phenyl)-1H-1,2,4-triazol-1-yl)-N-(3-oxo-8-oxa-2-azaspiro[4.5]decan-2-yl)acrylamide |
| 22 | | (Z)-3-(3-(3,5-bis(trifluoromethyl)phenyl)-1H-1,2,4-triazol-1-yl)-N-(3-oxo-2-azaspiro[4.5]decan-2-yl)acrylamide |
| 23 | | (Z)-3-(3-(3,5-bis(trifluoromethyl)phenyl)-1H-1,2,4-triazol-1-yl)-N-(8-methyl-3-oxo-2,8-diazaspiro[4.5]decan-2-yl)acrylamide |
| 24 | | (Z)-N-(8-acetyl-3-oxo-2,8-diazaspiro[4.5]decan-2-yl)-3-(3-(3,5-bis(trifluoromethyl)phenyl)-1H-1,2,4-triazol-1-yl)acrylamide |
| 25 | | (Z)-3-(3-(3,5-bis(trifluoromethyl)phenyl)-1H-1,2,4-triazol-1-yl)-N-(2-methyl-7-oxo-2,6-diazaspiro[3.4]octan-6-yl)acrylamide |

TABLE 1-continued

Compounds of the invention (1)

| Compound | Structure | Name |
|---|---|---|
| 26 | | (Z)-3-(3-(3,5-bis(trifluoromethyl)phenyl)-1H-1,2,4-triazol-1-yl)-N-(2-methyl-5-oxo-2,6-diazaspiro[3.4]octan-6-yl)acrylamide |
| 27 | | (Z)-N-(8-acetyl-1-oxo-2,8-diazaspiro[4.5]decan-2-yl)-3-(3-(3,5-bis(trifluoromethyl)phenyl)-1H-1,2,4-triazol-1-yl)acrylamide |
| 28 | | (Z)-3-(3-(3,5-bis(trifluoromethyl)phenyl)-1H-1,2,4-triazol-1-yl)-N-(1-oxooctahydro-2H-isoindol-2-yl)acrylamide |
| 29 | | (Z)-3-(3-(3,5-bis(trifluoromethyl)phenyl)-1H-1,2,4-triazol-1-yl)-N-((1R,5S)-2-oxo-3-azabicyclo[3.1.0]hexan-3-yl)acrylamide |
| 30 | | (Z)-3-(3-(3,5-bis(trifluoromethyl)phenyl)-1H-1,2,4-triazol-1-yl)-N-((1S,4R)-3-oxo-2-azabicyclo[2.2.1]hept-5-en-2-yl)acrylamide |

TABLE 1-continued

Compounds of the invention (1)

| Compound | Structure | Name |
|---|---|---|
| 31 | 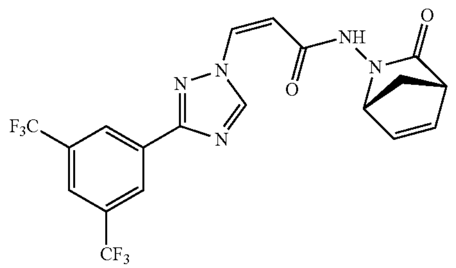 [SMILES: O=C(/C=C\n1cnc(-c2cc(C(F)(F)F)cc(C(F)(F)F)c2)n1)NN1C(=O)[C@@H]2C=C[C@H]1C2] | (Z)-3-(3-(3,5-bis(trifluoromethyl)phenyl)-1H-1,2,4-triazol-1-yl)-N-((1R,4S)-3-oxo-2-azabicyclo[2.2.1]hept-5-en-2-yl)acrylamide |
| 32 | 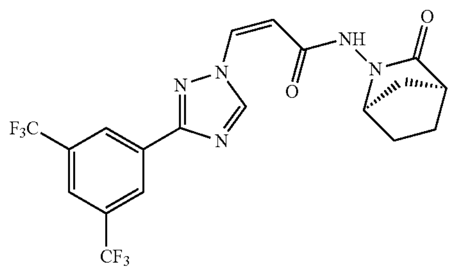 [SMILES: O=C(/C=C\n1cnc(-c2cc(C(F)(F)F)cc(C(F)(F)F)c2)n1)NN1C(=O)[C@H]2CC[C@@H]1C2] | (Z)-3-(3-(3,5-bis(trifluoromethyl)phenyl)-1H-1,2,4-triazol-1-yl)-N-((1R,4S)-3-oxo-2-azabicyclo[2.2.1]heptan-2-yl)acrylamide |
| 33 | 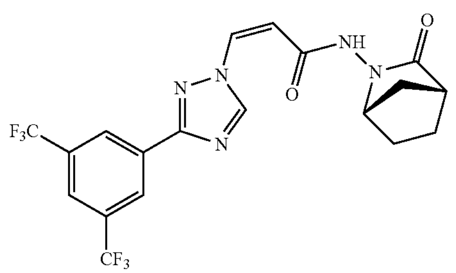 [SMILES: O=C(/C=C\n1cnc(-c2cc(C(F)(F)F)cc(C(F)(F)F)c2)n1)NN1C(=O)[C@@H]2CC[C@H]1C2] | (Z)-3-(3-(3,5-bis(trifluoromethyl)phenyl)-1H-1,2,4-triazol-1-yl)-N-((1S,4R)-3-oxo-2-azabicyclo[2.2.1]heptan-2-yl)acrylamide |
| 34 | 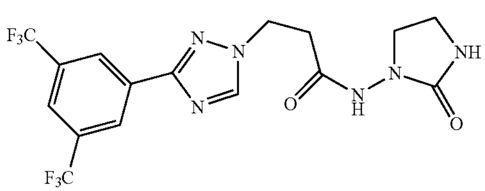 [SMILES: O=C(CCn1cnc(-c2cc(C(F)(F)F)cc(C(F)(F)F)c2)n1)NN1CCNC1=O] | (Z)-3-(3-(3,5-bis(trifluoromethyl)phenyl)-1H-1,2,4-triazol-1-yl)-N-(2-oxoimidazolidin-1-yl)acrylamide |
| 35 | 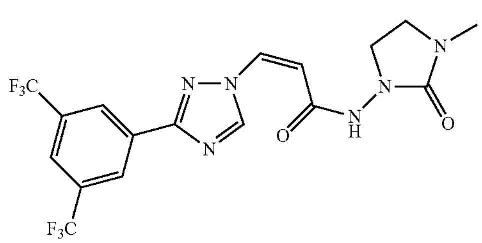 | (Z)-3-(3-(3,5-bis(trifluoromethyl)phenyl)-1H-1,2,4-triazol-1-yl)-N-(3-methyl-2-oxoimidazolidin-1-yl)acrylamide |

TABLE 1-continued

Compounds of the invention (1)

| Compound | Structure | Name |
|---|---|---|
| 36 | | (Z)-3-(3-(3,5-bis(trifluoromethyl)phenyl)-1H-1,2,4-triazol-1-yl)-N-(2-oxotetrahydropyrimidin-1(2H)-yl)acrylamide |
| 37 | | (Z)-3-(3-(3,5-bis(trifluoromethyl)phenyl)-1H-1,2,4-triazol-1-yl)-N-(3-methyl-2-oxotetrahydropyrimidin-1(2H)-yl)acrylamide |
| 38 | | (Z)-3-(3-(3,5-bis(trifluoromethyl)phenyl)-1H-1,2,4-triazol-1-yl)-N-(3-oxomorpholino)acrylamide |
| 39 | | (Z)-3-(3-(3,5-bis(trifluoromethyl)phenyl)-1H-1,2,4-triazol-1-yl)-N-(2-oxopiperazin-1-yl)acrylamide |
| 40 | | (Z)-N-(4-acetyl-2-oxopiperazin-1-yl)-3-(3-(3,5-bis(trifluoromethyl)phenyl)-1H-1,2,4-triazol-1-yl)acrylamide |

TABLE 1-continued

Compounds of the invention (1)

| Compound | Structure | Name |
|---|---|---|
| 41 | 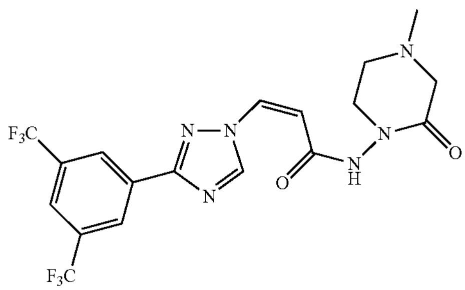 [SMILES: CN1CCN(NC(=O)/C=C\n2cnc(-c3cc(C(F)(F)F)cc(C(F)(F)F)c3)n2)C(=O)C1] | (Z)-3-(3-(3,5-bis(trifluoromethyl)phenyl)-1H-1,2,4-triazol-1-yl)-N-(4-methyl-2-oxopiperazin-1-yl)acrylamide |
| 42 | 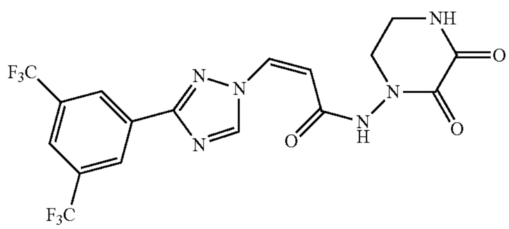 [SMILES: O=C(/C=C\n1cnc(-c2cc(C(F)(F)F)cc(C(F)(F)F)c2)n1)NN1CCNC(=O)C1=O] | (Z)-3-(3-(3,5-bis(trifluoromethyl)phenyl)-1H-1,2,4-triazol-1-yl)-N-(2,3-dioxopiperazin-1-yl)acrylamide |
| 43 | 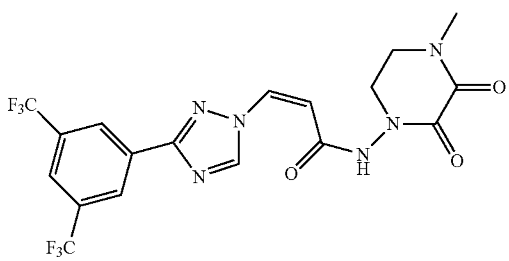 [SMILES: CN1CCN(NC(=O)/C=C\n2cnc(-c3cc(C(F)(F)F)cc(C(F)(F)F)c3)n2)C(=O)C1=O] | (Z)-3-(3-(3,5-bis(trifluoromethyl)phenyl)-1H-1,2,4-triazol-1-yl)-N-(4-methyl-2,3-dioxopiperazin-1-yl)acrylamide |
| 44 | 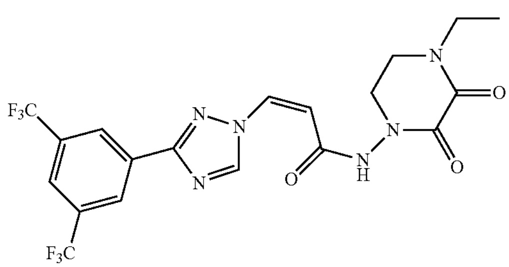 [SMILES: CCN1CCN(NC(=O)/C=C\n2cnc(-c3cc(C(F)(F)F)cc(C(F)(F)F)c3)n2)C(=O)C1=O] | (Z)-3-(3-(3,5-bis(trifluoromethyl)phenyl)-1H-1,2,4-triazol-1-yl)-N-(4-ethyl-2,3-dioxopiperazin-1-yl)acrylamide |
| 45 | 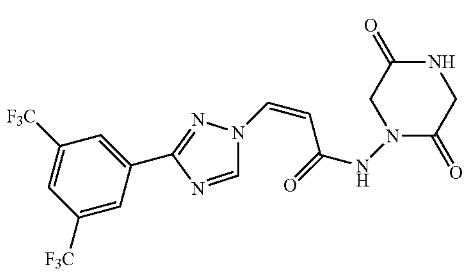 [SMILES: O=C(/C=C\n1cnc(-c2cc(C(F)(F)F)cc(C(F)(F)F)c2)n1)NN1CC(=O)NCC1=O] | (Z)-3-(3-(3,5-bis(trifluoromethyl)phenyl)-1H-1,2,4-triazol-1-yl)-N-(2,5-dioxopiperazin-1-yl)acrylamide |

TABLE 1-continued

Compounds of the invention (1)

| Compound | Structure | Name |
|---|---|---|
| 46 | 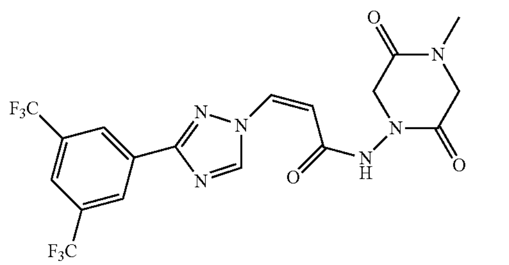 [SMILES: CN1CC(=O)N(NC(=O)/C=C\n2cnc(-c3cc(C(F)(F)F)cc(C(F)(F)F)c3)n2)CC1=O] | (Z)-3-(3-(3,5-bis(trifluoromethyl)phenyl)-1H-1,2,4-triazol-1-yl)-N-(4-methyl-2,5-dioxopiperazin-1-yl)acrylamide |
| 47 | 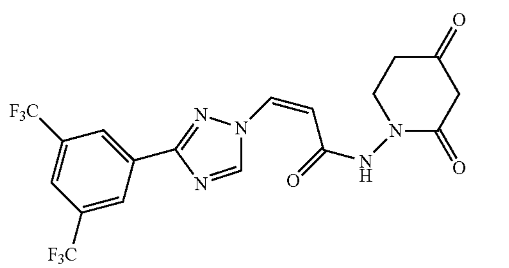 [SMILES: O=C1CCN(NC(=O)/C=C\n2cnc(-c3cc(C(F)(F)F)cc(C(F)(F)F)c3)n2)C(=O)C1] | (Z)-3-(3-(3,5-bis(trifluoromethyl)phenyl)-1H-1,2,4-triazol-1-yl)-N-(2,4-dioxopiperidin-1-yl)acrylamide |
| 48 | 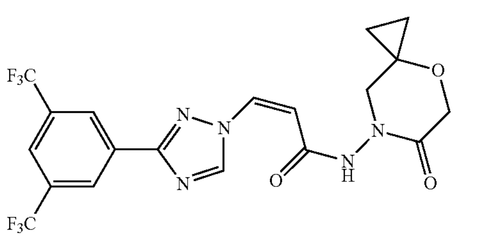 [SMILES: O=C(/C=C\n1cnc(-c2cc(C(F)(F)F)cc(C(F)(F)F)c2)n1)NN1CC2(CC2)OCC1=O] | (Z)-3-(3-(3,5-bis(trifluoromethyl)phenyl)-1H-1,2,4-triazol-1-yl)-N-(6-oxo-4-oxa-7-azaspiro[2.5]octan-7-yl)acrylamide |
| 49 | 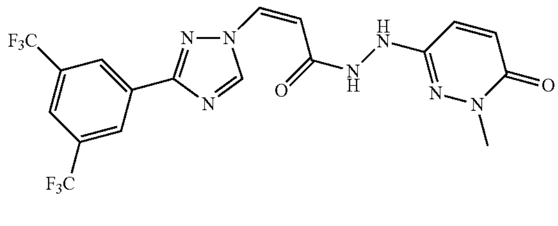 [SMILES: Cn1nc(NNC(=O)/C=C\n2cnc(-c3cc(C(F)(F)F)cc(C(F)(F)F)c3)n2)ccc1=O] | (Z)-3-(3-(3,5-bis(trifluoromethyl)phenyl)-1H-1,2,4-triazol-1-yl)-N'-(1-methyl-6-oxo-1,6-dihydropyridazin-3-yl)acrylohydrazide |
| 50 | 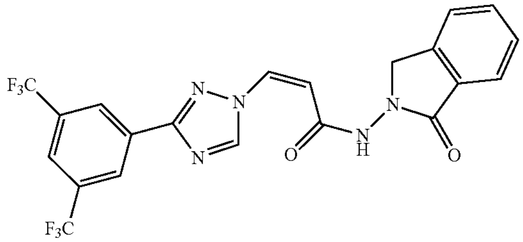 [SMILES: O=C(/C=C\n1cnc(-c2cc(C(F)(F)F)cc(C(F)(F)F)c2)n1)NN1Cc2ccccc2C1=O] | (Z)-3-(3-(3,5-bis(trifluoromethyl)phenyl)-1H-1,2,4-triazol-1-yl)-N-(1-oxoisoindolin-2-yl)acrylamide |

TABLE 1-continued

Compounds of the invention (1)

| Compound | Structure | Name |
|---|---|---|
| 51 | 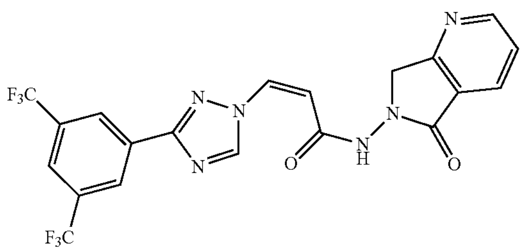 [SMILES: O=C(/C=C\n1cnc(-c2cc(C(F)(F)F)cc(C(F)(F)F)c2)n1)NN1Cc2ncccc2C1=O] | (Z)-3-(3-(3,5-bis(trifluoromethyl)phenyl)-1H-1,2,4-triazol-1-yl)-N-(5-oxo-5,7-dihydro-6H-pyrrolo[3,4-b]pyridin-6-yl)acrylamide |
| 52 | 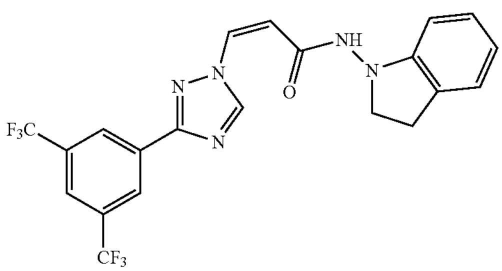 | (Z)-3-(3-(3,5-bis(trifluoromethyl)phenyl)-1H-1,2,4-triazol-1-yl)-N-(indolin-1-yl)acrylamide |
| 53 | 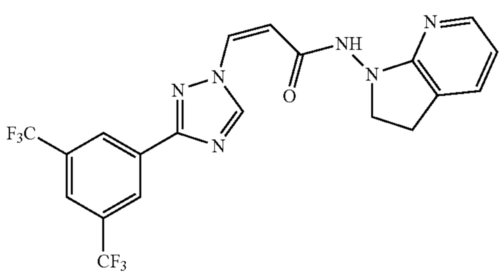 [SMILES: O=C(/C=C\n1cnc(-c2cc(C(F)(F)F)cc(C(F)(F)F)c2)n1)NN1CCc2cccnc21] | (Z)-3-(3-(3,5-bis(trifluoromethyl)phenyl)-1H-1,2,4-triazol-1-yl)-N-(2,3-dihydro-1H-pyrrolo[2,3-b]pyridin-1-yl)acrylamide |
| 54 | 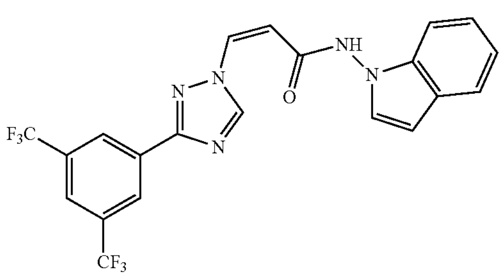 [SMILES: O=C(/C=C\n1cnc(-c2cc(C(F)(F)F)cc(C(F)(F)F)c2)n1)Nn1ccc2ccccc21] | (Z)-3-(3-(3,5-bis(trifluoromethyl)phenyl)-1H-1,2,4-triazol-1-yl)-N-(1H-indol-1-yl)acrylamide |
| 55 | 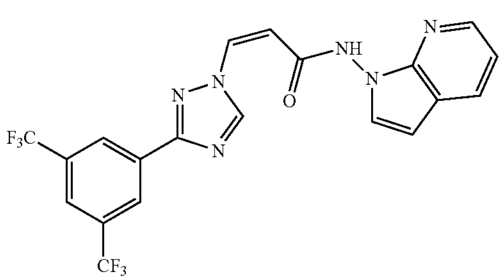 [SMILES: O=C(/C=C\n1cnc(-c2cc(C(F)(F)F)cc(C(F)(F)F)c2)n1)Nn1ccc2cccnc21] | (Z)-3-(3-(3,5-bis(trifluoromethyl)phenyl)-1H-1,2,4-triazol-1-yl)-N-(1H-pyrrolo[2,3-b]pyridin-1-yl)acrylamide |

TABLE 1-continued

Compounds of the invention (1)

| Compound | Structure | Name |
|---|---|---|
| 56 | 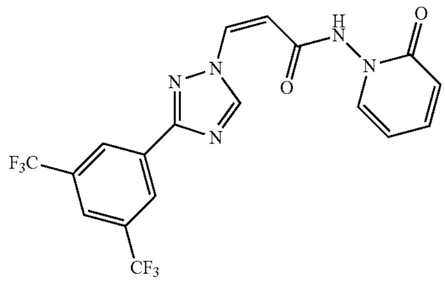 [SMILES: O=C(/C=C\n1cnc(-c2cc(C(F)(F)F)cc(C(F)(F)F)c2)n1)Nn1ccccc1=O] | (Z)-3-(3-(3,5-bis(trifluoromethyl)phenyl)-1H-1,2,4-triazol-1-yl)-N-(2-oxopyridin-1(2H)-yl)acrylamide |
| 57 | 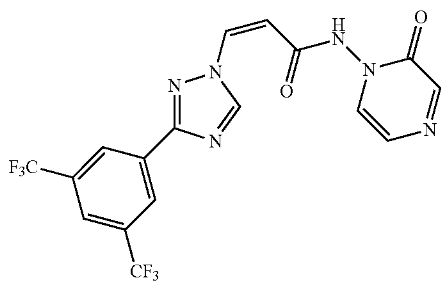 [SMILES: O=C(/C=C\n1cnc(-c2cc(C(F)(F)F)cc(C(F)(F)F)c2)n1)Nn1ccncc1=O] | (Z)-3-(3-(3,5-bis(trifluoromethyl)phenyl)-1H-1,2,4-triazol-1-yl)-N-(2-oxopyrazin-1(2H)-yl)acrylamide |
| 58 | 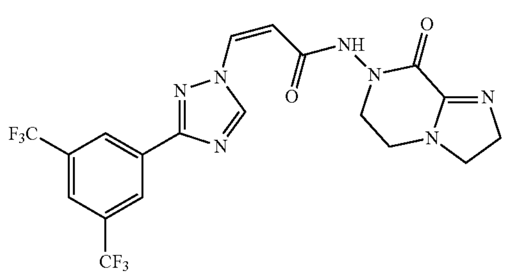 [SMILES: O=C(/C=C\n1cnc(-c2cc(C(F)(F)F)cc(C(F)(F)F)c2)n1)NN1CCN2CCN=C2C1=O] | (Z)-3-(3-(3,5-bis(trifluoromethyl)phenyl)-1H-1,2,4-triazol-1-yl)-N-(8-oxo-2,5,6,8-tetrahydroimidazo[1,2-a]pyrazin-7(3H)-yl)acrylamide |
| 59 | 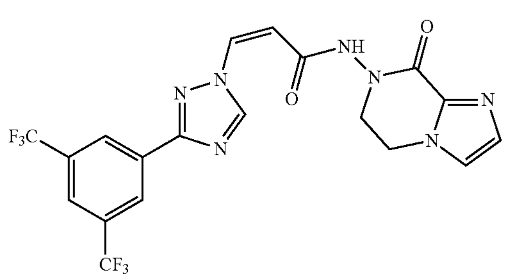 [SMILES: O=C(/C=C\n1cnc(-c2cc(C(F)(F)F)cc(C(F)(F)F)c2)n1)NN1CCn2ccnc2C1=O] | (Z)-3-(3-(3,5-bis(trifluoromethyl)phenyl)-1H-1,2,4-triazol-1-yl)-N-(8-oxo-5,6-dihydroimidazo[1,2-a]pyrazin-7(8H)-yl)acrylamide |

TABLE 1-continued

Compounds of the invention (1)

| Compound | Structure | Name |
|---|---|---|
| 60 | 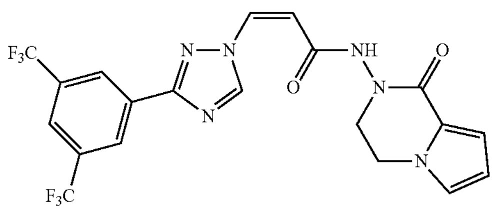 [SMILES: O=C(/C=C\n1cnc(-c2cc(C(F)(F)F)cc(C(F)(F)F)c2)n1)NN1CCn2cccc2C1=O] | (Z)-3-(3-(3,5-bis(trifluoromethyl)phenyl)-1H-1,2,4-triazol-1-yl)-N-(1-oxo-3,4-dihydropyrrolo[1,2-a]pyrazin-2(1H)-yl)acrylamide |
| 61 | 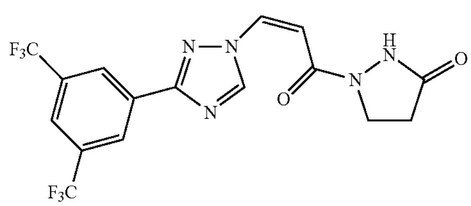 [SMILES: O=C1CCN(C(=O)/C=C\n2cnc(-c3cc(C(F)(F)F)cc(C(F)(F)F)c3)n2)N1] | (Z)-1-(3-(3-(3,5-bis(trifluoromethyl)phenyl)-1H-1,2,4-triazol-1-yl)acryloyl)pyrazolidin-3-one |
| 62 | 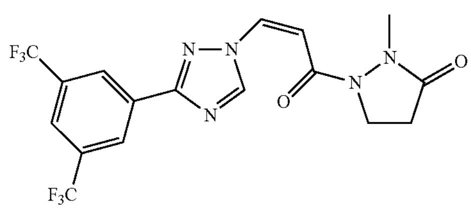 [SMILES: CN1C(=O)CCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-methylpyrazolidin-3-one |
| 63 | 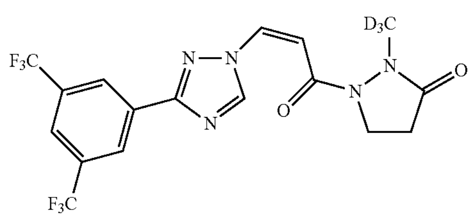 [SMILES: [2H]C([2H])([2H])N1C(=O)CCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-(methyl-d3)pyrazolidin-3-one |
| 64 | 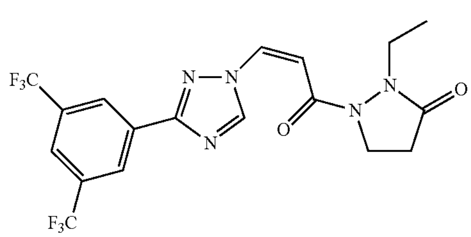 [SMILES: CCN1C(=O)CCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-ethylpyrazolidin-3-one |
| 65 | 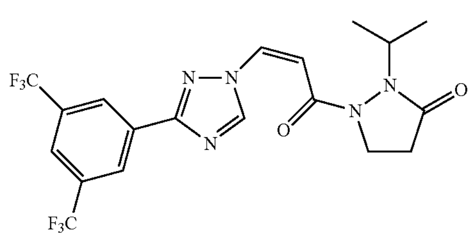 [SMILES: CC(C)N1C(=O)CCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-isopropylpyrazolidin-3-one |

TABLE 1-continued

Compounds of the invention (1)

| Compound | Structure | Name |
|---|---|---|
| 66 | 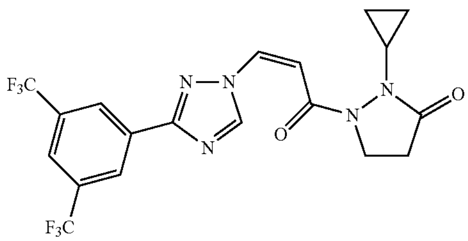 [SMILES: O=C(/C=C\n1cnc(-c2cc(C(F)(F)F)cc(C(F)(F)F)c2)n1)N1CCC(=O)N1C1CC1] | (Z)-1-(3-(3-(3,5-bis(trifluoromethyl)phenyl)-1H-1,2,4-triazol-1-yl)acryloyl)-2-cyclopropylpyrazolidin-3-one |
| 67 | 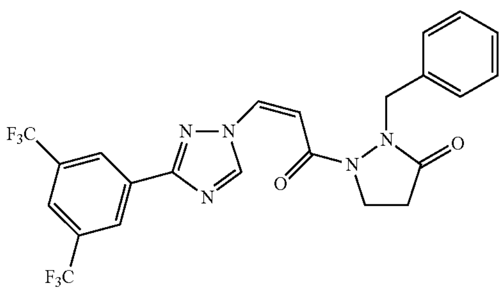 [SMILES: O=C(/C=C\n1cnc(-c2cc(C(F)(F)F)cc(C(F)(F)F)c2)n1)N1CCC(=O)N1Cc1ccccc1] | (Z)-2-benzyl-1-(3-(3-(3,5-bis(trifluoromethyl)phenyl)-1H-1,2,4-triazol-1-yl)acryloyl)pyrazolidin-3-one |
| 68 | 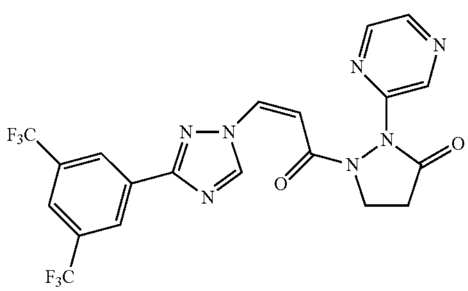 [SMILES: O=C(/C=C\n1cnc(-c2cc(C(F)(F)F)cc(C(F)(F)F)c2)n1)N1CCC(=O)N1c1cnccn1] | (Z)-1-(3-(3-(3,5-bis(trifluoromethyl)phenyl)-1H-1,2,4-triazol-1-yl)acryloyl)-2-(pyrazin-2-yl)pyrazolidin-3-one |
| 69 | 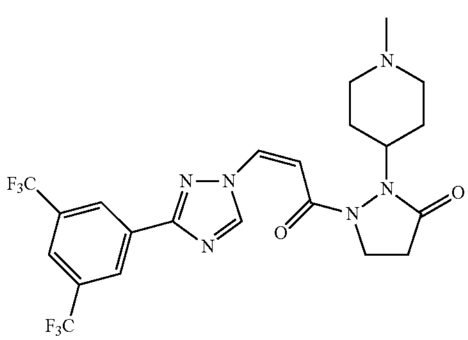 [SMILES: CN1CCC(N2C(=O)CCN2C(=O)/C=C\n2cnc(-c3cc(C(F)(F)F)cc(C(F)(F)F)c3)n2)CC1] | (Z)-1-(3-(3-(3,5-bis(trifluoromethyl)phenyl)-1H-1,2,4-triazol-1-yl)acryloyl)-2-(1-methylpiperidin-4-yl)pyrazolidin-3-one |

TABLE 1-continued

Compounds of the invention (1)

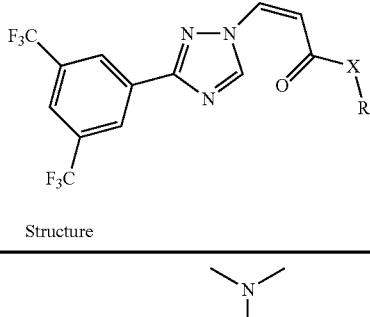

| Compound | Structure | Name |
|---|---|---|
| 70 | 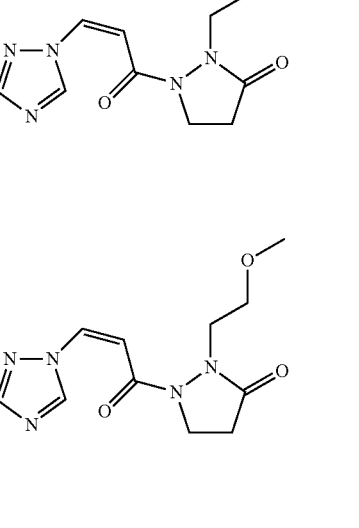 | (Z)-1-(3-(3-(3,5-bis(trifluoromethyl)phenyl)-1H-1,2,4-triazol-1-yl)acryloyl)-2-(2-(dimethylamino)ethyl)pyrazolidin-3-one |
| 71 | 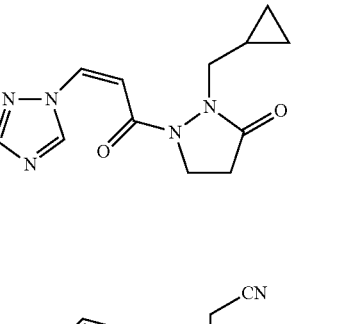 | (Z)-1-(3-(3-(3,5-bis(trifluoromethyl)phenyl)-1H-1,2,4-triazol-1-yl)acryloyl)-2-(2-methoxyethyl)pyrazolidin-3-one |
| 72 | 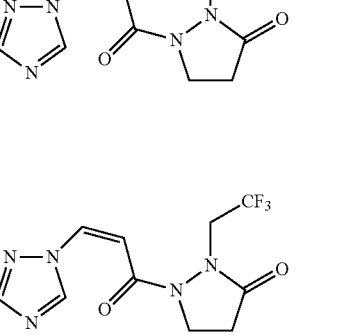 | (Z)-1-(3-(3-(3,5-bis(trifluoromethyl)phenyl)-1H-1,2,4-triazol-1-yl)acryloyl)-2-(cyclopropylmethyl)pyrazolidin-3-one |
| 73 | 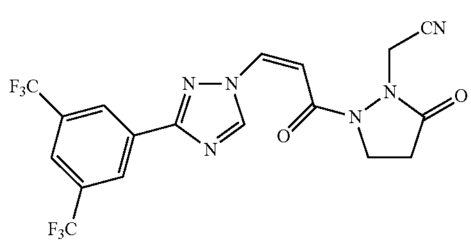 | (Z)-2-(2-(3-(3-(3,5-bis(trifluoromethyl)phenyl)-1H-1,2,4-triazol-1-yl)acryloyl)-5-oxopyrazolidin-1-yl)acetonitrile |
| 74 | 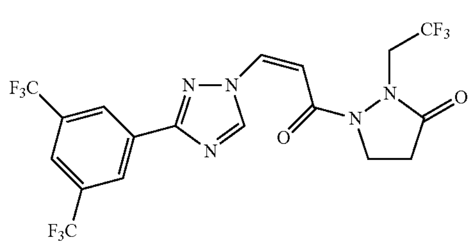 [SMILES: N#CCN1C(=O)CCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-(2,2,2-trifluoroethyl)pyrazolidin-3-one |

TABLE 1-continued

Compounds of the invention (1)

| Compound | Structure | Name |
| --- | --- | --- |
| 75 | 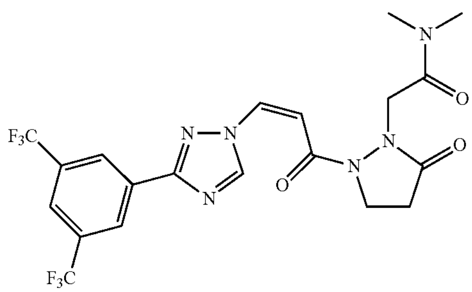 [SMILES: CN(C)C(=O)CN1C(=O)CCN1C(=O)/C=C\n1cnc(-c2cc(C(F)(F)F)cc(C(F)(F)F)c2)n1] | (Z)-2-(2-(3-(3-(3,5-bis(trifluoromethyl)phenyl)-1H-1,2,4-triazol-1-yl)acryloyl)-5-oxopyrazolidin-1-yl)-N,N-dimethylacetamide |
| 76 | 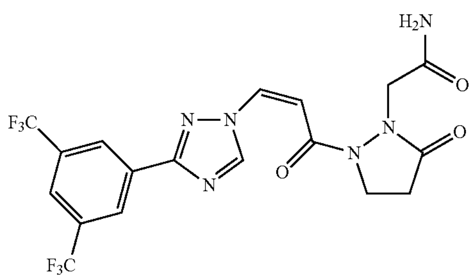 [SMILES: NC(=O)CN1C(=O)CCN1C(=O)/C=C\n1cnc(-c2cc(C(F)(F)F)cc(C(F)(F)F)c2)n1] | (Z)-2-(2-(3-(3-(3,5-bis(trifluoromethyl)phenyl)-1H-1,2,4-triazol-1-yl)acryloyl)-5-oxopyrazolidin-1-yl)acetamide |
| 77 | 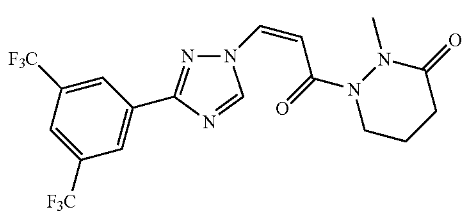 [SMILES: CN1C(=O)CCCN1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-methyltetrahydropyridazin-3(2H)-one |
| 78 | 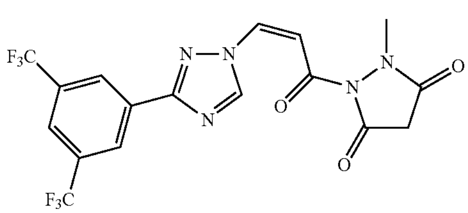 [SMILES: CN1C(=O)CC(=O)N1C(=O)/C=C\n1cnc(-c2cc(C(F)(F)F)cc(C(F)(F)F)c2)n1] | (Z)-1-(3-(3-(3,5-bis(trifluoromethyl)phenyl)-1H-1,2,4-triazol-1-yl)acryloyl)-2-methylpyrazolidine-3,5-dione |
| 79 | 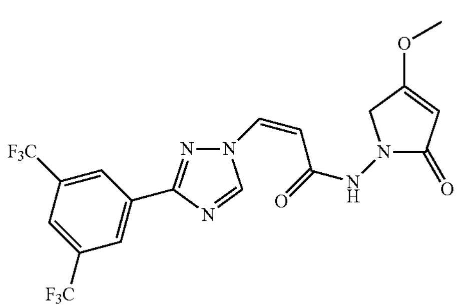 [SMILES: COC1=CC(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(4-methoxy-2-oxo-2,5-dihydro-1H-pyrrol-1-yl)acrylamide |

TABLE 1-continued

Compounds of the invention (1)

| Compound | Structure | Name |
|---|---|---|
| 80 | | (Z)-3-(3-(3,5-bis(trifluoromethyl)phenyl)-1H-1,2,4-triazol-1-yl)-N-(4-ethoxy-2-oxo-2,5-dihydro-1H-pyrrol-1-yl)acrylamide |
| 81 | | (Z)-3-(3-(3,5-bis(trifluoromethyl)phenyl)-1H-1,2,4-triazol-1-yl)-N-(4-(2-methoxyethoxy-2-oxo-2,5-dihydro-1H-pyrrol-1-yl)acrylamide |
| 82 | | (Z)-3-(3-(3,5-bis(trifluoromethyl)phenyl)-1H-1,2,4-triazol-1-yl)-N-(4-(methoxy-d3)-2-oxo-2,5-dihydro-1H-pyrrol-1-yl)acrylamide |
| 83 | | (Z)-3-(3-(3,5-bis(trifluoromethyl)phenyl)-1H-1,2,4-triazol-1-yl)-N-(2-oxo-4-(2,2,2-trifluoroethoxy)-2,5-dihydro-1H-pyrrol-1-yl)acrylamide |

TABLE 1-continued

Compounds of the invention (1)

| Compound | Structure | Name |
|---|---|---|
| 84 | 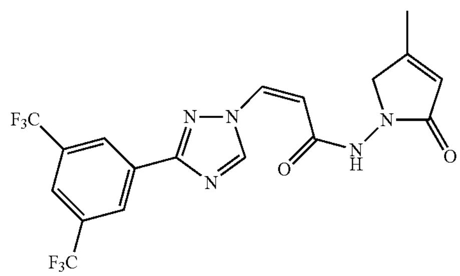 [SMILES: CC1=CC(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(4-methyl-2-oxo-2,5-dihydro-1H-pyrrol-1-yl)acrylamide |
| 85 | 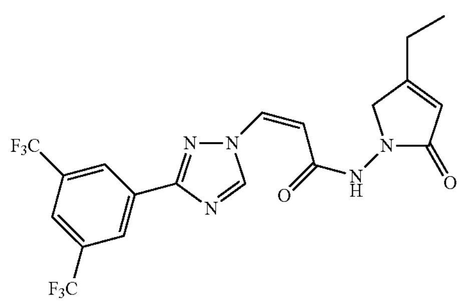 [SMILES: CCC1=CC(=O)N(NC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-(4-ethyl-2-oxo-2,5-dihydro-1H-pyrrol-1-yl)acrylamide |
| 86 | 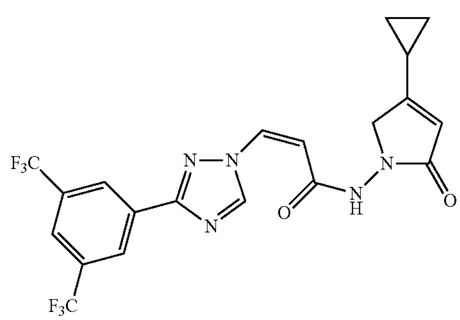 [SMILES: O=C(/C=C\n1cnc(-c2cc(C(F)(F)F)cc(C(F)(F)F)c2)n1)NN1CC(C2CC2)=CC1=O] | (Z)-3-(3-(3,5-bis(trifluoromethyl)phenyl)-1H-1,2,4-triazol-1-yl)-N-(4-cyclopropyl-2-oxo-2,5-dihydro-1H-pyrrol-1-yl)acrylamide |
| 87 | 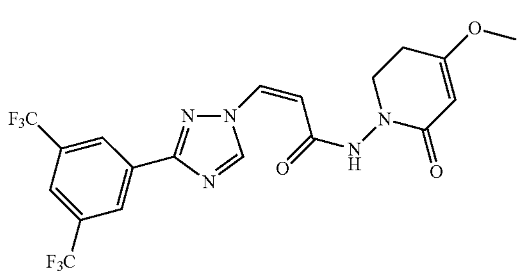 [SMILES: COC1=CC(=O)N(NC(=O)/C=C\n2cnc(-c3cc(C(F)(F)F)cc(C(F)(F)F)c3)n2)CC1] | (Z)-3-(3-(3,5-bis(trifluoromethyl)phenyl)-1H-1,2,4-triazol-1-yl)-N-(4-methoxy-6-oxo-3,6-dihydropyridin-1(2H)-yl)acrylamide |

TABLE 1-continued

Compounds of the invention (1)

| Compound | Structure | Name |
|---|---|---|
| 88 | 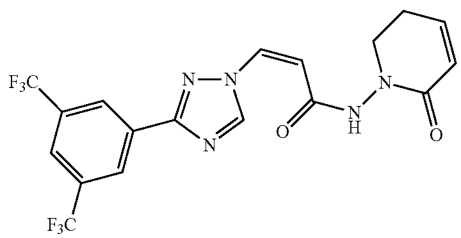 [SMILES: O=C(/C=C\n1cnc(-c2cc(C(F)(F)F)cc(C(F)(F)F)c2)n1)NN1CCC=CC1=O] | (Z)-3-(3-(3,5-bis(trifluoromethyl)phenyl)-1H-1,2,4-triazol-1-yl)-N-(6-oxo-3,6-dihydropyridin-1(2H)-yl)acrylamide |
| 89 | 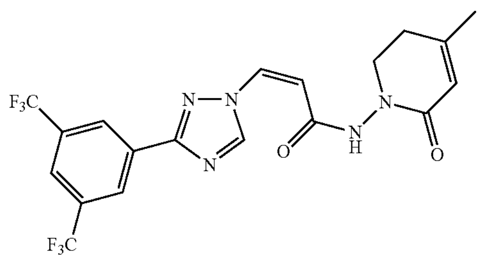 [SMILES: CC1=CC(=O)N(NC(=O)/C=C\n2cnc(-c3cc(C(F)(F)F)cc(C(F)(F)F)c3)n2)CC1] | (Z)-3-(3-(3,5-bis(trifluoromethyl)phenyl)-1H-1,2,4-triazol-1-yl)-N-(4-methyl-6-oxo-3,6-dihydropyridin-1(2H)-yl)acrylamide |
| 90 | 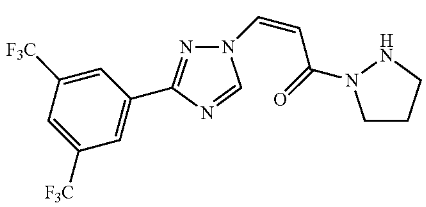 [SMILES: O=C(/C=C\n1cnc(-c2cc(C(F)(F)F)cc(C(F)(F)F)c2)n1)N1CCCN1] | (Z)-3-(3-(3,5-bis(trifluoromethyl)phenyl)-1H-1,2,4-triazol-1-yl)-1-(pyrazolidin-1-yl)prop-2-en-1-one |
| 91 | 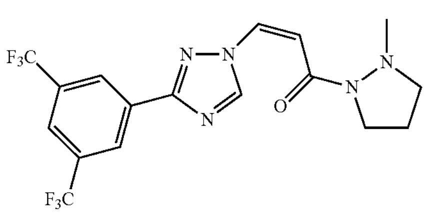 [SMILES: CN1CCCN1C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-1-(2-methylpyrazolidin-1-yl)prop-2-en-1-one |
| 92 | 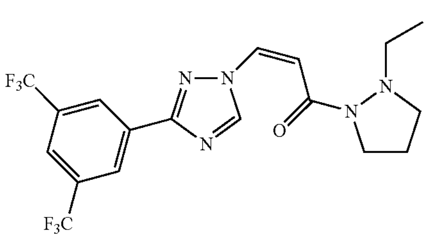 [SMILES: CCN1CCCN1C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-1-(2-ethylpyrazolidin-1-yl)prop-2-en-1-one |

TABLE 1-continued

Compounds of the invention

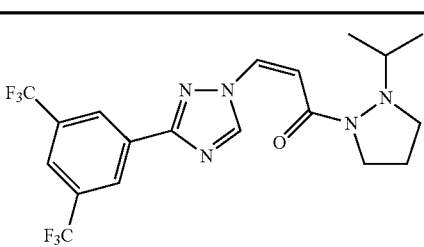

(1)

| Compound | Structure | Name |
|---|---|---|
| 93 | 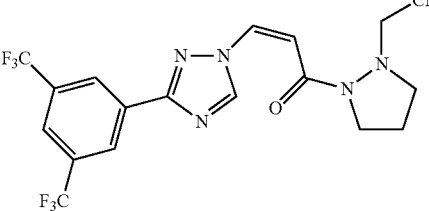 | (Z)-3-(3-(3,5-bis(trifluoromethyl)phenyl)-1H-1,2,4-triazol-1-yl)-1-(2-isopropylpyrazolidin-1-yl)prop-2-en-1-one |
| 94 | 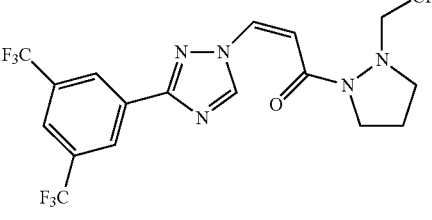 | (Z)-2-(2-(3-(3-(3,5-bis(trifluoromethyl)phenyl)-1H-1,2,4-triazol-1-yl)acryloyl)pyrazolidin-1-yl)acetonitrile |
| 95 | 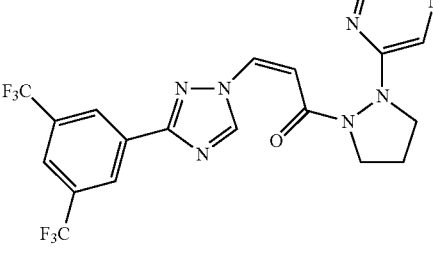 | (Z)-3-(3-(3,5-bis(trifluoromethyl)phenyl)-1H-1,2,4-triazol-1-yl)-1-(2-(2,2,2-trifluoroethyl)pyrazolidin-1-yl)prop-2-en-1-one |
| 96 | 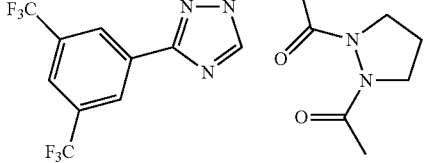 | (Z)-3-(3-(3,5-bis(trifluoromethyl)phenyl)-1H-1,2,4-triazol-1-yl)-1-(2-(pyrazin-2-yl)pyrazolidin-1-yl)prop-2-en-1-one |
| 97 | 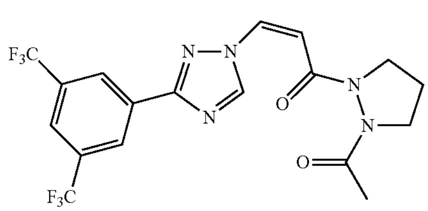 [SMILES: CC(=O)N1CCCN1C(=O)/C=C\n1cnc(-c2cc(C(F)(F)F)cc(C(F)(F)F)c2)n1] | (Z)-1-(2-acetylpyrazolidin-1-yl)-3-(3-(3,5-bis(trifluoromethyl)phenyl)-1H-1,2,4-triazol-1-yl)prop-2-en-1-one |

TABLE 1-continued

Compounds of the invention (1)

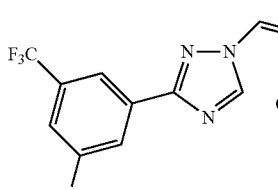

| Compound | Structure | Name |
|---|---|---|
| 98 | 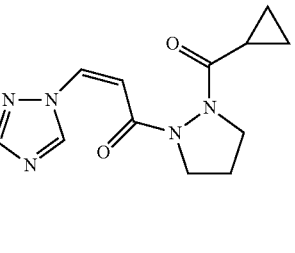 | (Z)-3-(3-(3,5-bis(trifluoromethyl)phenyl)-1H-1,2,4-triazol-1-yl)-1-(2-(cyclopropanecarbonyl)pyrazolidin-1-yl)prop-2-en-1-one |
| 99 | 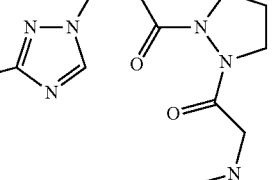 | (Z)-3-(3-(3,5-bis(trifluoromethyl)phenyl)-1H-1,2,4-triazol-1-yl)-1-(2-(dimethylglycyl)pyrazolidin-1-yl)prop-2-en-1-one |
| 100 | 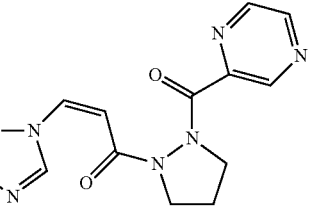 | (Z)-3-(3-(3,5-bis(trifluoromethyl)phenyl)-1H-1,2,4-triazol-1-yl)-1-(2-(pyrazine-2-carbonyl)pyrazolidin-1-yl)prop-2-en-1-one |
| 101 | 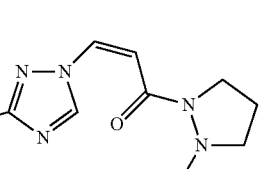 | (Z)-3-(3-(3,5-bis(trifluoromethyl)phenyl)-1H-1,2,4-triazol-1-yl)-1-(2-(2-chloronicotinoyl)pyrazolidin-1-yl)prop-2-en-1-one |
| 102 | 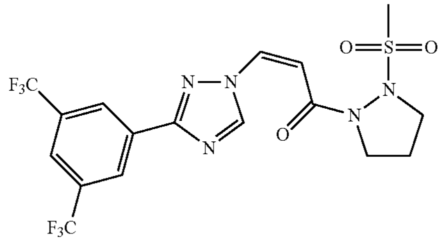 [SMILES: CS(=O)(=O)N1CCCN1C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-1-(2-(methylsulfonyl)pyrazolidin-1-yl)prop-2-en-1-one |

TABLE 1-continued

Compounds of the invention

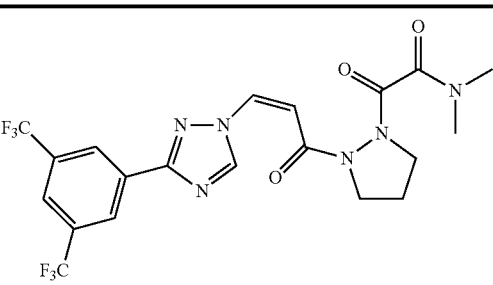

| Compound | Structure | Name |
|---|---|---|
| 103 | 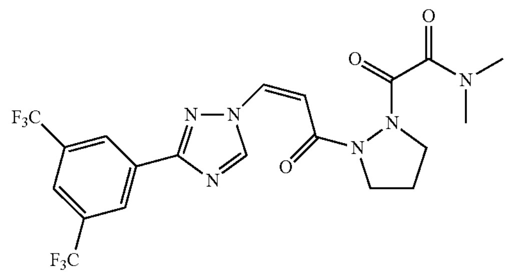 [SMILES: CN(C)C(=O)C(=O)N1CCCN1C(=O)/C=C\n1cnc(-c2cc(C(F)(F)F)cc(C(F)(F)F)c2)n1] | (Z)-2-(2-(3-(3-(3,5-bis(trifluoromethyl)phenyl)-1H-1,2,4-triazol-1-yl)acryloyl)pyrazoldin-1-yl)-N,N-dimethyl-2-oxoacetamide |

In another embodiment, the invention provides a combination pharmaceutical composition, which contains a pharmacologically acceptable excipient or carrier, and the compound of formula (1) of the present invention, an optical isomer, or a pharmaceutically acceptable inorganic or organic salt thereof, as an active ingredient.

In another embodiment, the invention provides the use of the compound, an optical isomer, or pharmaceutically acceptable inorganic or organic salts thereof, in the manufacture of anti-tumor drugs for treating diseases related to XPO1 protein.

It is to be understood that both the foregoing general description and the following detailed description of the invention are exemplary and explanatory, and it is intended to provide further explanations of the invention as claimed.

BRIEF DESCRIPTION OF DRAWINGS

In order to more dearly illustrate the technical scheme in the technical embodiment of the present invention, the drawings required for the technical description of the embodiments are briefly introduced below. Tt is obvious that the drawings in the following description are only some embodiments of the present invention.

DETAILED DESCRIPTION OF THE ILLUSTRATED EMBODIMENTS

Figure 1:
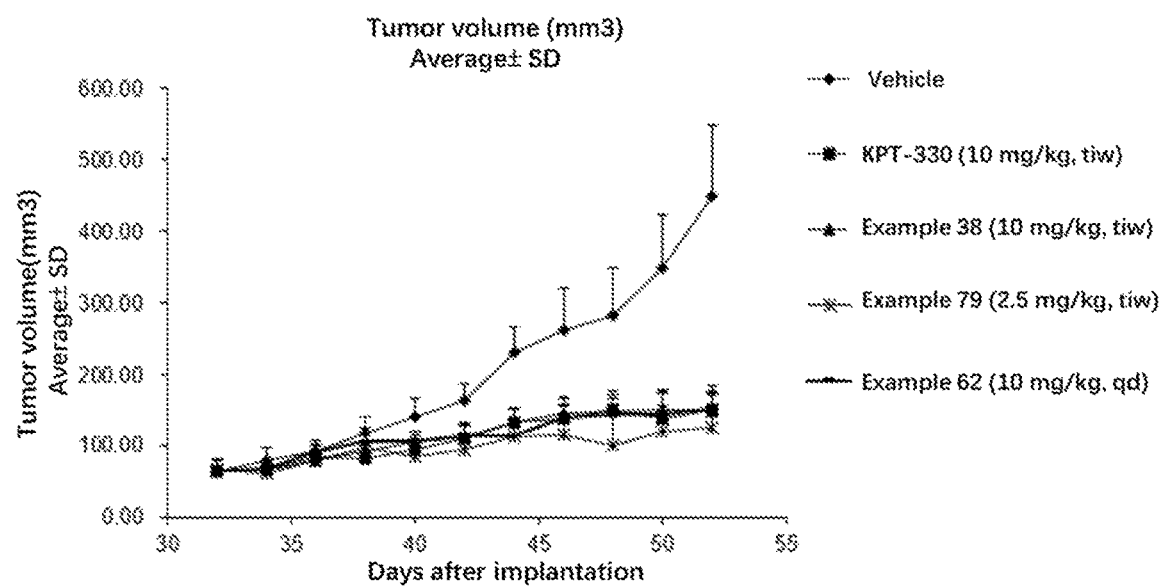
FIG. 1 is a graph of the tumor growth inhibitory effect of vehicle control, KPT-330, compounds 38, 79 and 62 in BxPC-3 xenografts.

The preparation methods of the compounds of the general formula (1) are described specifically in following part, but these specific methods do not constitute any limitations of the present invention.

The compound of formula (1) described above may be synthesized using standard synthesis techniques, well-known techniques or combination of methods herein. In addition, the solvents, temperatures and other reaction conditions mentioned herein may vary. Stating materials for the synthesis of the compounds of formula (1) may be synthesized or obtained from commercial sources such as, but not limited to, Aldrich Chemical Co. (Milwaukee, Wis.) or Sigma Chemical Co. (St. Louis, Mo.). The compounds described herein and other related compounds having different substituents may be synthesized using well-known techniques and starting materials, including those found in March, ADVANCED ORGANIC CHEMISTRY 4th Ed. (Wiley 1992); Carey and Sundberg, ADVANCED ORGANIC CHEMISTRY 4th Ed., Vols. A and B (Plenum 2000, 2001), Green and Wuts, PROTECTIVE GROUPS IN ORGANIC SYNTHESIS $3^{rd}$ Ed., (Wiley 1999). The general methods for the preparation of the compounds can be varied by using suitable reagents and conditions for introducing different groups in the molecular formulas provided herein.

In one aspect, the compounds described herein are obtained according to the well-known methods. However, the conditions of the process such as reactants, solvents, bases, amounts of compound used, reaction temperatures, time required for the reactions, and the like are not limited to the following explanations. The compounds of the invention may also be conveniently prepared, optionally in combination with various synthetic methods described in this specification or well-known methods, such combinations being readily carried out by those skilled in the art. On the other aspect, the invention also provides the preparation methods of the compounds shown in the general formula (1), which are prepared by the following method A, method B or method C:

Method A contains the following step: starting materials 1-1 and 1-2 were carried out condensation reaction in the presence of a condensation agent and a base to give the compound of formula (1A).

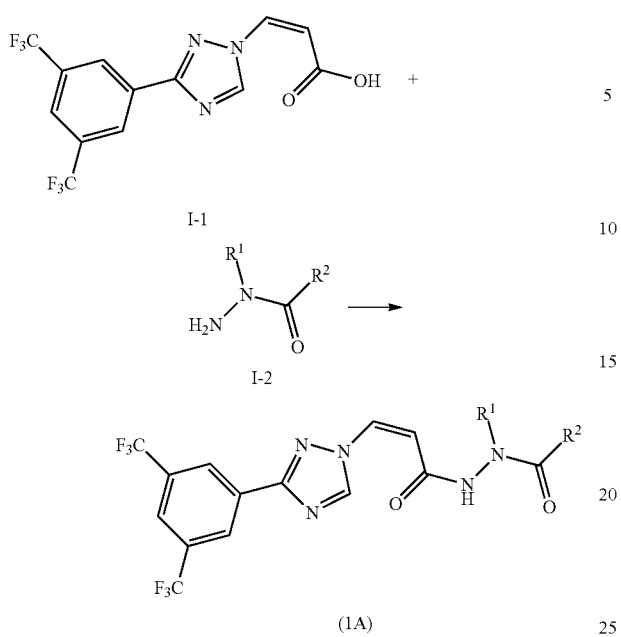

(1A)

In the above reaction, R¹ and R² have the same definitions as defined above.

Method B contains the following step: starting materials I-1 and II-1 were carried out condensation reaction in the presence of a condensation agent and a base to give the compound of formula (1B).

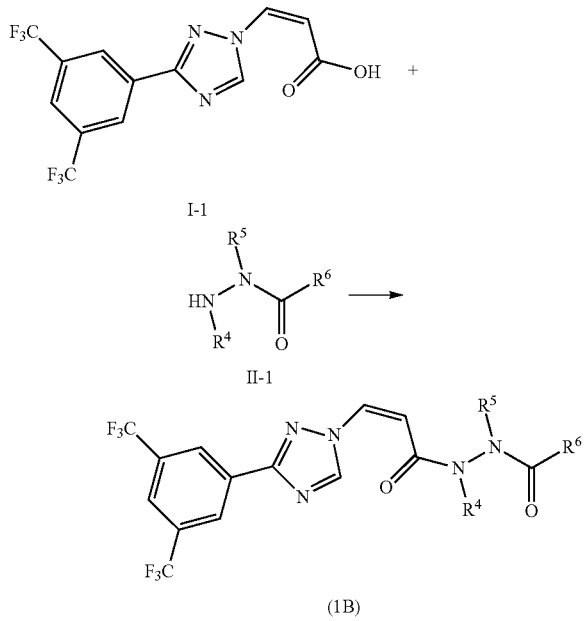

(1B)

In the above reaction, R⁴, R⁵ and R⁶ have the same definitions as defined above.

Method B contains the following step: starting materials I-1 and III-1 were carried out condensation reaction in the presence of a condensation agent and a base to give the compound of formula (1C).

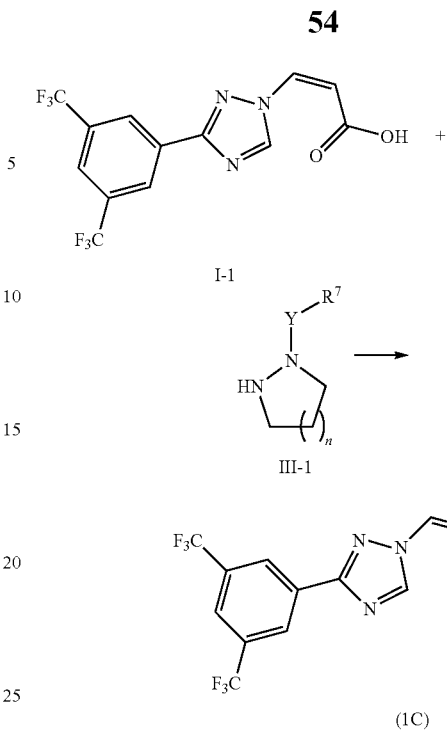

(1C)

In the above reaction, n, Y and R⁷ have the same definitions as defined above.

Further Forms of the Compounds

In some embodiments, the compounds of formula (1) are prepared as a pharmaceutically acceptable acid addition salt (a pharmaceutically acceptable salt) by reacting the free base of the compound with a pharmaceutically acceptable inorganic, organic or acidic amino acid, which including but not limited to, inorganic acids such as hydrochloric acid, hydrobromic acid, hydrofluoric acid, sulfuric acid, nitric acid and phosphoric acid; Organic acid such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, p-toluenesulfonic acid, ethanesulfonic acid and benzenesulfonic acid, Acidic amino acid such as aspartic acid and glutamic acid.

The term "pharmaceutically acceptable" herein represent a relatively non-toxic substance, such as a carrier or diluent, that does not inactivate the biological activities or properties of the invented compounds, e. g., administration of the substance to a subject does not cause unwanted biological effect or detrimental interactions with any of its contained components.

The term "pharmaceutically acceptable salt" refers to a form of a compound that does not cause significant irritation to the administered subject and does not eliminate the biological activities and properties of the compound. In certain aspects, pharmaceutically acceptable salts are obtained by reacting a compound of formula (1) with an acid such as an inorganic acid, such as hydrochloric acid, hydrobromic acid, hydrofluoric acid, sulfuric acid, phosphoric acid or nitric acid, organic acid such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid or p-toluenesulfonic acid, and acidic amino acids such as aspartic acid or glutamic acid.

It should be understood that pharmaceutically acceptable salts include solvent addition forms or crystalline forms, especially solvates or polymorphs. Solvates contain stoichiometric or non-stoichiometric solvents and are selectively formed during crystallization with pharmaceutically acceptable solvents such as water and ethanol. Hydrates are formed when the solvent is water, or alcoholates are formed when the solvent is ethanol. The solvates of the compound of formula (1) can be conveniently prepared or formed according to the method described herein. For example, the hydrate of the compound of formula (1) is conveniently prepared by recrystallization from a mixed solvent of water/organic solvent, and the organic solvent used includes but is not limited to dioxane, tetrahydrofuran, ethanol or methanol. In addition, the compounds mentioned here can exist in non-solvated or solvated forms. In summary, for the purposes of the compounds and methods provided herein, the solvated forms are considered to be equivalent to the non-solvated forms.

In other specific embodiments, the compounds of formula (1) are prepared in different forms, including but not limited to amorphous, pulverized and nano-particle size forms. In addition, the compounds of formula (1) include crystalline forms and polymorphic forms. Polymorphic forms include different lattice arrangements of the same element composition of the compounds. Polymorphs usually have different X-ray diffraction patterns, infrared spectra, melting points, density, hardness, crystalline forms, optical and electrical properties, stability and solubility. Different factors, such as recrystallization solvent, crystallization rate and storage temperature, may cause specific crystalline formed dominantly.

On the other aspect, the compounds of formula (1) have one or more stereocenters, and thus appear in the forms of racemate, racemic mixture, single enantiomer, diastereomer compound and single diastereomer. The asymmetric centers that can exist depend on the properties of various substituents on the molecule. Each such asymmetric center will independently produce two optical isomers, and all possible optical isomers and diastereomer mixtures and pure or partially pure compounds are included in the scope of the present invention. The present invention is meant to include all such isomeric forms of these compounds.

Terminology

Unless otherwise stated, the terms used in this application, including the specifications and claims, are defined as follows. It must be noted that in the specifications and the appended claims, the singular forms "a" and "an" include plural meanings unless otherwise clearly indicated in the context. Unless otherwise stated, conventional methods such as mass spectrometry, nuclear magnetic resonance, HPLC, protein chemistry, biochemistry, recombinant DNA technology and pharmacology were used. In this application, "or" or "and" means "and/or" unless otherwise stated.

"Compound of formula (1)" refers to a compound of structure of formula (1).

"Alkyl" refers to a saturated aliphatic hydrocarbon group, including straight-chain and branched-chain groups with 1 to 6 carbon atoms, preferably a lower alkyl groups containing 1 to 4 carbon atoms, such as methyl, ethyl, propyl, 2-propyl, n-butyl, isobutyl or tert-butyl. As used herein, "alkyl" includes unsubstituted and substituted alkyl, especially alkyl substituted by one or more halogens. Preferred alkyl groups are selected from $CH_3$, $CH_3CH_2$, $CF_3$, $CHF_2$, $CF_3CH_2$, $^iPr$, $^nPr$, $^iBu$, $^cPr$, $^nBu$ or $^tBu$.

"Cycloalkyl" refers to a non-aromatic monocyclic or multicyclic aliphatic hydrocarbon group having 3-6 carbon atoms, in which one or more rings may contain one or more double bonds, but none of the rings has a completely conjugated π electronic system. For example, cyclopropyl, cyclobutyl, cyclopentyl, cyclohexane, cyclohexadiene and the like.

"Alkoxy" refers to an alkyl group bonded to the rest of the molecule through an ether oxygen atom. Typical alkoxy groups are alkoxy groups having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, especially alkoxy substituted by one or more halogens. Preferred alkoxy groups are selected from $OCH_3$, $OCF_3$, $CHF_2O$, $CF_3CH_2O$, $^iPrO$, $^nPrO$, $^iBuO$, $^cPrO$, $^nBuO$ or $^tBuO$.

"aryl" refers to a group with at least one aromatic ring structure, i.e., carbocyclic aryl with conjugated π electron system, such as benzyl and naphthyl.

"Heteroaryl" refers to an aromatic group containing one or more heteroatoms (O, S or N). Heteroaryl is monocyclic or polycyclic, for example, a monocyclic heteroaryl ring is fused with one or more carbocyclic aromatic groups or other monocyclic heterocyclic groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, tetrazolyl, furyl, thienyl, isoxazolyl, thiazolyl, oxazolyl, isothiazolyl, pyrrolyl, indolyl, benzimidazolyl, benzofuran, benzothiazolyl, benzothiophenyl, benzoxazolyl, benzopyridyl and pyrrolopyrimidyl.

"Alkenyl" refers to a saturated linear or branched non-cyclic alkyl group with 2 to 12 carbon atoms and at least one carbon-carbon double bond contained.

"Halogen" (or "halo") refers to fluorine, chlorine, bromine or iodine.

"Oxo" means "=O."

"Deuteration" (or "deuterated") means that all or part of H atoms on substituents are replaced by D.

The term "bond" or "single bond" refers to a chemical bond between two atoms or two fragments (when atoms connected by bonds are considered to be put of a large structure). On the one hand, when the group described here is a bond, the reference group is absent, allowing a bond to be formed between the remaining definite groups.

The term "ring" includes any ring structures. The tem "member" is meant to indicate the number of skeleton atoms constituting a ring. Thus, for example, cyclohexyl, pyridyl, pyranyl and thiopyranyl are six-membered rings, while cyclopentyl, pyrrolyl, furanyl and thienyl are five-membered rings.

The term "fragment" refers to a specific part or functional group of a molecule. Chemical fragments are generally considered as chemical entities contained in or attached to molecules.

Specific Pharmaceutical and Medical Terms

The term "acceptable," as used herein, means that a prescription component or active ingredient does not have excessively harmful effects on the health of subject.

As used herein, the term "treatment," "course of treatment" or "therapy" includes alleviating, inhibiting or improving symptoms or conditions of diseases; Inhibiting the occurrence of complications; Improving or preventing potential metabolic syndrome; Suppressing the occurrence of diseases or symptoms, such as controlling the development of diseases or conditions; Alleviating diseases or symptoms; Reducing disease or symptoms; Alleviating complications caused by diseases or symptoms, or preventing or treating symptoms caused by diseases or symptoms.

As used herein, a certain compound or pharmaceutical composition, which can improve a certain disease, symptom or condition after administration, especially reduce its severity, delay the onset, slow down the progress of the disease, or shorten the duration of the disease. Whether fixed administration or temporary administration, continuous administration or intermittent administration, which can be attributed to related administration.

The term "active ingredient" refers to the compounds represented by the general formula (1) and the pharmaceutically acceptable inorganic or organic salts of the compounds of the general formula (1). Compounds of the present invention may contain one or more asymmetric centers, and thus appear in the form of racemates, racemic mixtures, single enantiomers, diastereomeric compounds or single diastereomers. The asymmetric centers that can exist depend on the properties of various substituents on the molecule. Each such asymmetric center will independently produce two optical isomers, and all possible optical isomers, diastereomer mixtures and pure or partially pure compounds are included in the scope of the present invention. The present invention is meant to include all such isomeric forms of these compounds.

The compounds shown in the general formula (1) are cis acrylamide, and for convenience, the compounds of the general formula (1) in this application are simply called acrylamide.

In addition, As needed, the compounds of the invention can be prepared by reacting with pharmaceutically acceptable acids in polar protic solvents, such as methanol, ethanol and isopropanol, to generate pharmaceutically acceptable salts. The pharmaceutically acceptable inorganic or organic acids can be selected from hydrochloric acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, p-toluenesulfonic acid, aspartic acid, or glutamic acid and the like.

Words such as "compound," "composition," "agent" or "medicine or medicine" can be used interchangeably here, and all refer to a compound or composition which can induce the desired pharmaceutical and/or physiological response through local and/or systemic action when applied to a person (human or animal).

The word "administered, administering or administration" here refers to the direct administration of the compounds or compositions, or the administration of prodrugs, derivatives or analogs of the active compounds, which can form a considerable amount of the active compounds in the body of the subject.

The terms "subject" or "patient" are used interchangeably herein to refer to an animal (including a human) that is amenable to treatment by the compounds and/or methods. The term "individual" or "patient" herein encompasses both male and female sexes unless otherwise specified. Thus "individual" or "patient" includes any mammal, including, but not limited to, human, non-human primates such as mammals, dogs, cats, horses, sheep, pigs, cattle, and the like, that may benefit from treatment with the compounds. Animals suitable for treatment with compounds and/or method of that invention are preferably humans. In general, the term "patient" and the term "individual" may be used interchangeably herein.

Although the numerical ranges and parameters used to define the wide range of the present invention are approximate values, the relevant values in the specific embodiments have been presented here as accurately as possible. However, any numerical value inevitably contains standard deviation caused by individual test methods. Here, "about" usually means that the actual value is within plus or minus 10%, 5%, 1% or 0.5% of a specific value or range. Alternatively, the word "about" means that the actual value falls within the acceptable standard error of the average value, depending on the consideration of those skilled in the art. Except for experimental examples, or unless otherwise specified, it is understood that all ranges, quantities, values and percentages used herein (for example, to describe the amount of materials, the length of time, the temperatures, the operating conditions, the proportions of quantities and other similar ones) are modified by "about". Therefore, unless otherwise stated, the numerical parameters disclosed in this specification and the appended claims are approximate values, and can be changed as required. At least these numerical parameters should be understood as the indicated effective digits and the numerical values obtained by applying the general carry method.

Unless otherwise defined in this specification, the meanings of scientific and technical terms used herein are the same as those understood and used by those skilled in the art. In addition, the singular noun used in this specification covers the plural form of the noun without conflict with the context; The plural nouns used also cover the singular form of the noun.

Therapeutic Use

Compounds or compositions described herein can generally be used to inhibit CRM1, and thus can be used to treat one or more diseases related to CRM1 protein. Therefore, in certain embodiments, the present invention provides a method for treating a CRM1-mediated disease, comprising the step of administering a compound of the present invention, or a pharmaceutically acceptable composition thereof, to a patient in need thereof.

As used herein, the term "CRM1 mediated" disease refers to any disease or other harmful condition in which CRM1 protein is known to play a role. Therefore, another embodiment of the present invention relates to treating or reducing the severity of one or more diseases in which CRM1 protein is known to play a role. In certain embodiments, the present invention provides a method for treating diseases related to the expression or activity of P53, P21, Rb1, APC, c-ABL, FOXO, IκB, NF-κB, COX-2 or HDAC in a subject, which comprises administering a therapeutically effective amount of a compound of the present invention to the patient. In another embodiment, the present invention relates to a method of treating or reducing the severity of a disease or condition selected from proliferative diseases (e.g., cancer), inflammatory disorders, autoimmune diseases, viral infections or neurodegenerative disorders, wherein the method comprises administering a compound or composition of the present invention to a patient in need thereof. In a more specific embodiment, the present invention relates to a method of treating cancer or reducing its severity.

Cancers that can be treated with the compounds of the present invention include, but are not limited to, hematological malignancies (leukemia, lymphoma, myeloma including multiple myeloma, myelodysplastic syndrome or myelodysplastic syndrome) and solid tumors (cancers such as prostate, breast, lung, colon, pancreas, kidney, ovary, soft tissue cancer and osteosarcoma or stromal tumors).

Route of Administration

The compound of the present invention and its pharmaceutically acceptable salts can be made into various preparations, which contain the compound of the present invention or its pharmaceutically acceptable salts and pharmaceutically acceptable excipients or carriers in a safe and effective amount range. Among them, "safe and effective amount" means that the amount of the compound is capable of obviously improving the condition without causing serious side effects. The safe and effective dose of the compound is determined according to the age, illness, course of treatment and other specific conditions of the subject.

"Pharmaceutically acceptable excipient or carrier" refers to one or more compatible solid or liquid fillers or gel substances, which are suitable for human use and must have sufficient purity and low toxicity. "Compatibility" here means that each component in the composition can be mixed with the compounds of the present invention and between them, without significantly reducing the efficacy of the compound. Examples of pharmaceutically acceptable excipients or carriers include cellulose and its derivatives (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween) wetting agent (such as sodium dodecyl sulfate), coloring agent, flavoring agent, stabilizer, antioxidant, preservative, pyrogen-free water, etc.

The compounds of the present invention can be administered orally, rectally, parenterally (intravenously, intramuscularly or subcutaneously) or topically.

Solid dosage forms for oral administration include capsules, tablets, pills, powders and granules. In these solid dosage forms, that active compound is mixed with at least one conventional inert excipient (or carry), such as sodium citrate or dicalcium phosphate, or with: (a) a filler or compatibilizer, such as starch, lactose, sucrose, glucose, mannitol, and silicic acid; (b) binders such as hydroxymethyl cellulose, alginates, gelatin, polyvinyl pyrrolidone, sucrose and acacia; (c) humectant, such as glycerol; (d) disintegrant such as agar, calcium carbonate, potato or tapioca starch, alginic acid, certain complex silicates, and sodium carbonate; (e) slow solvents, such as paraffin; (f) an absorption accelerator, such as a quaternary amine compound; (g) wetting agents, such as cetyl alcohol and glyceryl monostearate; (h) adsorbent, such as kaolin; And (i) a lubricant such as talc, calcium stearate, magnesium stearate, solid polyethylene glycol, sodium lauryl sulfate, or mixtures thereof. In capsule, tablets and pill, the dosage form may also contain a buffer.

Solid dosage forms such as tablets, sugar pills, capsules, pills and granules may be prepared using coatings and shell materials such as casings and other materials well-known in the art. They may comprise an opacifying agent and the release of the active compound or compound in such a composition may be released in a delayed manner in a portion of the digestive tract. Examples of embedding components that may be used are polymeric substances and waxes. If desired, the active compound may also form microcapsules with one or more of the above excipients.

Liquid dosage forms for oral administration include pharmaceutically acceptable emulsions, solutions, suspensions, syrups or tinctures. In addition to the active compound, the liquid dosage form may comprise inert diluents conventionally used in the art, such as water or other solvents, solubilizers and emulsifiers, for example ethanol, isopropanol, ethyl carbonate, ethyl acetate, propylene glycol, 1,3-butanediol, dimethylformamide and oils, particularly cottonseed oil, peanut oil, corn germ oil, olive oil, castor oil, sesame oil or mixtures of these and the like.

In addition to these inert diluents, the composition may also contain adjuvants such as wetting agents, emulsifiers and suspending agents, sweeteners, flavoring agents and flavorants.

In addition to the active compounds, the suspension may comprise suspending agents such as ethoxylated isostearyl alcohol, polyoxyethylene sorbitol and sorbitan esters, microcrystalline cellulose, aluminum methoxide, agar or mixtures of these and the like.

The composition for parenteral injection may comprise a physiologically acceptable sterile aqueous or non-aqueous solution, dispersion, suspension or emulsion, and a sterile powder for reconstitution into a sterile injectable solution or dispersion. Suitable aqueous and non-aqueous carriers, diluents, solvents or excipients include water, ethanol, polyols and suitable mixtures thereof.

Dosage forms of the compounds of the invention for topical administration include ointments, powders, patches, sprays and inhalants. The active ingredient is mixed under sterile conditions with a physiologically acceptable carrier and any preservatives, buffers, or propellants as may be required.

The compound of the invention may be administered alone or in combination with other pharmaceutically acceptable compounds.

When a pharmaceutical composition is used, a safe and effective amount of a compound of the invention is applied to a mammal (e.g., a human) in need of treatment, wherein the dose at the time of administration is a pharmaceutically acceptable effective dose, and for a human of 60 kg body weight, the daily dose is generally 1 to 1000 mg, preferably 10 to 500 mg. Of course, specific dose should also take into account factors such as route of administration, patient health, etc., which are within the skill of a skilled physician.

The above features mentioned in the present invention, or the features mentioned in the embodiments, may be combined at random. All of the features disclosed in this specification may be used in any composition form and the various features disclosed in the specification may be replaced with any alternative feature that provides the same, equivalent, or similar purpose. Thus, unless otherwise specified, the disclosed features are merely generic examples of equivalent or similar features.

Various specific aspects, features and advantages of the above compounds, methods, and pharmaceutical compositions will be set forth in detail as following. It is to be understood that the following detailed description and examples describe specific embodiments for reference only. Various changes or modifications may occur to those skilled in the art after reading the description of the invention, and such equivalents fall within the scope of the application.

In all example, $^1$H-NMR was recorded with a Varian Mercury 400 NMR spectrometer and that chemical shift was expressed as δ (ppm); Silica gel for separation is 200-300 mesh without specific statement, and the ratio of eluents is volume ratio.

Abbreviations of the invention are as following: $CDCl_3$ represents deuterated chloroform; $CD_3OD$ represents deuterated methanol; DABCO represents 1,4-diazabicyclo[2.2.2]octane; DCM represents dichloromethane; DIPEA represents diisopropylethylamine; DMF represents dimethylformamide; DMSO represents dimethyl sulfoxide; EA represents ethyl acetate; h represents hour; LiOH represents lithium hydroxide; MgCl$_2$ represents magnesium chloride; mins represents minutes; MS represents mass spectrum; NaSH represents sodium hydrosulfide; NMR represents nuclear magnetic resonance; T$_3$P represents propyl phosphoric anhydride; THF represents tetrahydrofuran.

Through extensive research, the inventors have synthesized and evaluated a large number of compounds and found for the first time that the compounds of formula (1) have strong antitumor activity, good water solubility, more excellent pharmacokinetic properties and in vivo antitumor activity. Thus, the present invention was completed by the inventors.

Preparation Example 1: Synthesis of (Z)-3-(3-(3,5-bis(trifluoromethyl)phenyl)-1H-1,2,4-triazol-1-yl) acrylic Acid (I-1)

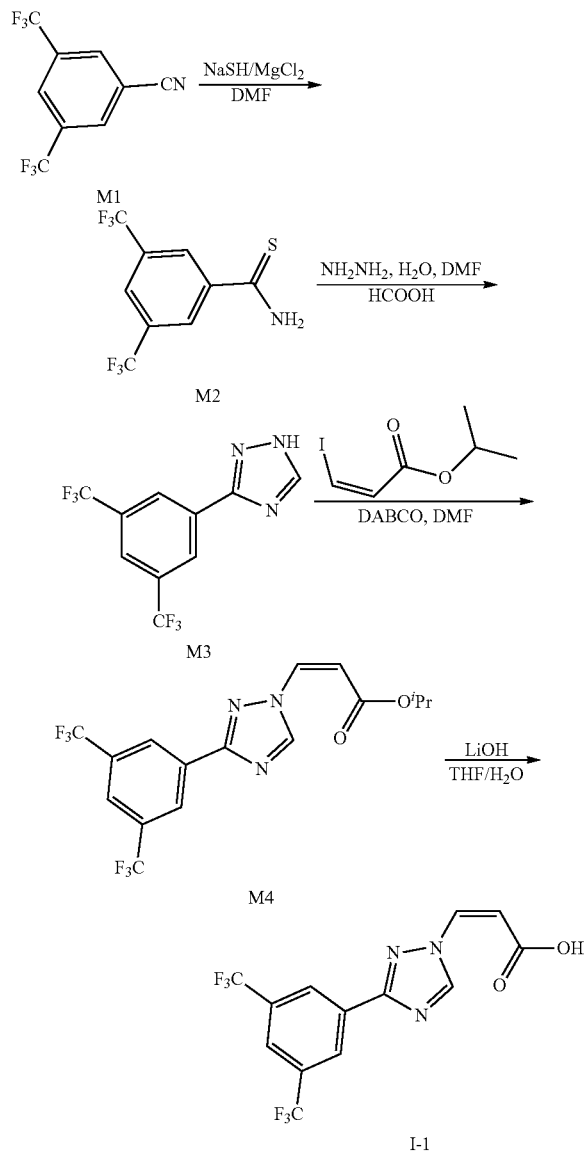

Synthesis of 3,5-bis(trifluormethyl)benzothioamide (M2)

3,5-bis(trifluoromethyl)benzonitrile (47.82 g, 0.2 mol) was dissolved in DMF (250 mL), NaSH (22.42 g, 2.0 eq) and MgCl$_2$ (38.08 g, 2.0 eq) were added, after stirring at room temperature for 3 h, the mixture was poured into ice-water (2 L), extracted with EA(250 mL*3), combined the organic layers, dried with anhydrous sodium sulfate, filtered and concentrated under reduced pressure. Finally, the crude product of 3,5-bis(trifluoromethyl)thiobenzamide (46.97 g, yield 86%) was obtained.

Synthesis of 3-(3,5-bis(trifluoromethyl)phenyl)-1H-1,2,4-triazole (M3)

3,5-Bis(trifluoromethyl)thiobenzamide (46.44 g, 0.17 mol) was dissolved in DMF (250 mL) and hydrazine hydrate (16.5 mL, 2.0 eq) was added dropwise. After the addition, the mixture was stirred at room temperature for 1 h, followed by the dropwise addition of HCOOH (200 mL). Then the mixture was heated to 90° C. to react for 3 h. After cooling to room temperature, the mixture was poured into saturated aqueous NaHCO$_3$ solution (1.2 L) and extracted with EA (300 mL*3). The combined organic layers were washed with saturated aqueous sodium chloride solution (100 mL*2), dried with anhydrous sodium sulfate, filtered and concentrated under reduced pressure to obtain a crude product, which was further slurried with petroleum ether (400 mL), filtered and dried to obtain the target compound 3-(3,5-bis(trifluoromethyl)phenyl)-1H-1,2,4-triazole (34.40 g, yield: 72%), MS(ESI, m/z): 282.1 [M+H]$^+$.

Synthesis of isopropyl (Z)-3-(3-(3,5-bis(trifluoromethyl)phenyl)-1H-1,2,4-triazol-1-yl)acrylate (M4)

3-(3,5-bis(trifluoromethyl)phenyl)-1H-1,2,4-triazole (33.74 g, 0.12 mol) was dissolved in DMF (150 mL), DABCO (26.92 g, 2.0 eq) was added. After stirring at room temperature for 30 mins, cooled to 0° C., and (Z)-3-isopropyl iodide (31.68 g, 1.1 eq) was added dropwise, then the mixture reacted at room temperature for 1 h. The mixture was poured into ice-water (1 L), extracted with EA (200 mL*3), the organic layers were combined, washed with saturated aqueous sodium chloride solution (50 mL*2), dried with anhydrous sodium sulfate, filtered and concentrated under reduced pressure to give the crude product of (Z)-3-(3-(3,5-bis(trifluoromethyl)phenyl)-1H-1,2,4-triazol-1-yl) isopropyl acrylate (28.32 g, yield 60%).

Synthesis of (Z)-3-(3-(3,5-bis(trifluoromethyl)phenyl)-1H-1,2,4-triazol-1-yl)acrylic Acid (I-1)

Isopropyl (Z)-3-(3-(3,5-bis(trifluoromethyl)phenyl)-1H-1,2,4-triazol-1-yl)acrylate (27.53 g, 70 mmol) was dissolve in THF, and a solution of LiOH (8.4 g, 5.0 eq. 200 mL in water) was added dropwise to the reaction solution, followed by stirring at room temperature for 4 h, an ice-water mixture (100 mL) was added to the reaction. The pH value was adjusted to 2-3 with dilute hydrochloric acid, extracted with EA (200 mL*3), the organic layers were combined, dried with anhydrous sodium sulfate, filtered and concentrated under reduced pressure to give desired product (Z)-3-(3-(3,5-bis(trifluoromethyl)phenyl)-1H-1,2,4-triazol-1-yl) acrylic acid (23.36 g, yield 95%).

¹H NMR (400 MHz, CD₃OD): δ 9.54 (s, 1H), 8.63-8.56 (m, 2H), 8.04 (tt, J=1.6, 0.9 Hz, 1H), 7.42 (d, J=10.6 Hz, 1H), 5.90 (d, J=10.6 Hz, 1H); MS (ESI, m/z): 352.1 [M+H]⁺.

Example 1 Synthesis of (Z)-3-(3-(3,5-bis(trifluoromethyl)phenyl)-1H-1,2,4-triazol-1-yl)-N-(2-oxoazetidin-1-yl)acrylamide (Compound 1)

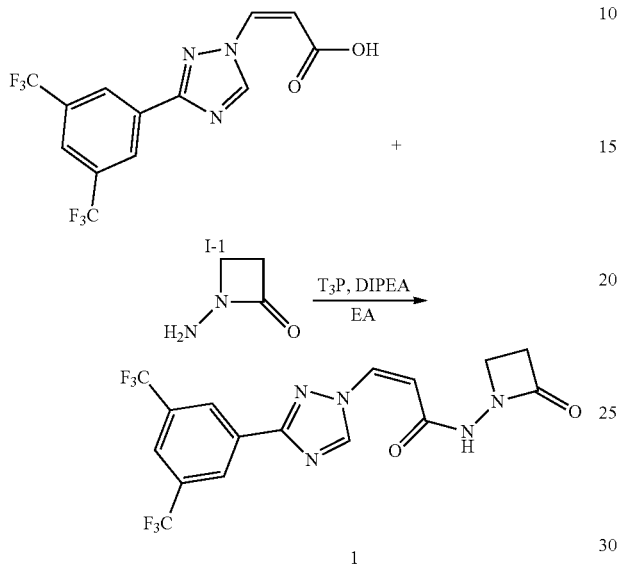

(Z)-3-(3-(3,5-bis(trifluoromethyl)phenyl)-1H-1,2,4-triazol-1-yl)acrylic acid (105 mg, 0.3 mol) and 1-aminoazacyclobutyl-2-one (39 mg, 0.45 mmol) were dissolved in dried EA (10 mL), protected with nitrogen gas and cooled to −60° C. T₃P (0.3 mL, 2 M of EA solution) was added dropwise. Then DIPEA (77 mg, 0.6 mmd) was added and the reaction was continued with stirring for 3 h. the reaction was quenched with a little ice water, washed with water (20 mL), the aqueous phase was extracted with EA (20 mL*2), the organic layers were combined, washed with saturated sodium chloride solution (20 mL), dried with anhydrous sodium sulfate, concentrated under reduced pressure and further purified by column chromatography (DCM/MeOH=1/100 to 1/30) to offer the desired product (Z)-3-(3-(3,5-bis(trifluoromethyl)phenyl)-1H-1,2,4-triazol-1-yl)-N-(2-oxoazacyclobutyl-1-yl)acrylamide (15.1 mg, yield 12%).

¹H NMR (400 MHz, DMSO-d₆): δ 10.70 (s, 1H), 9.39 (s, 1H), 8.56 (s, 2H), 8.28 (s, 1H), 7.52 (d, J=10.8 Hz, 1H), 5.95 (d, J=10.6 Hz, 1H), 3.52 (t, J=4.4 Hz, 2H), 2.91 (t, J=4.2 Hz, 2H); MS (ESI, m/z): 352.1 [M+H]⁺.

Example 2 to Example 9: Synthesis of Compound 2 to Compound 89

Compounds 2-89 were synthesized by using I-1 as starting material, and reacting with different hydrazides, which are similar to the synthesis of compound 1.

TABLE 2

| Mass and NMR data of compounds 2-89 | | |
|---|---|---|
| Compound | MS (ESI, m/z) | ¹H NMR data |
| 2 | 434.1 [M + H]⁺ | ¹H NMR (400 MHz, DMSO-d₆): δ 10.59 (s, 1H), 9.46 (s, 1H), 8.55 (s, 1H), 8.29 (s, 2H), 7.51 (d, J = 10.4 Hz, 1H), 6.01 (d, J = 10.3 Hz, 1H), 3.53 (t, J = 6.8 Hz, 2H), 2.33 (t, J = 7.9 Hz, 2H), 2.03 (t, J = 7.5 Hz, 2H) |
| 3 | 448.1 [M + H]⁺ | ¹H NMR (400 MHz, DMSO-d₆): δ 10.62 (s, 1H), 9.50 (s, 1H), 8.54 (s, 2H), 8.28 (s, 1H), 7.49 (d, J = 10.4 Hz, 1H), 6.01 (d, J = 10.4 Hz, 1H), 3.49 (t, J = 6.0 Hz, 2H), 3.11 (dt, J = 7.0, 3.4 Hz, 2H), 2.38 (t, J = 6.4 Hz, 2H), 2.11 (t, J = 6.4 Hz, 2H) |
| 4 | 462.1 [M + H]⁺ | ¹HNMR (400 MHz, DMSO-d₆): δ 10.69 (s, 1H), 9.49 (s, 1H), 8.53 (s, 2H), 8.27 (s, 1H), 7.47 (d, J = 10.3 Hz, 1H), 5.99 (d, J = 10.4 Hz, 1H), 3.62 (m, 2H), 2.51 (m, 2H), 1.72-1.58 (m, 6H) |
| 5 | 460.1 [M + H]⁺ | ¹H NMR (400 MHz, CD₃OD): δ 9.43 (s, 1H), 8.62 (d, J = 1.7 Hz, 2H), 8.06 (s, 1H), 7.44 (d, J = 10.5 Hz, 1H), 5.97 (d, J = 10.5 Hz, 1H), 4.58 (s, 1H), 4.08 (d, J = 2.1 Hz, 2H), 2.03 (d, J = 1.4 Hz, 3H), 1.81 (dt, J = 2.6, 1.1 Hz, 3H) |
| 6 | 474.1 [M + H]⁺ | ¹H NMR (400 MHz, CDCl₃): δ 9.76 (s, 1H), 9.68 (s, 1H), 8.40 (s, 2H), 7.79 (s, 1H), 7.09 (d, J = 11.0 Hz, 1H), 5.78 (d, J = 11.0 Hz, 1H), 4.11 (s, 2H), 2.34 (q, J = 7.5 Hz, 2H), 2.04 (s, 3H), 1.11 (t, J = 7.5 Hz, 3H) |
| 7 | 460.1 [M + H]⁺ | ¹H NMR (400 MHz, DMSO-d₆): δ 11.30 (s, 1H), 9.36 (s, 1H), 8.54 (s, 2H), 8.21 (s, 1H), 7.57 (d, J = 10.4 Hz, 1H), 6.81 (d, J = 2.1 Hz, 2H), 6.15 (d, J = 10.4 Hz, 1H), 2.03 (d, J = 1.9 Hz, 3H) |
| 8 | 474.1 [M + H]⁺ | ¹H NMR (400 MHz, CDCl₃): δ 9.36 (s, 1H), 8.55 (d, J = 1.7 Hz, 2H), 8.51 (s, 1H), 7.90 (s, 1H), 7.27 (d, J = 11.1 Hz, 1H), 5.77 (d, J = 11.0 Hz, 1H), 2.05 (d, J = 0.8 Hz, 6H) |
| 9 | 448.1 [M + H]⁺ | ¹H NMR (400 MHz, CDCl₃): δ 9.81 (s, 1H), 9.75 (s, 1H), 8.38 (s, 2H), 7.77 (s, 1H), 7.06 (d, J = 11.1 Hz, 1H), 5.69 (d, J = 11.1 Hz, 1H), 3.75-3.60 (m, 2H), 2.65 (d, J = 9.3 |

TABLE 2-continued

Mass and NMR data of compounds 2-89

| Compound | MS (ESI, m/z) | $^1$H NMR data |
|---|---|---|
| | | Hz, 1H), 2.38 (s, 1H), 1.84 (t, J = 10.5 Hz, 1H), 1.24 (s, 3H) |
| 10 | 450.1 [M + H]$^+$ | $^1$HNMR (400 MHz, DMSO-d$_6$): δ 10.74-10.61 (m, 1H), 9.47 (s, 1H), 8.53 (s, 2H), 8.27 (s, 1H), 7.51 (d, J = 10.2 Hz, 1H), 6.01 (d, J = 10.5 Hz, 1H), 5.78 (d, J = 5.6 Hz, 1H), 4.20 (d, J = 5.7 Hz, 1H), 3.52-3.42 (m, 2H), 2.37 (s, 1H), 1.83 (s, 1H) |
| 11 | 464.1 [M + H]$^+$ | $^1$HNMR (400 MHz, CDCl$_3$): δ 10.35 (s, 1H), 9.87 (s, 1H), 8.29 (s, 2H), 7.72 (s, 1H), 7.00 (d, J = 11.2 Hz, 1H), 5.71 (d, J = 11.2 Hz, 1H), 4.24 (t, J = 8.0 Hz, 1H), 3.84-3.78 (m, 1H), 3.65-3.56 (m, 4H), 2.66-2.56 (m, 1H), 2.18-2.07 (m, 1H) |
| 12 | 532.1 [M + H]$^+$ | $^1$HNMR (400 MHz, DMSO-d$_6$): δ 10.37 (m, 1H), 9.47 (s, 1H), 8.53 (s, 2H), 8.27 (s, 1H), 7.51 (d, J = 10.2 Hz, 1H), 6.01 (d, J = 10.5 Hz, 1H), 5.78 (d, J = 5.6 Hz, 1H), 4.78 (s, 3H), 4.20 (d, J = 5.7 Hz, 1H), 3.52-3.42 (m, 2H), 2.37 (s, 1H), 1.83 (s, 1H) |
| 13 | 452.1 [M + H]$^+$ | $^1$HNMR (400 MHz, CD$_3$OD): δ 9.46 (s, 1H), 8.63 (s, 2H), 8.07 (s, 1H), 7.47 (d, J = 10.6 Hz, 1H), 5.96 (d, J = 10.5 Hz, 1H), 5.36-5.29 (m, 1H), 5.19 (t, J = 6.4 Hz, 1H), 3.75-3.60 (m, 2H), 2.71-2.61 (m, 1H), 2.39-2.24 (m, 1H) |
| 14 | 462.1 [M + H]$^+$ | $^1$H NMR (400 MHz, CDCl$_3$): δ 9.82 (s, 1H), 8.42 (d, J = 6.8 Hz, 2H), 7.81 (s, 1H), 7.09 (d, J = 11.0 Hz, 1H), 5.73 (d, J = 11.0 Hz, 1H), 3.69 (t, J = 6.8 Hz, 2H), 2.06 (t, J = 6.9 Hz, 2H), 1.31 (s, 6H) |
| 15 | 450.1 [M + H]$^+$ | $^1$H NMR (400 MHz, CDCl$_3$): δ 10.08 (s, 1H), 9.73 (s, 1H), 8.52 (s, 2H), 7.86 (s, 1H), 7.17 (d, J = 11.0 Hz, 1H), 5.97 (d, J = 11.0 Hz, 1H), 4.53 (s, 1H), 4.06 (dd, J = 10.4, 5.1 Hz, 1H), 3.59 (d, J = 10.3 Hz, 1H), 2.81 (dd, J = 17.7, 6.3 Hz, 1H), 2.49 (s, 1H) |
| 16 | 477.2 [M + H]$^+$ | $^1$HNMR (400 MHz, CD$_3$OD): δ 10.08 (s, 1H), 9.68 (s, 1H), 8.52 (s, 2H), 7.78 (s, 1H), 7.07 (d, J = 11.0 Hz, 1H), 5.68 (d, J = 11.0 Hz, 1H), 4.01 (dd, J = 10.0, 6.0 Hz, 1H), 3.64 (dd, J = 10.0, 2.4 Hz, 1H), 3.21-3.28 (m, 1H), 2.81 (dd, J = 17.7, 7.0 Hz, 1H), 2.58 (dd, J = 17.7, 2.8 Hz, 1H), 2.25 (s, 6H) |
| 17 | 464.1 [M + H]$^+$ | $^1$H NMR (400 MHz, CDCl$_3$): δ 9.72 (s, 1H), 9.65 (s, 1H), 8.39 (s, 2H), 7.78 (s, 1H), 7.07 (d, J = 11.1 Hz, 1H), 5.68 (d, J = 11.1 Hz, 1H), 4.19-4.13 (m, 1H), 4.01 (dd, J = 10.0, 6.0 Hz, 1H), 3.64 (dd, J = 10.0, 2.4 Hz, 1H), 3.37 (s, 3H), 2.81 (dd, J = 17.7, 7.0 Hz, 1H), 2.58 (dd, J = 17.7, 2.8 Hz, 1H) |
| 18 | 460.1 [M + H]$^+$ | $^1$H NMR (400 MHz, CDCl$_3$): δ 10.19 (s, 1H), 9.82 (s, 1H), 8.36 (s, 2H), 7.75 (s, 1H), 7.04 (d, J = 11.0 Hz, 1H), 5.68 (d, J = 11.1 Hz, 1H), 3.80 (t, J = 7.3 Hz, 2H), 2.25 (t, J = 7.3 Hz, 2H), 1.24 (d, J = 2.8 Hz, 2H), 0.89 (q, J = 4.3 Hz, 2H) |
| 19 | 460.1 [M + H]$^+$ | $^1$HNMR (400 MHz, DMSO-d$_6$): δ 10.83 (s, 1H), 9.51 (s, 1H), 8.55 (s, 2H), 8.28 (s, 1H), 7.54 (d, J = 10.4 Hz, 1H), 6.04 (d, J = 10.5 Hz, 1H), 3.98 (s, 4H), 3.81 (s, 2H), 2.77 (s, 2H), 2.70 (s, 3H) |
| 20 | 476.1 [M + H]$^+$ | $^1$HNMR (400 MHz, CD$_3$OD): δ 9.46 (s, 1H), 8.64 (s, 2H), 8.08 (s, 1H), 7.45 (d, J = 10.6 Hz, 1H), 5.95 (d, J = 10.5 Hz, 1H), 4.75-4.64 (m, 4H), 3.95 (s, 2H), 2.86 (s, 2H) |
| 21 | 504.1 [M + H]$^+$ | $^1$HNMR (400 MHz, CDCl$_3$): δ 9.62 (s, 1H), 9.45 (s, 1H), 8.46 (s, 2H), 7.84 (s, 1H), 7.13 (d, J = 10.9 Hz, 1H), 5.68 (d, J = 11.4 Hz, 1H), 3.72 (s, 4H), 3.60 (s, 2H), 2.48 (s, 2H), 1.84-1.72 (m, 4H) |
| 22 | 502.2 [M + H]$^+$ | $^1$HNMR (400 MHz, DMSO-d$_6$): δ 10.50 (s, 1H), 9.42 (s, 1H), 8.53 (s, 2H), 8.27 (s, 1H), 7.49 (d, J = 10.4 Hz, 1H), 5.98 (d, J = 10.4 Hz, 1H), 3.29 (s, 2H), 2.20 (s, 2H), 1.53-1.26 (m, 10H) |
| 23 | 517.2 [M + H]$^+$ | $^1$HNMR (400 MHz, DMSO-d$_6$): δ 10.75 (s, 1H), 9.42 (s, 1H), 8.55 (s, 2H), 8.28 (s, 1H), 7.52 (d, J = 10.4 Hz, 1H), 6.03 (d, J = 10.4 Hz, 1H), 3.58-3.48 (m, 2H), 3.40-3.35 (m, 2H), 3.04 (s, 2H), 2.74 (s, 3H), 2.10-1.95 (m, 4H), 1.75 (m, 2H) |
| 24 | 545.2 [M + H]$^+$ | $^1$HNMR (400 MHz, CD$_3$OD): δ 9.53 (s, 1H), 8.66 (s, 2H), 8.10 (s, 1H), 7.48 (d, J = 10.5 Hz, 1H), 5.98 (d, J = 10.5 Hz, 1H), 3.71-3.54 (m, 6H), 2.50 (s, 2H), 2.14 (s, 3H), 1.85-1.79 (m, 2H), 1.73 (t, J = 5.7 Hz, 2H) |

TABLE 2-continued

Mass and NMR data of compounds 2-89

| Compound | MS (ESI, m/z) | $^1$H NMR data |
|---|---|---|
| 25 | 489.1 [M + H]$^+$ | $^1$HNMR (400 MHz, DMSO-d$_6$): δ 10.83 (s, 1H), 9.51 (s, 1H), 8.55 (s, 2H), 8.28 (s, 1H), 7.54 (d, J = 10.4 Hz, 1H), 6.04 (d, J = 10.5 Hz, 1H), 3.98 (s, 4H), 3.81 (s, 2H), 2.77 (s, 2H), 2.70 (s, 3H) |
| 26 | 489.1 [M + H]$^+$ | $^1$HNMR (400 MHz, DMSO-d$_6$): δ 10.81 (s, 1H), 9.45 (s, 1H), 8.54 (s, 2H), 8.28 (s, 1H), 7.53 (d, J = 10.4 Hz, 1H), 6.03 (d, J = 10.5 Hz, 1H), 3.92 (s, 4H), 2.77 (s, 2H), 2.72 (s, 3H), 1.75 (m, 2H) |
| 27 | 545.2 [M + H]$^+$ | $^1$HNMR (400 MHz, CD$_3$OD): δ 9.45 (s, 1H), 8.63 (s, 2H), 8.06 (s, 1H), 7.44 (d, J = 10.5 Hz, 1H), 5.95 (d, J = 10.5 Hz, 1H), 4.25-4.15 (m, 1H), 3.95-3.85 (m, 1H), 3.64-3.60 (m, 2H), 3.45-3.36 (m, 1H), 3.26-3.16 (m, 1H), 2.17 (t, J = 6.9 Hz, 2H), 2.12 (s, 3H), 1.97-1.79 (m, 2H), 1.70-1.58 (m, 2H) |
| 28 | 488.1 [M + H]$^+$ | $^1$HNMR (400 MHz, DMSO-d$_6$): δ 10.48 (s, 1H), 9.47 (s, 1H), 8.54 (s, 2H), 8.28 (s, 1H), 7.50 (d, J = 10.4 Hz, 1H), 7.50 (d, J = 10.4 Hz, 1H), 6.03 (d, J = 10.6 Hz, 1H), 3.83 (dd, J = 9.2, 4.0 Hz, 1H), 2.48-2.41 (m, 1H), 2.35-2.27 (m, 1H), 2.00-1.95 (m, 1H), 1.75-1.71 (m, 1H), 1.67-1.60 (m, 1H), 1.57-1.41 (m, 2H), 1.32-1.26 (m, 2H), 1.24-1.14 (m, 2H) |
| 29 | 446.1 [M + H]$^+$ | $^1$H NMR (400 MHz, CDCl$_3$): δ 10.13 (s, 1H), 9.83 (s, 1H), 8.38 (s, 2H), 7.75 (s, 1H), 7.04 (d, J = 11.0 Hz, 1H), 5.65 (d, J = 11.1 Hz, 1H), 3.34 (d, J = 7.3 Hz, 2H), 2.05 (d, J = 7.3 Hz, 1H), 1.78 (m, 1H), 1.24 (d, J = 2.8 Hz, 2H), 0.89 (q, J = 2.8 Hz, 2H) |
| 30 | 458.1 [M + H]$^+$ | $^1$H NMR (400 MHz, CDCl$_3$): δ 9.68 (s, 1H), 9.14 (s, 1H), 8.40 (s, 2H), 7.80 (s, 1H), 7.09 (d, J = 11.2 Hz, 1H), 6.86 (s, 1H), 6.67 (s, 1H), 5.60 (d, J = 11.1 Hz, 1H), 4.53 (s, 1H), 3.42 (s, 1H), 2.66 (d, J = 8.4 Hz, 1H), 2.35 (d, J = 8.5 Hz, 1H) |
| 31 | 458.1 [M + H]$^+$ | $^1$H NMR (400 MHz, CDCl$_3$): δ 9.67 (s, 1H), 9.13 (s, 1H), 8.41 (s, 2H), 7.81 (s, 1H), 7.09 (d, J = 11.1 Hz, 1H), 6.86 (dd, J = 5.4, 1.9 Hz, 1H), 6.67 (s, 1H), 5.61 (d, J = 11.1 Hz, 1H), 4.53 (s, 1H), 3.42 (s, 1H), 2.66 (d, J = 8.4 Hz, 1H), 2.35 (d, J = 8.4 Hz, 1H) |
| 32 | 460.1 [M + H]$^+$ | $^1$H NMR (400 MHz, CDCl$_3$): δ 9.97 (s, 1H), 9.81 (s, 1H), 8.36 (s, 2H), 7.75 (s, 1H), 7.05 (d, J = 11.0 Hz, 1H), 5.60 (d, J = 11.0 Hz, 1H), 4.20 (s, 1H), 2.93 (s, 1H), 2.17 (d, J = 9.9 Hz, 1H), 2.00 (d, J = 12.6 Hz, 1H), 1.83 (m, 2H), 1.48 (d, J = 9.8 Hz, 1H), 1.23 (m, 1H) |
| 33 | 460.1 [M + H]$^+$ | $^1$H NMR (400 MHz, CDCl$_3$): δ 10.02 (s, 1H), 9.82 (s, 1H), 8.34 (s, 2H), 7.74 (s, 1H), 7.04 (d, J = 11.0 Hz, 1H), 5.59 (d, J = 11.1 Hz, 1H), 4.20 (s, 1H), 2.93 (s, 1H), 2.18 (d, J = 9.9 Hz, 1H), 2.02 (m, 1H), 1.83 (m, 2H), 1.48 (d, J = 9.7 Hz, 1H), 1.23 (m, 1H) |
| 34 | 435.1 [M + H]$^+$ | $^1$HNMR (400 MHz, DMSO-d$_6$): δ 10.30 (s, 1H), 9.51 (s, 1H), 8.54 (s, 2H), 8.27 (s, 1H), 7.47 (d, J = 10.4 Hz, 1H), 6.91 (s, 1H), 5.97 (d, J = 10.4 Hz, 1H), 3.59-3.52 (m, 2H), 3.31-3.28 (m, 2H) |
| 35 | 449.1 [M + H]$^+$ | $^1$HNMR (400 MHz, CDCl$_3$): δ 9.85 (s, 1H), 9.59 (s, 1H), 8.40 (s, 2H), 7.79 (s, 1H), 7.02 (d, J = 11.0 Hz, 1H), 5.75 (d, J = 11.0 Hz, 1H), 3.71 (t, J = 7.7 Hz, 2H), 3.48 (t, J = 7.7 Hz, 2H), 2.92 (s, 3H) |
| 36 | 449.1 [M + H]$^+$ | $^1$HNMR (400 MHz, CD$_3$OD): δ 9.50 (s, 1H), 8.62 (s, 2H), 8.06 (s, 1H), 7.40 (d, J = 10.5 Hz, 1H), 5.94 (d, J = 10.5 Hz, 1H), 3.60 (t, J = 5.9 Hz, 2H), 3.33-3.30 (m, 2H), 2.13-2.04 (m, 2H) |
| 37 | 463.1 [M + H]$^+$ | $^1$HNMR (400 MHz, CD$_3$OD): δ 9.49 (s, 1H), 8.63 (s, 2H), 8.07 (s, 1H), 7.41 (d, J = 10.5 Hz, 1H), 5.94 (d, J = 10.5 Hz, 1H), 3.60 (t, J = 6.0 Hz, 2H), 3.36 (t, J = 6.0 Hz, 2H), 2.96 (s, 3H), 2.17-2.06 (m, 2H) |
| 38 | 450.1 [M + H]$^+$ | $^1$H NMR (400 MHz, CDCl$_3$): δ 10.08 (s, 1H), 9.72 (s, 1H), 8.36 (d, J = 1.6 Hz, 2H), 7.77 (s, 1H), 7.06 (d, J = 11.1 Hz, 1H), 5.71 (d, J = 11.1 Hz, 1H), 4.36 (s, 2H), 4.07 (t, J = 5.1 Hz, 2H), 3.80-3.74 (m, 2H) |
| 39 | 449.1 [M + H]$^+$ | $^1$HNMR (400 MHz, CD$_3$OD): δ 9.52 (s, 1H), 8.63 (s, 2H), 8.10 (s, 1H), 7.46 (d, J = 10.3 Hz, 1H), 6.00 (d, J = 10.3 Hz, 1H), 3.68 (t, J = 5.4 Hz, 2H), 3.30 (s, 2H), 2.90 (t, J = 5.5 Hz, 2H) |
| 40 | 491.1 [M + H]$^+$ | $^1$HNMR (400 MHz, CD$_3$OD): δ 9.57 (s, 1H), 8.66 (s, 2H), 8.10 (s, 1H), 7.46 (d, J = 10.1 Hz, 1H), 6.00 (d, J = 10.1 Hz, 1H), 3.68 (t, J = 5.4 Hz, 2H), 3.30 (s, 2H), 2.90 (t, J = 5.5 Hz, 2H), 2.12 (s, 2H) |
| 41 | 463.1 [M + H]$^+$ | $^1$HNMR (400 MHz, CD$_3$OD): δ 9.52 (s, 1H), 8.66 (s, 2H), 8.10 (s, 1H), 7.46 (d, J = 10.5 Hz, 1H), 6.00 (d, J = |

TABLE 2-continued

Mass and NMR data of compounds 2-89

| Compound | MS (ESI, m/z) | $^1$H NMR data |
|---|---|---|
| | | 10.5 Hz, 1H), 3.68 (t, J = 5.4 Hz, 2H), 3.30 (s, 2H), 2.90 (t, J = 5.5 Hz, 2H), 2.43 (s, 3H) |
| 42 | 463.1 [M + H]$^+$ | $^1$HNMR (400 MHz, CD$_3$OD): δ 9.57 (s, 1H), 8.63 (s, 2H), 8.08 (s, 1H), 7.46 (d, J = 10.3 Hz, 1H), 6.00 (d, J = 10.3 Hz, 1H), 3.54 (t, J = 5.4 Hz, 2H), 2.92 (t, J = 5.5 Hz, 2H) |
| 43 | 477.1 [M + H]$^+$ | $^1$HNMR (400 MHz, CD$_3$OD): δ 9.52 (s, 1H), 8.66 (s, 2H), 8.08 (s, 1H), 7.48 (d, J = 10.1 Hz, 1H), 5.98 (d, J = 10.1 Hz, 1H), 3.54 (t, J = 5.4 Hz, 2H), 2.92 (t, J = 5.5 Hz, 2H), 2.43 (s, 3H) |
| 44 | 491.1 [M + H]$^+$ | $^1$H NMR (400 MHz, CDCl$_3$) δ 10.45 (s, 1H), 9.83 (s, 1H), 8.48 (s, 2H), 7.84 (s, 1H), 7.19 (d, J = 10.9 Hz, 1H), 5.93 (d, J = 11.0 Hz, 1H), 3.92 (t, J = 5.7 Hz, 2H), 3.75 (t, J = 5.9 Hz, 2H), 3.58 (q, J = 7.2 Hz, 2H), 1.24 (t, J = 5.6 Hz, 3H) |
| 45 | 463.1 [M + H]$^+$ | $^1$HNMR (400 MHz, CD$_3$OD): δ 9.57 (s, 1H), 8.66 (s, 2H), 8.10 (s, 1H), 7.46 (d, J = 10.1 Hz, 1H), 5.97 (d, J = 10.1 Hz, 1H), 3.56 (s, 2H), 3.42 (s, 2H) |
| 46 | 477.1 [M + H]$^+$ | $^1$HNMR (400 MHz, CD$_3$OD): δ 9.54 (s, 1H), 8.67 (s, 2H), 8.10 (s, 1H), 7.46 (d, J = 10.1 Hz, 1H), 5.98 (d, J = 10.1 Hz, 1H), 3.56 (s, 2H), 3.42 (s, 2H), 2.42 (s, 3H) |
| 47 | 462.1 [M + H]$^+$ | $^1$HNMR (400 MHz, CD$_3$OD): δ 9.58 (s, 1H), 8.66 (s, 2H), 8.08 (s, 1H), 7.46 (d, J = 10.1 Hz, 1H), 6.00 (d, J = 10.1 Hz, 1H), 3.21 (s, 2H), 2.96 (t, J = 5.4 Hz, 2H), 2.54 (t, J = 5.4 Hz, 2H) |
| 48 | 476.1 [M + H]$^+$ | $^1$H NMR (400 MHz, CDCl$_3$): δ 10.06 (s, 1H), 9.68 (s, 1H), 8.35 (d, J = 1.6 Hz, 2H), 7.76 (s, 1H), 7.06 (d, J = 11.1 Hz, 1H), 5.70 (d, J = 11.1 Hz, 1H), 4.36 (s, 2H), 3.74 (s, 2H), 1.24 (d, J = 2.8 Hz, 2H), 0.89 (q, J = 2.8 Hz, 2H) |
| 49 | 474.1 [M + H]$^+$ | $^1$H NMR (400 MHz, DMSO-d$_6$): δ 11.76 (s, 1H), 9.52 (s, 1H), 8.57 (s, 2H), 8.30 (s, 1H), 7.65 (d, J = 7.0 Hz, 1H), 7.62 (d, J = 10.4 Hz, 1H), 6.39 (t, J = 6.7 Hz, 2H), 6.16 (d, J = 10.4 Hz, 1H), 2.73 (s, 3H) |
| 50 | 482.1 [M + H]$^+$ | $^1$HNMR (400 MHz, DMSO-d$_6$): δ 9.46 (s, 1H), 8.56 (s, 2H), 8.27 (s, 1H), 7.76 (d, J = 7.3 Hz, 1H), 7.72-7.63 (m, 2H), 7.55 (dd, J = 11.9, 7.0 Hz, 3H), 6.09 (d, J = 10.5 Hz, 1H), 4.65 (s, 2H) |
| 51 | 483.1 [M + H]$^+$ | $^1$HNMR (400 MHz, DMSO-d$_6$): δ 10.26 (s, 1H), 9.45 (s, 1H), 8.36 (s, 2H), 8.27 (s, 1H), 7.85 (dd, J = 5.1, 1.5 Hz, 1H), 7.47 (d, J = 10.5 Hz, 1H), 7.42 (dd, J = 7.0, 1.4 Hz, 1H), 6.69 (dd, J = 7.1, 5.2 Hz, 1H), 6.02 (d, J = 10.5 Hz, 1H), 4.63 (s, 2H) |
| 52 | 468.1 [M + H]$^+$ | $^1$HNMR (400 MHz, CD$_3$OD): δ 9.45 (s, 1H), 8.63 (m, 2H), 8.05 (s, 1H), 7.42 (d, J = 10.4 Hz, 1H), 7.14 (d, J = 7.2 Hz, 1H), 6.98-7.0 (m, 1H), 6.75-6.80 (m, 1H), 6.69 (d, J = 7.6 Hz, 1H), 5.98 (d, J = 10.4 Hz, 1H), 3.58 (t, J = 8.0 Hz, 2H), 3.02 (t, J = 8.0 Hz, 2H) |
| 53 | 469.1 [M + H]$^+$ | $^1$HNMR (400 MHz, DMSO-d$_6$): δ 10.46 (s, 1H), 9.50 (s, 1H), 8.52 (s, 2H), 8.27 (s, 1H), 7.85 (dd, J = 5.1, 1.5 Hz, 1H), 7.47 (d, J = 10.5 Hz, 1H), 7.42 (dd, J = 7.0, 1.4 Hz, 1H), 6.69 (dd, J = 7.1, 5.2 Hz, 1H),, 6.02 (d, J = 10.5 Hz, 1H), 3.68 (t, J = 8.1 Hz, 2H), 2.99 (t, J = 8.2 Hz, 2H) |
| 54 | 466.1 [M + H]$^+$ | $^1$HNMR (400 MHz, CD$_3$OD): δ 9.56 (s, 1H), 8.63 (m, 2H), 8.15 (s, 1H), 7.42 (d, J = 10.4 Hz, 1H), 7.14 (d, J = 7.2 Hz, 1H), 6.98-7.05 (m, 2H), 6.75-6.80 (m, 1H), 6.69 (d, J = 7.6 Hz, 1H), 6.12 (d, J = 11.2 Hz, 1H), 5.98 (d, J = 10.4 Hz, 1H) |
| 55 | 467.1 [M + H]$^+$ | $^1$H NMR (400 MHz, CDCl$_3$): δ 10.03 (s, 1H), 8.36 (s, 1H), 8.25 (s, 2H), 8.11 (s, 1H), 7.8 Hz, 1H), 7.69 (s, 1H), 7.44 (d, J = 3.7 Hz, 1H), 7.28 (s, 2H), 7.02 (d, J = 11.2 Hz, 1H), 6.69 (d, J = 3.7 Hz, 1H), 6.09 (d, J = 11.2 Hz, 1H) |
| 56 | 444.1 [M + H]$^+$ | $^1$H NMR (400 MHz, DMSO-d$_6$): δ 11.76 (s, 1H), 9.52 (s, 1H), 8.57 (s, 2H), 8.30 (s, 1H), 7.65 (d, J = 7.0 Hz, 1H), 7.62 (d, J = 10.4 Hz, 1H), 7.58-7.50 (m, 1H), 6.58 (d, J = 9.1 Hz, 1H), 6.28 (t, J = 6.7 Hz, 2H), 6.16 (d, J = 10.4 Hz, 1H) |
| 57 | 445.1 [M + H]$^+$ | $^1$H NMR (400 MHz, DMSO-d$_6$): δ 11.56 (s, 1H), 9.56 (s, 1H), 8.53 (s, 2H), 8.26 (s, 1H), 7.65 (d, J = 7.0 Hz, 1H), 7.63 (d, J = 10.4 Hz, 1H), 7.58-7.50 (m, 1H), 6.58 (d, J = 9.1 Hz, 1H), 6.32 (t, J = 6.7 Hz, 2H) |
| 58 | 488.1 [M + H]$^+$ | $^1$H NMR (400 MHz, DMSO-d$_6$): δ 8.69 (s, 1H), 7.81-7.74 (m, 2H), 7.23 (s, 1H), 6.63 (d, J = 10.6 Hz, 1H), 6.55-6.45 (m, 1H), 5.17 (d, J = 10.5 Hz, 1H), 3.14-3.08 (m, 2H), 3.03 (t, J = 9.9 Hz, 2H), 2.71 (t, J = 9.8 Hz, 2H), 2.59 (dd, J = 6.7, 4.8 Hz, 2H) |

TABLE 2-continued

Mass and NMR data of compounds 2-89

| Compound | MS (ESI, m/z) | $^1$H NMR data |
|---|---|---|
| 59 | 486.1 [M + H]$^+$ | $^1$H NMR (400 MHz, CD$_3$OD): δ 9.53 (s, 1H), 8.61 (d, J = 1.6 Hz, 2H), 8.05 (s, 1H), 7.47 (d, J = 10.6 Hz, 1H), 7.34 (d, J = 1.2 Hz, 1H), 7.23 (d, J = 1.1 Hz, 1H), 6.01 (d, J = 10.5 Hz, 1H), 4.54-4.46 (m, 2H), 4.10 (t, J = 6.1 Hz, 2H) |
| 60 | 485.1 [M + H]$^+$ | $^1$H NMR (400 MHz, DMSO-d$_6$): δ 11.45 (s, 1H), 9.49 (s, 1H), 8.54 (s, 2H), 8.25 (s, 1H), 7.57 (d, J = 10.4 Hz, 1H), 7.50 (d, J = 2.3 Hz, 1H), 7.39 (d, J = 6.0 Hz, 1H), 6.99 (d, J = 4.0 Hz, 1H), 6.80 (d, J = 6.0 Hz, 1H), 6.58 (dd, J = 4.0, 2.5 Hz, 1H), 6.10 (d, J = 10.4 Hz, 1H) |
| 61 | 420.1 [M + H]$^+$ | $^1$H NMR (400 MHz, CD$_3$OD): δ 9.14 (s, 1H), 8.37 (s, 2H), 7.92 (s, 1H), 7.35 (d, J = 10.5 Hz, 1H), 6.06 (d, J = 10.4 Hz, 1H), 4.21 (t, J = 8.5 Hz, 2H), 2.92 (s, 2H) |
| 62 | 434.1 [M + H]$^+$ | $^1$H NMR (400 MHz, CDCl$_3$): δ 9.41 (s, 1H), 8.58-8.53 (m, 2H), 7.91 (s, 1H), 7.28 (d, J = 10.7 Hz, 1H), 5.87 (d, J = 10.7 Hz, 1H), 4.14 (t, J = 8.0 Hz, 2H), 3.37 (s, 3H), 2.68 (t, J = 7.9 Hz, 2H) |
| 63 | 437.2 [M + H]$^+$ | $^1$H NMR (400 MHz, CDCl$_3$) δ 9.38 (s, 1H), 8.53 (s, 2H), 7.89 (s, 1H), 7.27 (d, J = 10.8 Hz, 1H), 5.87 (d, J = 10.7 Hz, 1H), 4.11 (d, J = 8.3 Hz, 2H), 2.66 (t, J = 8.0 Hz, 2H) |
| 64 | 448.1 [M + H]$^+$ | $^1$H NMR (400 MHz, CDCl$_3$): δ 9.57 (s, 1H), 8.58-8.51 (m, 2H), 7.91 (s, 1H), 7.29 (d, J = 10.7 Hz, 1H), 5.87 (d, J = 10.7 Hz, 1H), 4.14 (t, J = 8.0 Hz, 2H), 3.35 (q, J = 5.8 Hz, 3H), 2.71 (t, J = 7.9 Hz, 2H), 1.35 (t, J = 5.8 Hz, 3H) |
| 65 | 462.1 [M + H]$^+$ | $^1$H NMR (400 MHz, CDCl$_3$): δ 9.87 (s, 1H), 8.58 (s, 2H), 7.88 (s, 1H), 7.16 (d, J = 11.1 Hz, 1H), 6.48 (d, J = 11.0 Hz, 1H), 4.92 (t, J = 6.5 Hz, 1H), 4.06 (t, J = 9.6 Hz, 2H), 2.88 (t, J = 9.5 Hz, 2H), 1.33 (d, J = 6.2 Hz, 6H) |
| 66 | 460.1 [M + H]$^+$ | $^1$H NMR (400 MHz, CDCl$_3$): δ 9.41 (s, 1H), 8.58-8.48 (m, 2H), 7.92 (s, 1H), 7.29 (d, J = 10.7 Hz, 1H), 5.87 (d, J = 10.7 Hz, 1H), 4.13 (t, J = 8.0 Hz, 2H), 3.21 (m, 1H), 2.69 (t, J = 7.9 Hz, 2H), 1.24 (d, J = 2.8 Hz, 2H), 0.89 (q, J = 4.3 Hz, 2H) |
| 67 | 510.1 [M + H]$^+$ | $^1$H NMR (400 MHz, CDCl$_3$): δ 9.35 (s, 1H), 8.56 (d, J = 1.8 Hz, 2H), 7.91 (s, 1H), 7.43-7.13 (m, 6H), 5.77 (d, J = 10.8 Hz, 1H), 5.04 (s, 2H), 3.89 (t, J = 7.8 Hz, 2H), 2.68 (t, J = 7.9 Hz, 2H) |
| 68 | 498.1 [M + H]$^+$ | $^1$H NMR (400 MHz, CDCl$_3$): δ 9.30 (d, J = 1.5 Hz, 2H), 8.66-8.48 (m, 2H), 8.47-8.29 (m, 2H), 7.92 (s, 1H), 7.07 (d, J = 10.6 Hz, 0H), 5.90 (d, J = 10.6 Hz, 1H), 4.36 (t, J = 7.4 Hz, 2H), 2.92 (t, J = 7.6 Hz, 2H) |
| 69 | 517.2 [M + H]$^+$ | $^1$H NMR (400 MHz, CDCl$_3$): δ 9.84 (s, 1H), 8.58 (s, 2H), 7.88 (s, 1H), 7.16 (d, J = 11.0 Hz, 1H), 6.45 (d, J = 11.0 Hz, 1H), 4.72 (s, 1H), 4.07 (t, J = 9.5 Hz, 2H), 2.91 (t, J = 9.5 Hz, 2H), 2.62 (s, 2H), 2.28 (s, 3H), 2.03 (d, J = 13.0 Hz, 2H), 1.92-1.74 (m, 2H), 1.24 (d, J = 11.7 Hz, 2H) |
| 70 | 491.2 [M + H]$^+$ | $^1$H NMR (400 MHz, CD$_3$OD): δ 9.04 (s, 1H), 8.55 (s, 2H), 8.06 (s, 1H), 7.44 (d, J = 10.1 Hz, 1H), 6.17 (dd, J = 10.1, 1.3 Hz, 1H), 4.11 (dt, J = 15.5, 7.9 Hz, 2H), 3.91 (s, 2H), 2.64-2.52 (m, 4H), 2.26 (d, J = 23.2 Hz, 6H) |
| 71 | 478.1 [M + H]$^+$ | $^1$H NMR (400 MHz, CDCl$_3$): δ 9.44 (s, 1H), 8.56 (s, 2H), 7.91 (s, 1H), 7.27 (d, J = 10.7 Hz, 1H), 5.92 (d, J = 10.7 Hz, 1H), 4.24-3.94 (m, 4H), 3.51 (t, J = 5.1 Hz, 2H), 3.30 (s, 3H), 2.69 (t, J = 7.8 Hz, 2H) |
| 72 | 474.1 [M + H]$^+$ | $^1$H NMR (400 MHz, CDCl$_3$): δ 9.86 (s, 1H), 8.58 (s, 2H), 7.89 (s, 1H), 7.16 (d, J = 11.0 Hz, 1H), 6.48 (d, J = 11.0 Hz, 1H), 4.14-3.91 (m, 4H), 2.94 (t, J = 9.5 Hz, 2H), 0.85 (d, J = 7.1 Hz, 1H), 0.64 (dd, J = 9.1, 4.3 Hz, 2H), 0.33 (t, J = 5.1 Hz, 2H) |
| 73 | 459.1 [M + H]$^+$ | $^1$H NMR (400 MHz, CDCl$_3$): δ 9.33 (s, 1H), 8.55 (s, 2H), 8.09-7.65 (m, 1H), 7.34 (d, J = 10.6 Hz, 1H), 5.92 (d, J = 10.7 Hz, 1H), 4.85 (s, 2H), 4.24 (t, J = 8.0 Hz, 2H), 2.76 (t, J = 8.0 Hz, 2H) |
| 74 | 502.1 [M + H]$^+$ | $^1$H NMR (400 MHz, CDCl$_3$): δ 9.36 (s, 1H), 8.54 (s, 2H), 7.92 (s, 1H), 7.31 (d, J = 10.7 Hz, 1H), 5.88 (d, J = 10.7 Hz, 1H), 4.62 (q, J = 8.4 Hz, 2H), 4.16 (t, J = 7.8 Hz, 2H), 2.73 (t, J = 7.8 Hz, 2H |
| 75 | 505.1 [M + H]$^+$ | $^1$H NMR (400 MHz, CDCl$_3$): δ 9.44 (s, 1H), 8.56 (d, J = 1.7 Hz, 2H), 7.95-7.82 (m, 1H), 7.24 (s, 1H), 5.85 (d, J = 10.7 Hz, 1H), 4.78 (s, 2H), 4.29 (t, J = 8.0 Hz, 2H), 2.98 (s, 2H), 2.93 (s, 3H), 2.80 (t, J = 7.9 Hz, 2H) |
| 76 | 477.1 [M + H]$^+$ | $^1$H NMR (400 MHz, DMSO-d6): δ 9.13 (s, 1H), 8.42 (s, 2H), 8.21 (s, 1H), 7.50 (s, 1H), 7.44 (d, J = 10.1 Hz, 1H), 7.12 (s, 1H), 6.19 (d, J = 10.1 Hz, 1H), 4.37 (s, 2H), 4.20-3.91 (m, 2H), 2.47 (t, J = 1.9 Hz, 1H), 1.95 (s, 1H) |

TABLE 2-continued

Mass and NMR data of compounds 2-89

| Compound | MS (ESI, m/z) | $^1$H NMR data |
|---|---|---|
| 77 | 448.1 [M + H]$^+$ | $^1$H NMR (400 MHz, CDCl$_3$): δ 9.58 (s, 1H), 8.58-8.48 (m, 2H), 7.93 (s, 1H), 7.29 (d, J = 10.7 Hz, 1H), 5.88 (d, J = 10.7 Hz, 1H), 4.12 (t, J = 8.0 Hz, 2H), 3.32 (s, 3H), 2.72 (t, J = 7.9 Hz, 2H), 1.38 (m, 2H) |
| 78 | 448.1 [M + H]$^+$ | $^1$H NMR (400 MHz, CDCl$_3$): δ 9.53 (s, 1H), 8.58-8.53 (m, 2H), 7.91 (s, 1H), 7.28 (d, J = 10.5 Hz, 1H), 5.87 (d, J = 10.5 Hz, 1H), 3.37 (s, 3H), 2.84 (s, 2H) |
| 79 | 462.1 [M + H]$^+$ | $^1$H NMR (400 MHz, CDCl$_3$): δ 9.98 (s, 1H), 9.84 (s, 1H), 8.37 (d, J = 1.6 Hz, 2H), 7.76 (s, 1H), 7.03 (d, J = 11.0 Hz, 1H), 5.76 (d, J = 11.1 Hz, 1H), 5.19 (s, 1H), 4.21 (s, 2H), 3.87 (s, 3H) |
| 80 | 476.1 [M + H]$^+$ | $^1$H NMR (400 MHz, CDCl$_3$): δ 9.79 (s, 1H), 9.46 (s, 1H), 8.42 (s, 2H), 7.80 (s, 1H), 7.08 (d, J = 11.0 Hz, 1H), 5.76 (d, J = 11.0 Hz, 1H), 5.14 (s, 1H), 4.19 (s, 2H), 4.08 (q, J = 7.1 Hz, 2H), 1.42 (t, J = 7.0 Hz, 3H) |
| 81 | 506.1 [M + H]$^+$ | $^1$H NMR (400 MHz, CDCl$_3$): δ 9.96 (s, 1H), 9.42 (s, 1H), 8.42 (s, 2H), 7.83 (s, 1H), 7.08 (d, J = 11.0 Hz, 1H), 5.76 (d, J = 11.0 Hz, 1H), 5.14 (s, 1H), 4.19 (s, 2H), 4.08 (q, J = 7.1 Hz, 2H), 3.72 (q, J = 7.1 Hz, 2H), 3.42 (s, 3H) |
| 82 | 465.1 [M + H]$^+$ | $^1$H NMR (400 MHz, CDCl$_3$): δ 9.98 (s, 1H), 9.84 (s, 1H), 8.37 (d, J = 1.6 Hz, 2H), 7.76 (s, 1H), 7.03 (d, J = 11.0 Hz, 1H), 5.76 (d, J = 11.1 Hz, 1H), 5.19 (s, 1H), 4.21 (s, 2H) |
| 83 | 530.1 [M + H]$^+$ | $^1$H NMR (400 MHz, CDCl$_3$): δ9.68 (s, 1H), 9.22 (s, 1H), 8.45 (s, 2H), 7.83 (s, 1H), 7.13 (d, J = 11.0 Hz, 1H), 5.72 (d, J = 11.1 Hz, 1H), 5.28 (s, 1H), 4.41-4.32 (m, 2H), 4.30 (s, 2H) |
| 84 | 446.1 [M + H]$^+$ | $^1$H NMR (400 MHz, CD$_3$OD): δ 9.43 (s, 1H), 8.62 (d, J = 1.7 Hz, 2H), 8.06 (s, 1H), 7.44 (d, J = 10.8 Hz, 1H), 6.12 (s, 1H), 5.97 (d, J = 10.8 Hz, 1H), 4.58 (s, 1H), 4.08 (d, J = 2.1 Hz, 2H), 1.89 (m, 3H) |
| 85 | 460.1 [M + H]$^+$ | $^1$H NMR (400 MHz, CD$_3$OD): δ 9.45 (s, 1H), 8.61 (d, J = 1.8 Hz, 2H), 8.05 (s, 1H), 7.44 (d, J = 10.6 Hz, 1H), 6.13 (s, 1H), 5.97 (d, J = 10.6 Hz, 1H), 4.56 (s, 1H), 4.08 (d, J = 2.1 Hz, 2H), 1.89 (q, J = 7.2 Hz, 2H), 1.12 (t, J = 7.2 Hz, 3H) |
| 86 | 472.1 [M + H]$^+$ | $^1$H NMR (400 MHz, CD$_3$OD): δ 9.54 (s, 1H), 8.62 (d, J = 1.8 Hz, 2H), 8.06 (s, 1H), 7.44 (d, J = 10.8 Hz, 1H), 6.13 (s, 1H), 5.97 (d, J = 10.8 Hz, 1H), 4.53 (s, 1H), 4.09 (d, J = 2.1 Hz, 2H), 0.89 (d, J = 7.1 Hz, 1H), 0.64 (dd, J = 9.1, 4.3 Hz, 2H), 0.33 (t, J = 5.1 Hz, 2H) |
| 87 | 476.1 [M + H]$^+$ | $^1$H NMR (400 MHz, CDCl$_3$) δ 10.08 (s, 1H), 9.82 (s, 1H), 8.34 (s, 2H), 7.76 (s, 1H), 7.05 (d, J = 11.1 Hz, 1H), 5.79 (s, 1H), 5.73 (d, J = 11.1 Hz, 1H), 3.84 (t, J = 7.2 Hz, 2H), 2.59 (t, J = 7.2 Hz, 2H), 3.84 (s, 3H) |
| 88 | 446.1 [M + H]$^+$ | $^1$H NMR (400 MHz, CDCl$_3$) δ 10.06 (s, 1H), 9.79 (s, 1H), 8.37 (s, 2H), 7.76 (s, 1H), 7.05 (d, J = 11.1 Hz, 1H), 6.76 (dd, J = 9.4, 4.6 Hz, 1H), 6.01 (dt, J = 9.9, 1.8 Hz, 1H), 5.73 (d, J = 11.1 Hz, 1H), 3.87 (t, J = 7.2 Hz, 2H), 2.71-2.62 (m, 2H) |
| 89 | 460.1 [M + H]$^+$ | $^1$H NMR (400 MHz, CDCl$_3$) δ 10.22 (s, 1H), 9.84 (s, 1H), 8.34 (s, 2H), 7.74 (s, 1H), 7.01 (d, J = 11.1 Hz, 1H), 5.79 (s, 1H), 5.73 (d, J = 11.1 Hz, 1H), 3.77 (t, J = 7.2 Hz, 2H), 2.59 (t, J = 7.2 Hz, 2H), 2.00 (s, 3H) |

Example 90 Synthesis of (Z)-3-(3-(3,5-bis(trifluoromethyl)phenyl)-1H-1,2,4-triazol-1-yl)-1-(pyrazolidin-1-yl)prop-2-en-1-one (Compound 90)

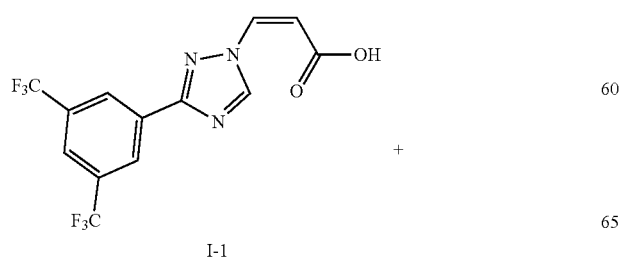

I-1

-continued

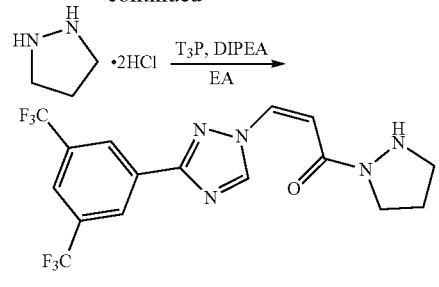

90

A 100 mL three-necked flask was filled with pyrazolidine dihydrochloride (1.5 g, 10.34 mmol), DIPEA (6.23 g, 48.3 mmol) and DMF (72 mL), then the mixture was cooled to −50° C. under the atmosphere of Ar gas. Compound 1-1 (2.42 g, 6.9 mmol) was added and T₃P (6.58 g, 10.34 mmol) was added dropwise at −50° C. After dropping, the mixture was stirred at −50° C. for 12 h, monitored by TLC (DCM:MeOH=20:1 to DCM:MeOH=10:1) and LC-MS. After the reaction was completed, the system was quenched with water (145 mL) at −50° C., stirred at room temperature for 30 mins, filtered, and the filter cake was washed three times with water (10 mL each time) and dried in vacuo to give a white-like solid of compound 90 (1.97 g, yield: 71.6%).

¹H NMR (400 MHz, CD₃OD): δ 9.18 (s, 1H), 8.60-8.55 (m, 2H), 8.04 (s, 1H) 7.26 (d, J=10.3 Hz, 1H), 6.42 (d, J=10.3 Hz, 1H), 4.57 (s, 1H), 3.65-3.55 (m, 2H), 2.95 (t, J=6.6 Hz, 2H), 2.15-2.06 (m, 2H); MS (ESI, m/z): 406.1 [M+H]⁺.

Example 91 Synthesis of (Z)-3-(3-(3,5-bis(trifluoromethyl)phenyl)-1H-1,2,4-triazol-1-yl)-1-(2-methylpyrazolidin-1-yl)prop-2-en-1-one (Compound 91)

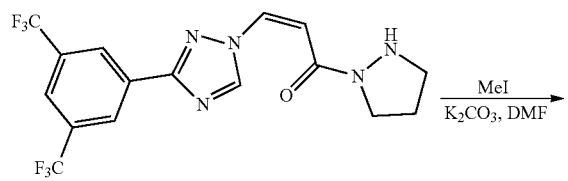

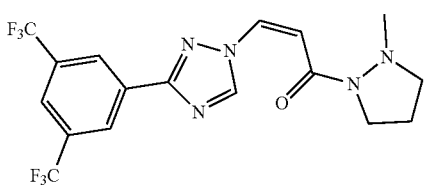

91

Compound 90 (50 mg, 0.123 mmol), K₂CO₃ (34 mg, 0.247 mmol) and DMF (5 mL) were added into a 10 mL single-necked flask. After replacement with Ar gas, MeI (35 mg, 0.247 mmd) was added, then the mixture was heated to 50° C. and further stirred for 20 h. Monitored by TLC (DCM:MeOH=20:1) and LC-MS, the mixture was cooled to room temperature after the completion of the reaction, quenched with water (10 mL), extracted twice with EA (10 mL each time), the combined organic layers were concentrated to dryness, and the residue was purified by pre-TLC to give a white solid of compound 91 (31 mg, yield: 60%).

¹H NMR (400 MHz, CDCl₃): δ 9.76 (s, 1H), 8.58 (s, 2H), 7.89 (s, 1H), 7.15 (d, J=11.0 Hz, 1H), 6.52 (d, J=11.0 Hz, 1H), 3.71 (m, 2H), 3.00 (t, J=6.9 Hz, 2), 2.54 (s, 3H), 2.24 (m, 2H); MS (ESI, m/z): 420.1 [M+H]⁺

Example 92 to Example 103: Synthesis of Compound 92 to Compound 103

Compounds 92-103 were synthesized by using 90 as starting material, and reacting with different halogens, amides, sulfonamides, and the like under basic conditions, which is similar to the synthesis of compound 91.

TABLE 3

| Compound | MS (ESI, m/z) | ¹H NMR |
|---|---|---|
| 92 | 434.1 [M + H]⁺ | ¹H NMR (400 MHz, CD₃OD): δ 9.22 (s, 1H), 8.57 (d, J = 1.7 Hz, 2H), 8.04 (s, 1H), 7.27 (d, J = 10.4 Hz, 1H), 6.47 (d, J = 10.4 Hz, 1H), 3.03-2.88 (m, 2H), 2.72 (q, J = 7.2 Hz, 2H), 2.32-1.99 (m, 2H), 1.31-1.23 (m, 2H), 1.07 (t, J = 7.2 Hz, 3H) |
| 93 | 448.1 [M + H]⁺ | ¹H NMR (400 MHz, CDCl₃): δ 9.67 (s, 1H), 8.56 (s, 2H), 7.91 (s, 1H), 7.16 (d, J = 11.0 Hz, 1H), 6.58 (d, J = 11.0 Hz, 1H), 3.71 (m, 2H), 3.00 (t, J = 6.9 Hz, 2H), 2.76 (q, J = 6.8 Hz, 1H), 2.54 (s, 3H), 2.24 (m, 2H), 1.12 (t, J = 6.9 Hz, 3H) |
| 94 | 445.1 [M + H]⁺ | ¹H NMR (400 MHz, CDCl₃): δ 9.33 (s, 1H), 8.55 (s, 2H), 8.09-7.65 (m, 1H), 7.34 (d, J = 10.6 Hz, 1H), 5.92 (d, J = 10.7 Hz, 1H), 4.85 (s, 2H), 4.32 (m, 2H), 3.16 (m, 2H), 2.10 (m, 2H) |
| 95 | 448.1 [M + H]⁺ | ¹H NMR (400 MHz, CDCl₃): δ 9.36 (s, 1H), 8.54 (s, 2H), 8.32 (s, 1H), 7.31 (d, J = 10.7 Hz, 1H), 5.89 (d, J = 10.7 Hz, 1H), 4.62 (q, J = 8.4 Hz, 2H), 4.36 (m, 2H), 3.18 (m, 2H), 2.12 (m, 2H) |
| 96 | 484.1 [M + H]⁺ | ¹H NMR (400 MHz, CDCl₃): δ 9.68 (s, 1H), 8.58 (s, 2H), 8.36 (s, 1H), 8.28-8.15 (m, 2H), 7.90 (s, 1H), 7.12 (d, J = 10.9 Hz, 1H), 6.21 (d, J = 10.9 Hz, 1H), 4.55 (s, 1H), 4.29 (s, 1H), 3.32 (d, J = 35.4 Hz, 2H), 2.20 (s, 1H), 2.01 (s, 1H) |
| 97 | 448.1 [M + H]⁺ | ¹H NMR (400 MHz, CDCl₃): δ 9.54 (s, 1H), 8.57 (d, J = 1.7 Hz, 2H), 7.91 (s, 1H), 7.21 (s, 1H), 6.12 (s, 1H), 4.33 (m, 2H), 3.19 (m, 2H), 2.14 (s + m, 3H + 2H) |
| 98 | 474.1 [M + H]⁺ | ¹H NMR (400 MHz, CDCl₃): δ 9.54 (s, 1H), 8.57 (s, 2H), 7.91 (s, 1H), 7.20 (s, 1H), 6.19 (s, 1H), 4.36 (m, 2H), 3.18 (m, 2H), 2.12 (m, 2H), 1.93 (m, 1H) 1.05 (m, 2H), 0.87 (m, 2H) |

TABLE 3-continued

Mass and NMR data of compounds 92-103

| Compound | MS (ESI, m/z) | $^1$H NMR |
|---|---|---|
| 99 | 491.1 [M + H]$^+$ | $^1$H NMR (400 MHz, CD$_3$OD): δ 8.98 (s, 1H), 8.49 (s, 2H), 7.98 (s, 1H), 7.38-7.11 (m, 1H), 6.10 (s, 1H), 4.05 (m, 2H), 3.25 (m, 3H), 2.21 (m, 7H), 2.11-1.94 (m, 2H) |
| 100 | 512.1 [M + H]$^+$ | $^1$H NMR (400 MHz, CDCl$_3$): δ 9.15-9.24 (m, 2H), 8.70 (s, 1H), 8.56 (s, 3H), 7.90 (s, 1H), 7.15 (d, J = 11.0 Hz, 1H), 6.25 (d, J = 11.0 Hz, 1H), 4.28 (s, 2H), 3.48 (s, 2H), 2.21 (d, J = 12.1 Hz, 2H) |
| 101 | 545.1 [M + H]$^+$ | $^1$H NMR (400 MHz, CDCl$_3$): δ 9.2-9.15 (s, 1H), 8.54 (s, 2H), 8.5-8.3 (m, 1H), 7.91 (s, 1H), 7.8-7.7 (m, 1H), 7.35-7.25 (m, 1H), 7.14 (d, J = 10.6 Hz, 1H), 6.2-5.8 (m, 1H), 4.30-4.21 (m, 1H), 3.81-3.26 (m, 3H), 2.35-2.15 (m, 2H) |
| 102 | 484.1 [M + H]$^+$ | $^1$H NMR (400 MHz, CDCl$_3$): δ 9.46 (s, 1H), 8.56 (s, 2H), 7.89 (s, 1H), 7.15 (d, J = 11.0 Hz, 1H), 6.25 (d, J = 11.0 Hz, 1H), 3.12 (s, 3H), 3.00 (t, J = 6.9 Hz, 2H), 2.91 (s, 2H), 2.24 (m, 2H) |
| 103 | 505.1 [M + H]$^+$ | $^1$H NMR (400 MHz, CDCl$_3$): δ 9.24 (s, 1H), 8.55 (s, 2H), 7.91 (s, 1H), 7.21 (d, J = 10.2 Hz, 1H), 5.99 (d, J = 10.2 Hz, 1H), 3.84 (d, J = 2.96 Hz, 6H), 3.02 (s, 2H), 2.91 (s, 2H), 2.21 (s, 2H) |

Example 104 Rev-GFP Nuclear Export Assay

The Rev protein from HIV contains nuclear export sequence (NES) at its C terminus and nuclear localization sequence (NLS) at its N-terminus. The nuclear localization of Rev protein depends on CRM1. U2OS cells expressing Rev protein fused with GFP (Rev-GFP) were plated in black 384 plates with clear bottom one day prior to treatment. Compounds were serially diluted 2-fold from 40 μM with DMEM in 384 plates, and then incubated with U2OS cells for an hour. Cells were fixed with 3.7% formaldehyde afterwards and nuclei were stained with Hoechst33258. The nuclear retention of Rev-GFP was examined, and IC$_{50}$ was calculated. The results of the Rev-GFP assay were summarized in Table 4. Compounds of the present disclosure, as exemplified in Examples, showed IC$_{50}$ in the following ranges: A=IC$_{50}$≤1 μM; B=1 μM<IC$_{50}$≤10 μM; C=IC$_{50}$>10 μM.

Example 105 Cancer Cell Proliferation Assay

BxPC-3 cells (pancreatic cancer) and MDA-MB-231 cells (breast cancer cells) were harvested from exponential phase cultures and seeded in 96-well plates at a cell density of 2×10$^4$ per well. After overnight attachment, compounds including positive controls were applied to cells at five concentrations and incubated for three days. During the last four hours of incubation, 20 μL of 5 mg/mL NT was added followed by the further addition of 100 μL DMSO. The plates were subsequently shook for 10 minutes to dissolve insoluble purple formazan. Absorbance (A) at a wavelength of 570 nm was quantified. Percentage of inhibition was used for the calculation of IC$_{50}$ based on the bliss method.

TABLE 4

IC$_{50}$ value of Examples in nuclear export assay and cell proliferation assay (A = <1 μM, B = 1-10 μM, C = >10 μM, NT = not tested)

| Compound | IC$_{50}$ of REV-GFP | IC$_{50}$ (μM) BxPC-3 | IC$_{50}$ (μM) MDA-MB-231 |
|---|---|---|---|
| 2 | A | 0.269 | 0.024 |
| 4 | A | 0.238 | 0.034 |
| 5 | A | 0.202 | 0.955 |
| 6 | A | 0.471 | 0.487 |
| 9 | A | 0.334 | 0.504 |
| 10 | B | 0.527 | 0.519 |
| 15 | NT | 0.352 | 1.230 |
| 23 | A | 0.664 | 0.407 |
| 28 | B | 0.769 | 0.240 |
| 30 | A | 0.392 | 0.515 |
| 32 | A | 0.134 | 0.277 |
| 33 | A | 0.156 | 0.165 |
| 38 | A | 0.283 | 0.654 |
| 56 | A | 0.449 | 0.382 |
| 62 | A | 0.124 | 0.186 |
| 65 | A | 0.168 | 0.055 |
| 67 | A | 0.483 | 0.965 |
| 71 | A | 0.586 | 0.245 |
| 72 | A | 0.137 | 0.119 |
| 79 | A | 0.204 | 0.126 |
| 80 | A | 0.145 | 0.266 |
| 82 | A | 0.016 | 0.102 |
| 83 | A | 0.344 | 0.214 |
| 87 | A | 0.041 | 0.021 |
| 88 | A | 0.259 | 0.410 |
| 89 | A | 0.184 | 0.277 |
| 96 | A | 0.334 | 0.675 |
| 98 | A | 0.302 | 0.487 |
| KPT-330 | A | 0.705 | 0.458 |

As presented in the table above, compounds of the present invention exhibit enhanced activity in inhibiting the nuclear export of Rev-GFP and the proliferation of tumor cells. For example, the compound of Example 87 demonstrates 20 folds of enhancement of activity in the anti-proliferative assay, the IC$_{50}$ of which is 41 and 21 nM in BxPC-3 and MDA-MB-231 cells respectively, in comparison to 705 and 455 nM of that of KPT330.

Example 106 Aqeuous Solubility Assay 10-30 mg of compounds were dissolved in water and an HCl solution at pH1.2 respectively, and then were continuously shook for three days, followed by centrifugation at 10000 rpm/minute for five minutes. A 2 mL aliquot of supernatant was removed and diluted to 50 mL to prepare a sample solution. A control solution was prepared by dissolving 2.5 mg compounds in methanol, which was subsequently diluted with water to a final volume of 50 mL. 20 μL of control and sample solutions were injected into HPLC. The area under the curve (A) of the sample solution was compared with that of the control solution and used for determination of the concentration. Solubility was calculated by the formula below.

Solubility (mg/mL)=c(control)*25*$A$(sample)/$A$(control)

C (control): concentration of the control solution
A (sample): area under the curve of the sample solution
A (control): area under the curve of the control solution

TABLE 5

Solubility of Compounds in Aqueous Solutions

| Compound | Solubility (μg/mL) | |
|---|---|---|
| | Water | HCl solution of pH 1.2 |
| 2 | 11.31 | 14.55 |
| 23 | 40.32 | 158.76 |
| 38 | 50.42 | 71.38 |
| 62 | 319.98 | 220.10 |
| 71 | 228.65 | 146.78 |
| 72 | 20.92 | 27.44 |
| 79 | 7.89 | 8.54 |
| 90 | 156.43 | 348.97 |
| KPT-330 | 6.25 | 6.52 |

As shown in Table 5, compounds of the present invention are more soluble in water and HCl solution of pH 1.2 than KPT-330. Better water solubility can markedly improve the pharmaeoinetic property of drugs and facilitate formulation development.

Example 107 In Vivo Pharmacokinetic Analysis

A group of 9 ICR mice received 5 mg/kg of compound in 0.5% CMC by oral gavage. Blood was taken before treatment and at 5 min, 30 min, 1, 2, 4, 8, 12 and 24 h after treatment. 80 μL of whole blood was sampled (n=3 at each time point) via retro-orbital bleeds or cardiac puncture. The blood sample was collected into EDTA tubes and plasma were obtained by centrifugation at 1500-1600 rpm for 10 min at 4° C. After centrifugation, plasma sample was transferred to a new tube and stored at −60 to −90° C. for future analysis. Plasma concentration of (compounds was quantified by a method based on liquid chromatography coupled to tandem mass-spectrometric detections (LC/MS/MS). Noncompartmental pharmacokinetics parameters were calculated.

TABLE 6

Pharmacokinetic Parameters of Compounds (5 mg/kg) in mice

| Compound | $t_{1/2}$ (h) | $T_{max}$ (h) | MRT (h) | $C_{max}$ (ng/mL) | $AUC_{0-t}$ (ng · h/L) |
|---|---|---|---|---|---|
| 2 | 4.58 | 0.5 | 6.59 | 502 | 2660 |
| 3 | 3.31 | 1.0 | 7.86 | 499 | 5810 |
| 5 | 4.53 | 1.0 | 4.34 | 674 | 3690 |
| 18 | 3.12 | 0.5 | 6.17 | 320 | 3100 |
| 33 | 4.36 | 1.0 | 6.76 | 697 | 5770 |
| 38 | 4.53 | 0.5 | 6.67 | 536 | 4390 |
| 79 | 3.42 | 1.0 | 5.89 | 440 | 3410 |
| 87 | 2.70 | 0.5 | 6.56 | 389 | 4080 |
| KPT-330 | 2.66 | 0.5 | 6.94 | 325 | 2470 |

As shown in the table above, compared to KPT330, compounds of Examples disclosed in this invention exhibit longer $t_{1/2}$, higher $C_{max}$ and $AUC_{0-t}$, which may have significant implications in efficacy, dose reductions and cost savings.

Example 108 Anti-Tumor Growth Efficacy in Pancreatic Tumor BxPC3 Nude Mice Xenograft Model BxPC-3 cells were cultured in 1640 medium containing 10% FBS at 37° C. and 5% $CO_2$, $8\times10^6$ BxPc-3 cells were implanted subcutaneously into the left armpit of 40 nude mice. When the averaged tumor volume reached 65-66 mm$^3$, 30 mice were randomized by tumor volume into five groups (n=6) and treated with vehicle (5% DMSO/45% PEG400/50% water), KPT-330, compound 38, 79 and 62. Compound 62 was administered orally everyday (qd) at 10 mg/kg, whereas KPT330 and compound 38 were given three times a week (tiw, Monday, Wednesday and Friday) at 10 mg/kg by oral gavage, and compound 79 were given three times a week (tiw, Monday, Wednesday and Friday) at 2.5 mg/kg by oral gavage. Tumor volume and body weight were measured every other day. Mice were sacrificed on day 21, and tumor and terminal body weight were recorded. The relative tumor volume, percent treatment/control values and tumor growth inhibition were calculated and statistics was performed.

TABLE 7

Summary of tumor growth and body weight of BxPC-3 xenograft models

| Example | Dose (/kg) | schedule | average body weight (g) | | Tumor volume (mm³) | | RTV | T/C (%) | TGI (%) |
|---|---|---|---|---|---|---|---|---|---|
| | | | D1 | D21 | D1 | D21 | | | |
| Vehicle | — | tiw*21 | 19.77 | 21.55 | 65.07 ± 17.11 | 449.15 ± 99.67 | 6.80 | — | — |
| KPT-330 | 10 | tiw*21 | 19.97 | 19.97 | 65.06 ± 6.45 | 151.31 ± 23.90 | 2.38* | 35.02 | 77.55 |
| Example 38 | 10 | tiw*21 | 19.02 | 20.80 | 65.89 ± 12.63 | 149.62 ± 23.20 | 2.45* | 36.02 | 78.20 |
| Example 79 | 2.5 | tiw*21 | 20.15 | 21.30 | 66.87 ± 9.13 | 126.90 ± 17.73 | 1.63* | 49.20 | 84.37 |
| Example 62 | 10 | qd*21 | 20.55 | 21.08 | 65.32 ± 6.61 | 152.32 ± 24.78 | 2.33* | 35.10 | 77.35 |

*$P < 0.05$ vs. vehicle group; D1: first day of drug treatment; RTV: relative tumor volume; RTV = $V_t/V_0$; T/C(%) = $T_{RTV}/C_{RTV}$ X 100; $T_{RTV}$: RTV of the treatment group; $C_{RTV}$: RTV of the vehicle group. TGI (%): Tumor growth inhibition (%). T/C(%) > 60 is considered ineffective; T/C(%) ≤ 60 and $P < 0.05$ is considered effective.

Figure 2:
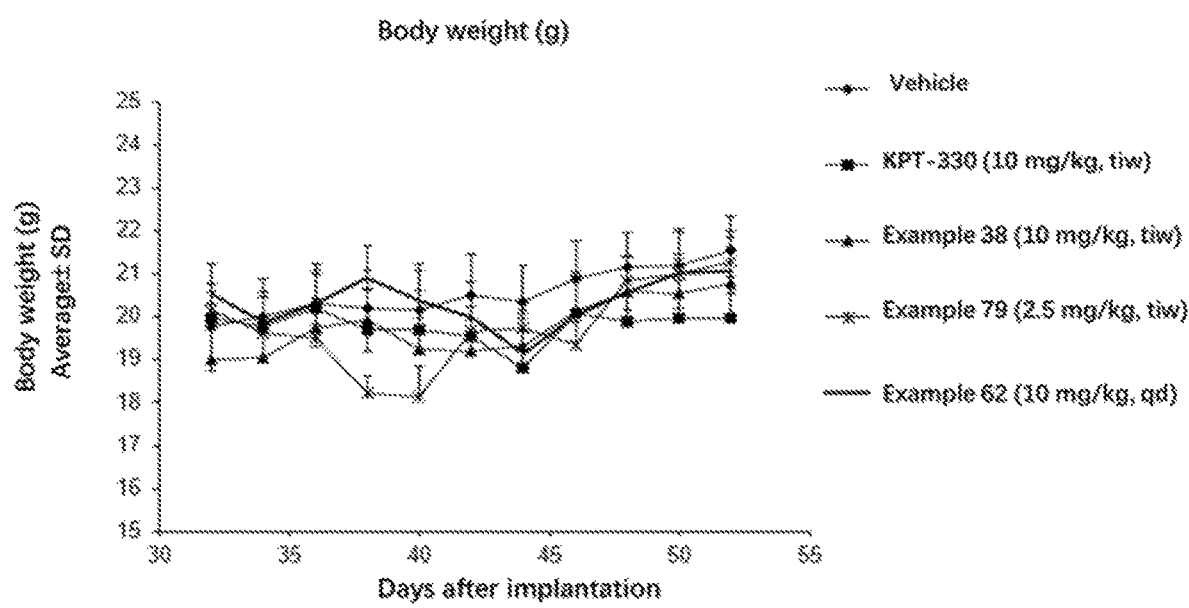
FIG. 2 is a graph of body weight changes of vehicle control, KPT-330, compounds 38, 79 and 62 in BxPC-3 xenografts in nude mice.

As shown in table 7, and FIGS. 1 and 2, Example 79 demonstrates significant anti-tumor growth activity in BxPC-3 xenograft model. Compared to 10 mg/kg KPT-330, 2.5 mg/kg of Example 79 is more potent in inhibiting tumor growth. At 10 mg/kg, Example 38 shows greater efficacy and less effect on body weight than KPT-330, suggesting a greater margin of safety.

While specific embodiments of the invention have been described above, it will be understood by those skilled in the art that these are merely examples, and various changes or modifications may be made to these embodiments without departing from the principles and spirit of the invention. Accordingly, the scope of the invention is defined by the appended claims.

What is claimed is:

1. A compound of general formula (1), an optical isomer, a crystalline form, a pharmaceutically acceptable salt, a hydrate or a solvate thereof:

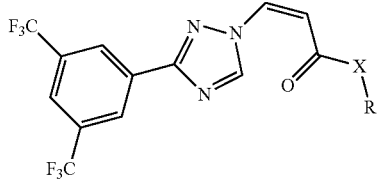

(1)

wherein:
X is —NH— or a bond;
when X is —NH—, R is —NR$^1$COR$^2$, wherein R$^1$ and R$^2$ together with an amide group connected thereto form a 4-7 membered saturated, unsaturated or partially saturated heterocycle, the heterocycle is optionally substituted by 1-2 groups selected from the group consisting of halogen, CN, CF$_3$, CH$_2$CF$_3$, CH$_2$CN, OCF$_3$, OCH$_2$CF$_3$, OH, R$^3$, OR$^3$ and NR$^3$ R$^{3'}$; wherein R$^3$ and R$^{3'}$ are independently selected from the group consisting of H, substituted or unsubstituted C1-C3 alkyl, and substituted or unsubstituted C3-C6 cycloalkyl; or
R$^1$ and R$^2$ together with the amide group connected thereto form a 5-7 membered non-aromatic heterocycle fused with a 5-6 membered aromatic heterocycle, a 5-7 membered non-aromatic heterocycle fused with a 3-6 membered non-aromatic heterocycle, a spiro ring formed by a 5-7 membered non-aromatic heterocycle and a 3-6 membered non-aromatic heterocycle, or a bridged ring formed by a 5-7 membered non-aromatic heterocycle and a 3-6 membered non-aromatic heterocycle; the fused 5-7 membered non-aromatic heterocycle, the fused 5-7 membered non-aromatic heterocycle, the spiro ring, and the bridged ring are optionally substituted by 1-2 groups selected from the group consisting of halogen, CN, CF$_3$, OCF$_3$, OCH$_2$CF$_3$, OH, R$^3$ and OR$^3$; wherein R$^3$ is substituted or unsubstituted C1-C3 alkyl, or substituted or unsubstituted C3-C6 cycloalkyl;
when X is a bond, R is —NR$^4$NR$^5$COR$^6$, wherein R$^5$ is selected from the group consisting of H, substituted or unsubstituted C1-C3 alkyl, substituted or unsubstituted C3-C6 cycloalkyl, alkoxy substituted C1-C3 alkyl, cycloalkyl substituted C1-C3 alkyl, substituted or unsubstituted 5-7 membered heteroaryl, and substituted or unsubstituted 5-7 membered non-aromatic heterocycle; R$^4$ and R$^6$ together with a hydrazide group connected thereto form a 5-7 membered non-aromatic heterocycle, which is optionally substituted by 1-2 groups selected from the group consisting of halogen, CN, OH, R$^3$ or OR$^3$; and R$^3$ is substituted or unsubstituted C1-C3 alkyl, or substituted or unsubstituted C3-C6 cycloalkyl; or when X is a bond, R is the following group:

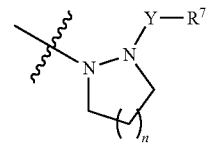

wherein, n is 1 or 2;
Y is selected from the group consisting of a bond, —CH$_2$—, —CH$_2$CH$_2$—, —CO—, —SO$_2$—, —SO—, —CON(R$^8$)—, —SO$_2$N(R$^8$)—, and —COCON(R$^8$)—, wherein R$^8$ is H, substitution or unsubstituted C1-C3 alkyl, or substituted or unsubstituted C3-C6 cycloalkyl;
R$^7$ is selected from the group consisting of H, substituted or unsubstituted C1-C3 alkyl, substituted or unsubstituted C1-C3 alkoxy, substituted or unsubstituted C3-C6 cycloalkyl, substituted or unsubstituted 5-7 membered heteroaryl, and substituted or unsubstituted 5-7 membered non-aromatic heterocycle.

2. The compound according to claim 1, wherein the compound of general formula (1) is represented by the following formula (1A):

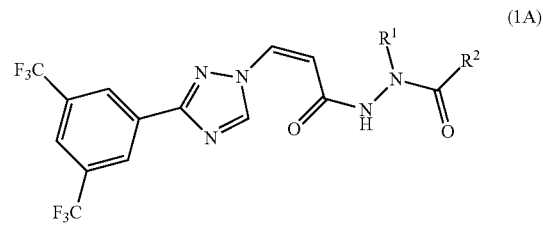

(1A)

or a pharmaceutically acceptable salt thereof, wherein:
R$^1$ and R$^2$ together with the amide group connected thereto form a 4-7 membered saturated, unsaturated or partially saturated heterocycle, the heterocycle is optionally substituted by halogen, CN, CF$_3$, CH$_2$CF$_3$, CH$_2$CN, OCF$_3$, OCH$_2$CF$_3$, OH, R$^3$, OR$^3$ or NR$^3$ R$^{3'}$; wherein R$^3$ and R$^{3'}$ are independently selected from the group consisting of H, substituted or unsubstituted C1-C3 alkyl, and substituted or unsubstituted C3-C6 cycloalkyl; or
R$^1$ and R$^2$ together with the amide group connected thereto form a 5-7 membered non-aromatic heterocycle fused with a 5-6 membered aromatic heterocycle, a 5-7 membered non-aromatic heterocycle fused with a 3-6 membered non-aromatic heterocycle, a spiro ring formed by a 5-7 membered non-aromatic heterocycle and a 3-6 membered non-aromatic heterocycle, a bridged ring formed by a 5-7 membered non-aromatic heterocycle and a 3-6 membered non-aromatic heterocycle, and the fused 5-7 membered non-aromatic heterocycle, the fused 5-7 membered non-aromatic heterocycle, the spiro ring, and the bridged ring are optionally by 1-2 groups selected from the group consisting of halogen, CN, CF$_3$, OCF$_3$, OCH$_2$CF$_3$, OH, R³ or OR³; wherein R³ is substituted or unsubstituted C1-C3 alkyl, or substituted or unsubstituted C3-C6 cycloalkyl.

3. The compound according to claim 1, wherein the compound of general formula (1) is represented by the following formula (1B):

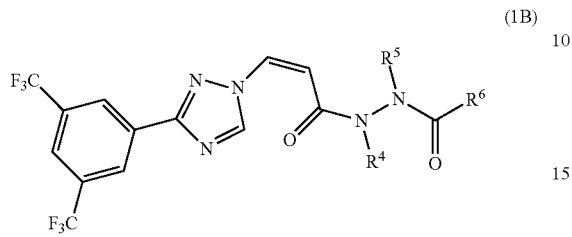

(1B)

or a pharmaceutically acceptable salt thereof, wherein:

R⁵ is selected from the group consisting of H, substituted or unsubstituted C1-C3 alkyl, substituted or unsubstituted C3-C6 cycloalkyl, alkoxy substituted C1-C3 alkyl, cycloalkyl substituted C1-C3 alkyl, substituted or unsubstituted 5-7 membered heteroaryl, and substituted or unsubstituted 5-7 membered non-aromatic heterocycle; R⁴ and R⁶ together with the hydrazide group connected thereto form a 5-7 membered non-aromatic heterocycle, the heterocycle is optionally substituted by 1-2 groups selected from the group consisting of halogen, CN, OH, R³ and OR³; wherein R³ is substituted or unsubstituted C1-C3 alkyl, or substituted or unsubstituted C3-C6 cycloalkyl.

4. The compound according to claim 1, wherein the compound of general formula (1) is represented by the following formula (1C):

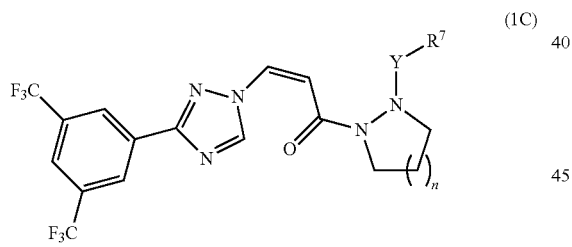

(1C)

or a pharmaceutically acceptable salt thereof, wherein:

n is 1 or 2;

Y is selected from the group consisting of a bond, —CH₂—, —CH₂CH₂—, —CO—, —SO₂—, —SO—, —CON(R⁸)—, —SO₂N(R⁸)—, and —COCON(R⁸)—; wherein R⁸ is H, substituted or unsubstituted C1-C3 alkyl, or substituted or unsubstituted C3-C6 cycloalkyl; and R⁷ is selected from the group consisting of H, substituted or unsubstituted C1-C3 alkyl, substituted or unsubstituted C1-C3 alkoxy, substituted or unsubstituted C3-C6 cycloalkyl, substituted or unsubstituted 5-7 membered heteroaryl, and substituted or unsubstituted 5-7 membered non-aromatic heterocycle.

5. The compound according to claim 2, wherein the compound of formula (1A) is represented by the following formula (1AA):

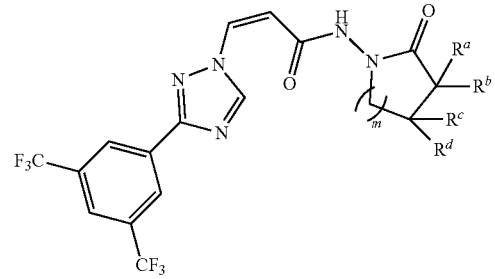

(1AA)

or a pharmaceutically acceptable salt thereof, wherein:

m is 0, 1, 2 or 3;

Rᵃ, Rᵇ, Rᶜ and Rᵈ are independently selected from the group consisting of H, halogen, CN, CF₃, OCF₃, OCH₂CF₃, OH, NMe₂, R³ and OR³; wherein R³ is C1-C3 alkyl group or C3-C6 cycloalkyl group; or Rᵃ and Rᵇ together with a carbon atom connected thereto form a C3-C6 cycloalkyl group or a 3-6 membered non-aromatic heterocycle; or Rᶜ and Rᵈ together with a carbon atom connected thereto form a C3-C6 cycloalkyl group or a 3-6 membered non-aromatic heterocycle; or Rᵃ (or Rᵇ) and Rᶜ (or Rᵈ) together with a C—C bond connected thereto form a C3-C6 cycloalkyl or 3-6 membered non-aromatic heterocycle;

the 3-6 membered non-aromatic heterocycle is optionally substituted by 1-2 groups selected from the group consisting of halogen, CN, OH, R³ and OR³; wherein R³ is substituted or unsubstituted C1-C3 alkyl, or substituted or unsubstituted C3-C6 cycloalkyl.

6. The compound according to claim 2, wherein the compound of formula (1A) is represented by the following formula (1AB):

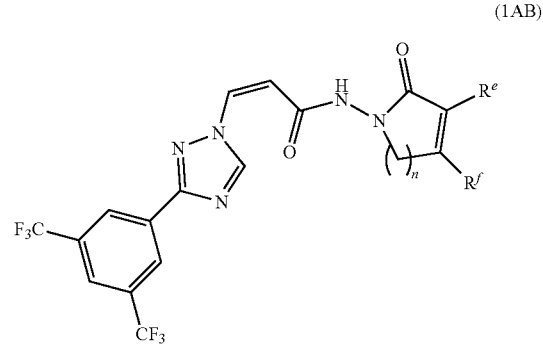

(1AB)

or a pharmaceutically acceptable salt thereof, wherein:

n is 1 or 2;

Rᵉ and Rᶠ are independently selected from group consisting of H, OH, OCH₂CF₃, R³ and OR³; wherein R³ is substituted or unsubstituted C1-C3 alkyl, or substituted or unsubstituted C3-C6 cycloalkyl.

7. The compound according to claim 2, wherein the compound of general formula (1A) is represented by the following formula (1AC):

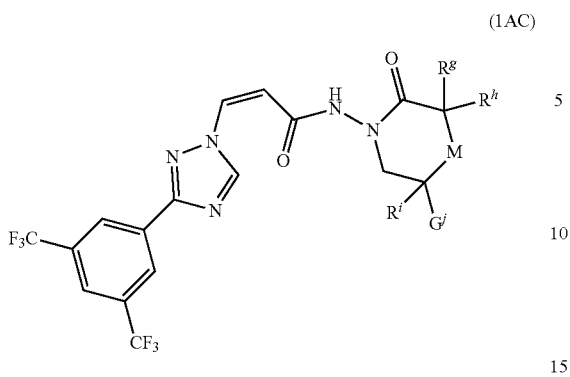
(1AC)

or a pharmaceutically acceptable salt thereof, wherein:

M is —O—, —S—, —NR³— or —CONR³—, wherein R³ is C1-C3 alkyl or C3-C6 cycloalkyl;

$R^g$, $R^h$, $R^i$ and $R^j$ are independently selected from the group consisting of H, R³ and OR³; wherein R³ is substituted or unsubstituted C1-C3 alkyl, or substituted or unsubstituted C3-C6 cycloalkyl; or $R^g$ and $R^h$ together represent a —CO— group, or $R^g$ and $R^h$ together with a carbon atom connected thereto form a C3-C6 cycloalkyl; or $R^i$ and $G^j$ together represent a —CO— group, or $R^i$ and $G^j$ together with a carbon atom connected thereto form a C3-C6 cycloalkyl.

8. The compound according to claim 3, wherein the compound of formula (1B) is represented by the following formula (1BA):

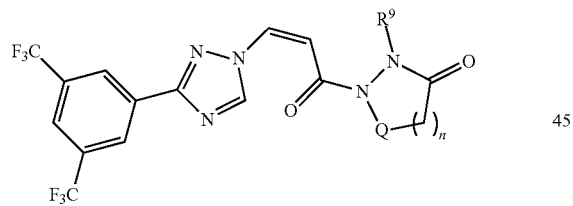
(1BA)

or a pharmaceutically acceptable salt thereof, wherein:

n is 1 or 2;

Q is —CH₂— or —CO—;

R⁹ is selected from the group consisting of H, C1-C3 alkyl, deuterated C1-C3 alkyl, C3-C6 cycloalkyl, amino substituted C1-C3 alkyl-amino, alkoxy substituted C1-C3 alkyl, cycloalkyl substituted C1-C3 alkyl, 5-7 membered heteroaryl, and 5-7 membered non-aromatic heterocycle.

9. The compound according to claim 1, or a pharmaceutically acceptable salt thereof, wherein the compound is selected from the group consisting of:

1
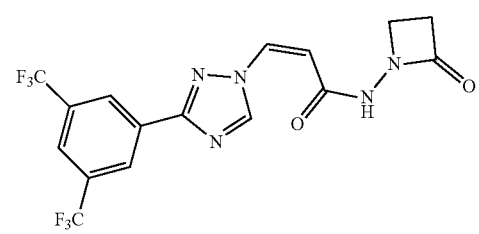

2
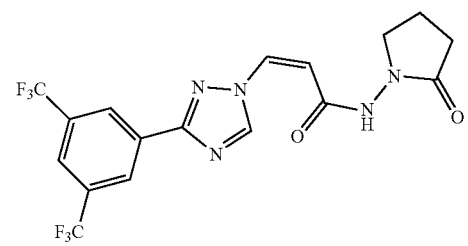

3
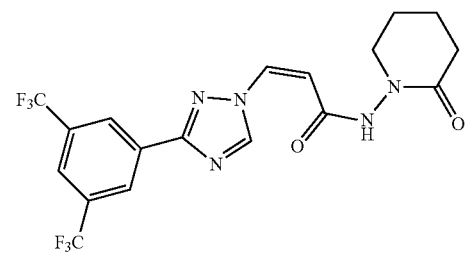

4
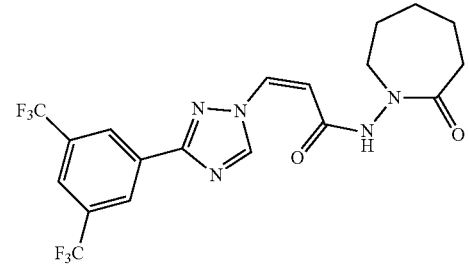

5
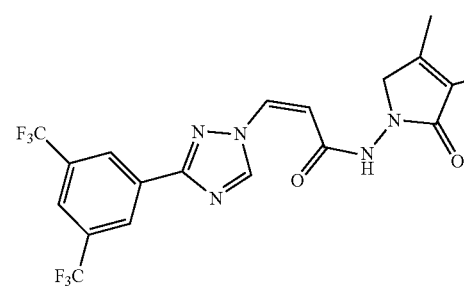

6
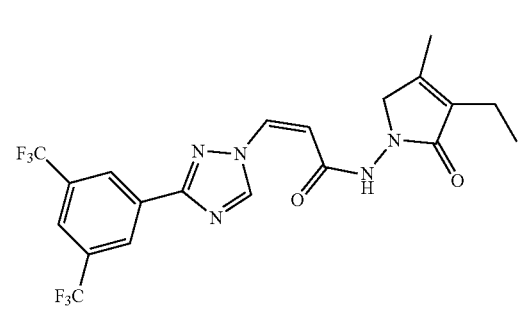

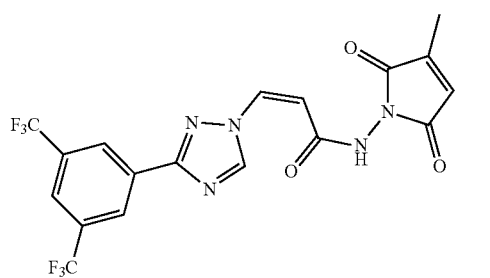
7
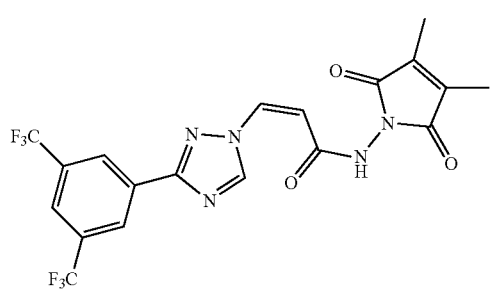
8
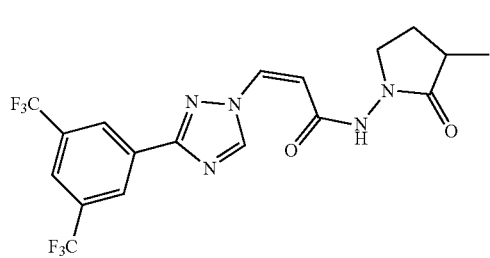
9
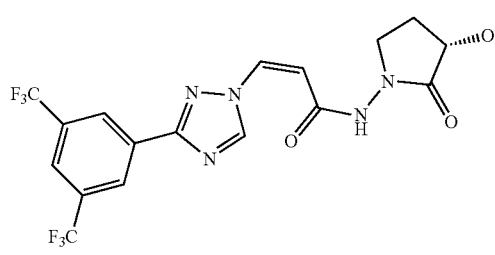
10
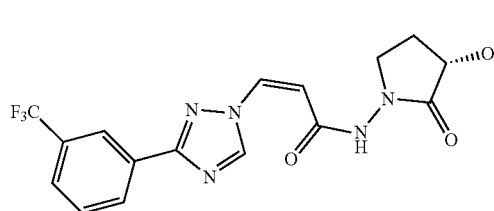
11
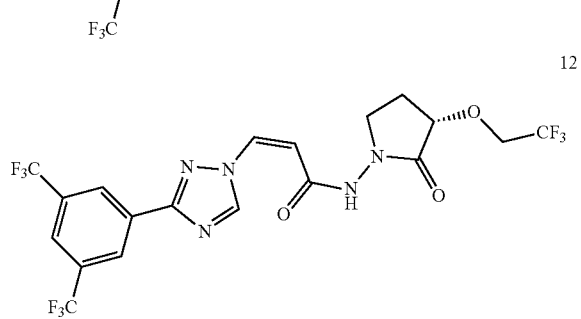
12
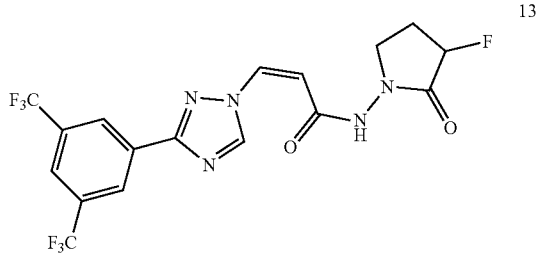
13
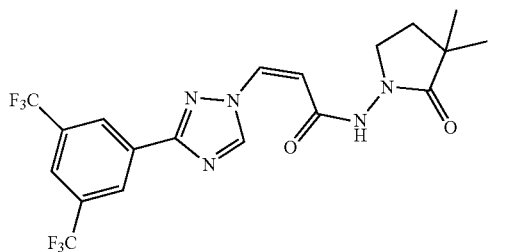
14
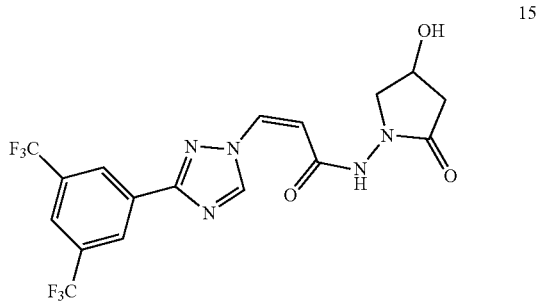
15
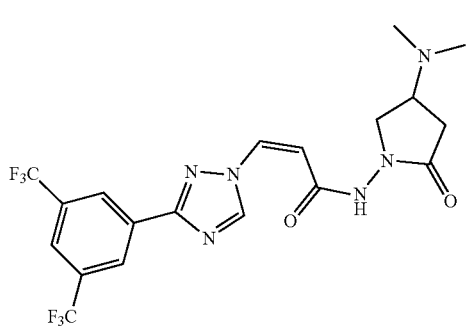
16
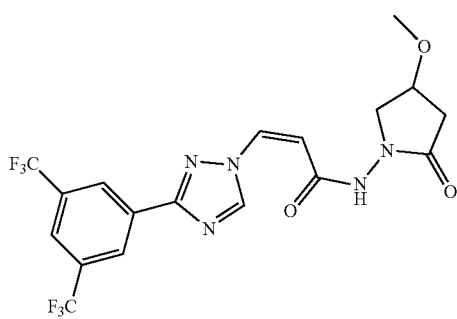
17

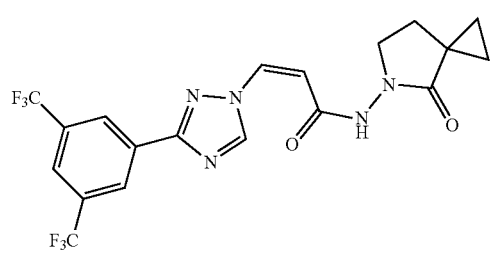
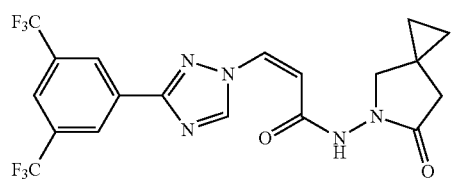
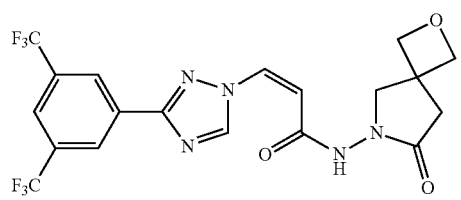
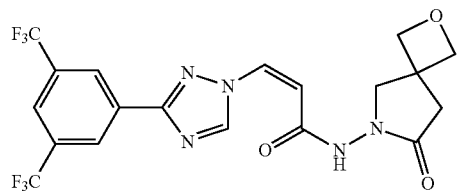
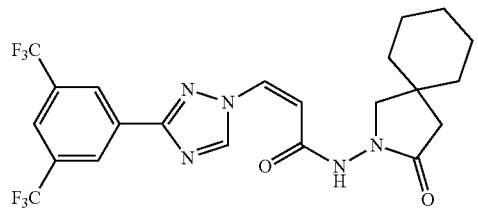
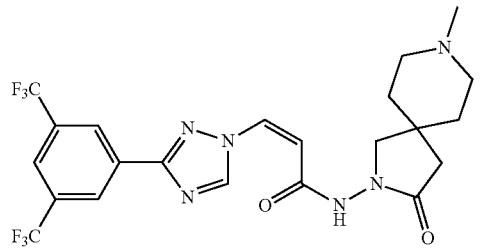
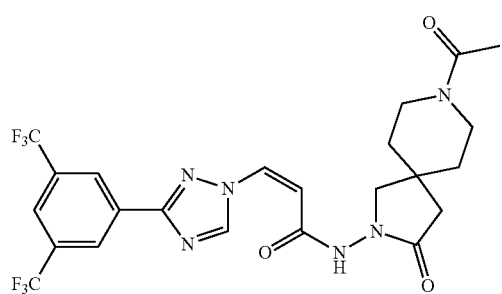
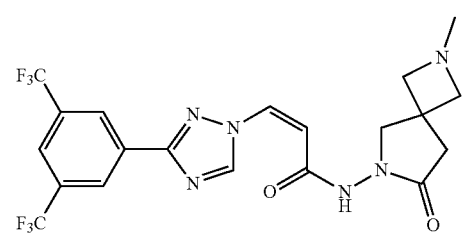
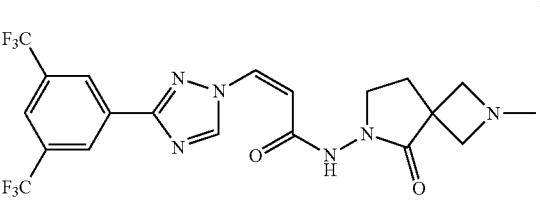
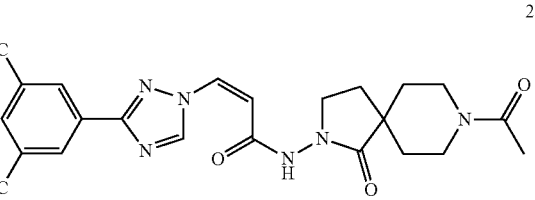
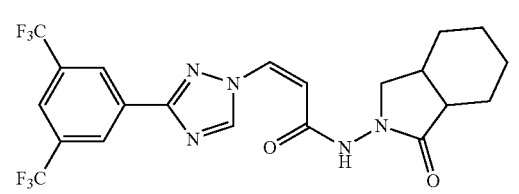
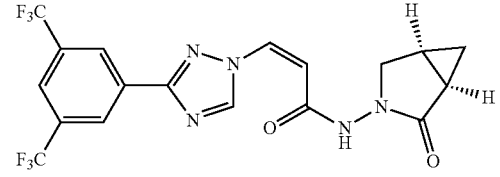
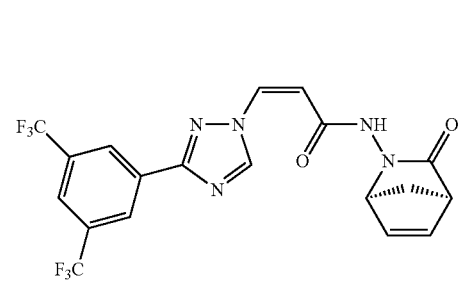
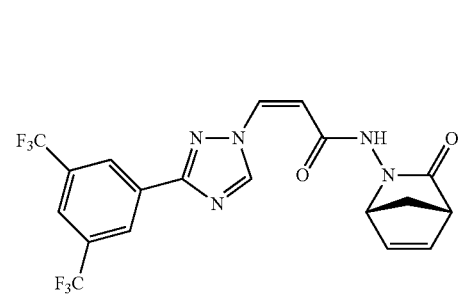

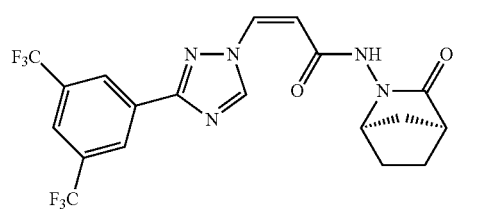
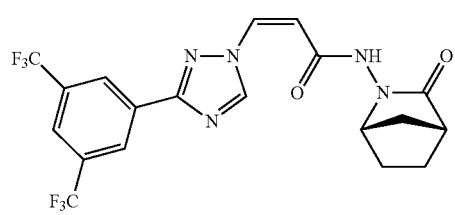
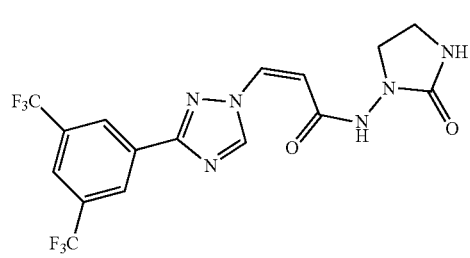
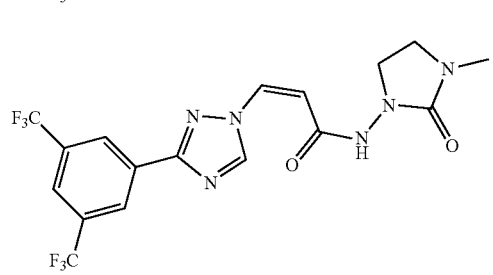
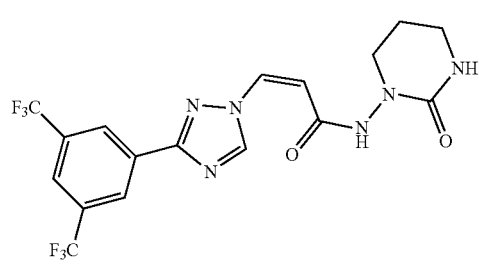
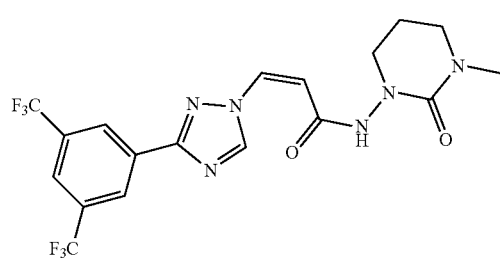
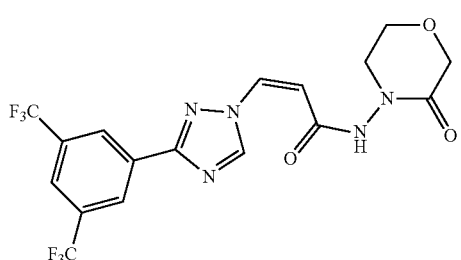
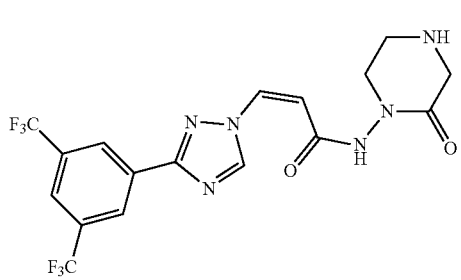
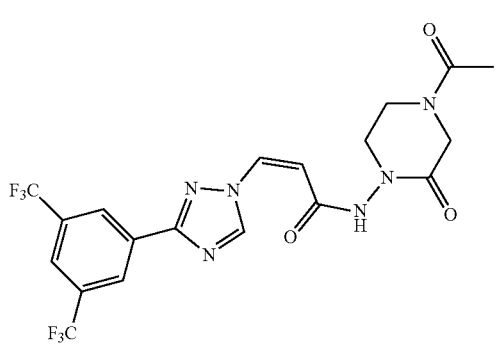
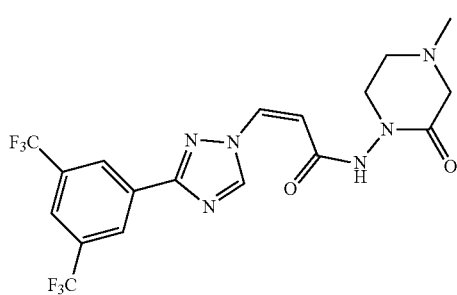
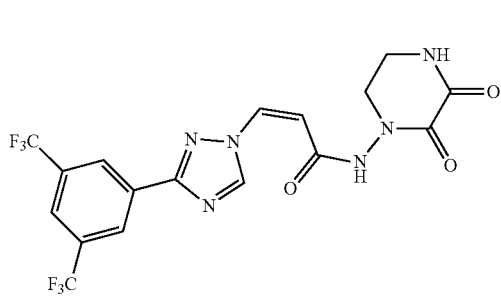

43
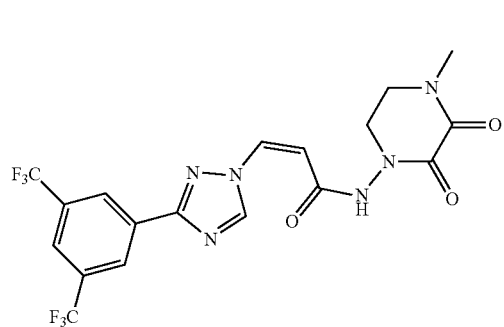
44
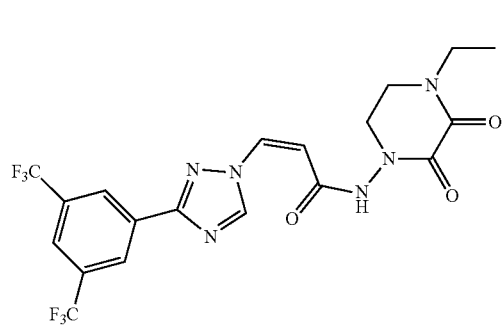
45
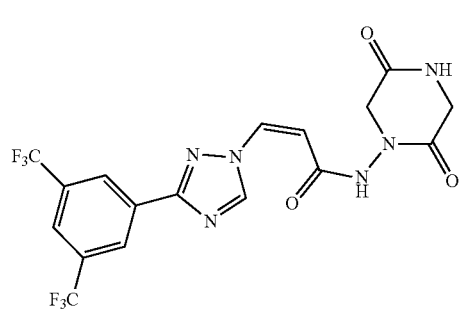
46
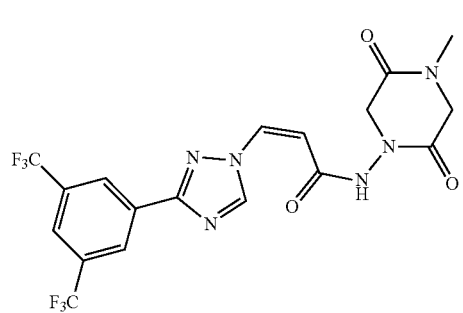
47
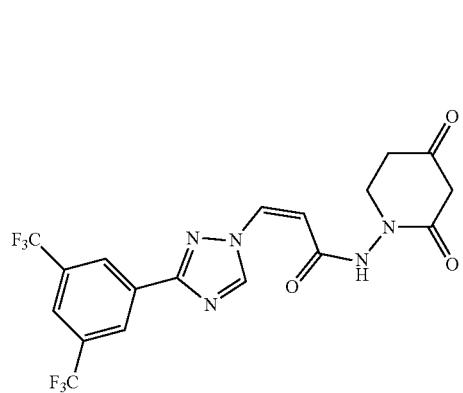
48
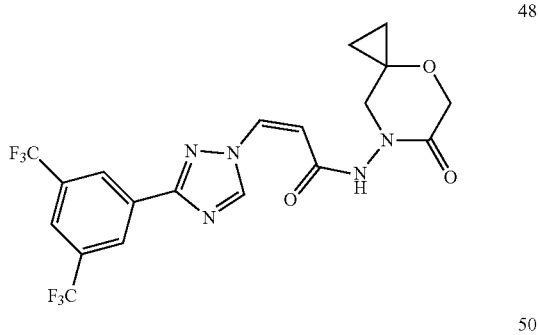
50
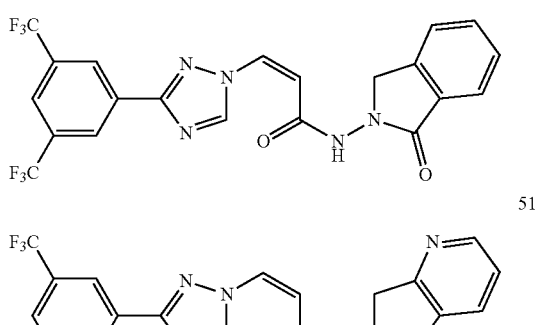
51
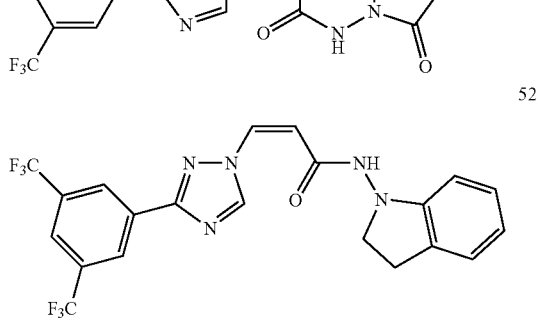
52
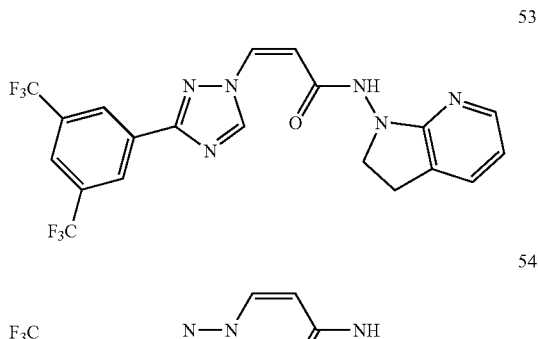
53
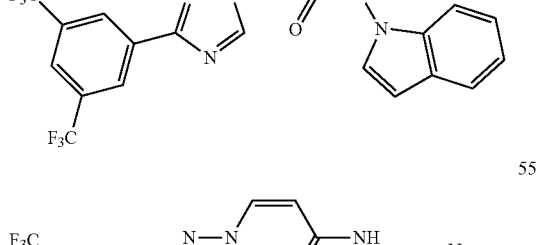
54
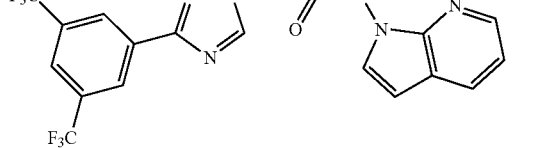
55
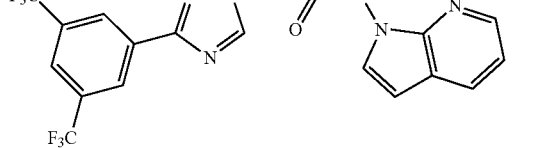

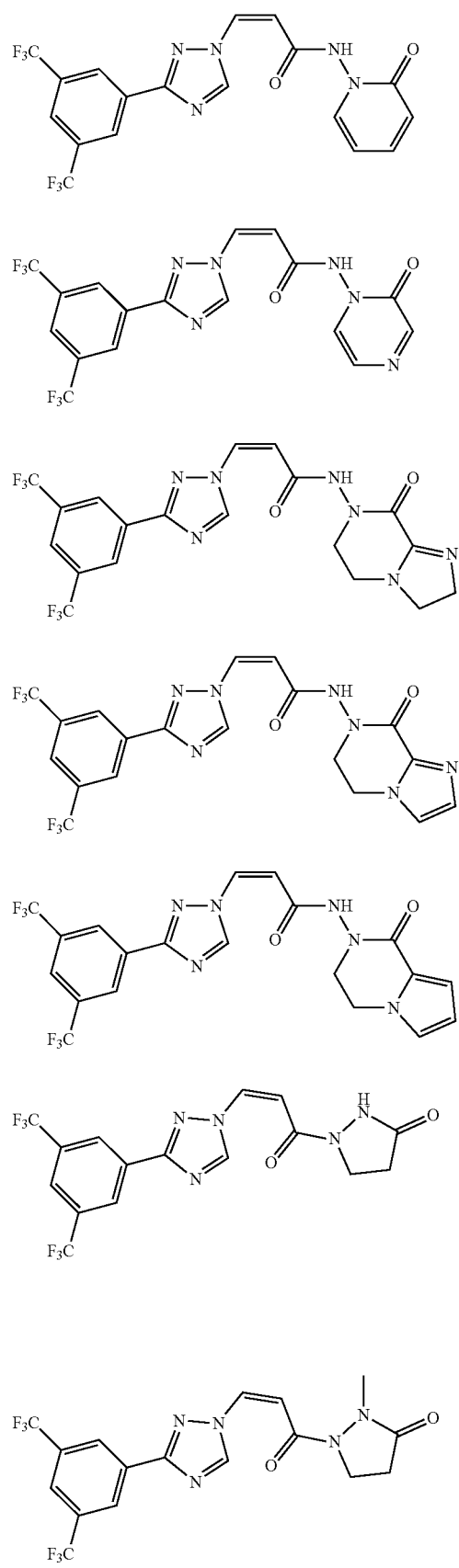
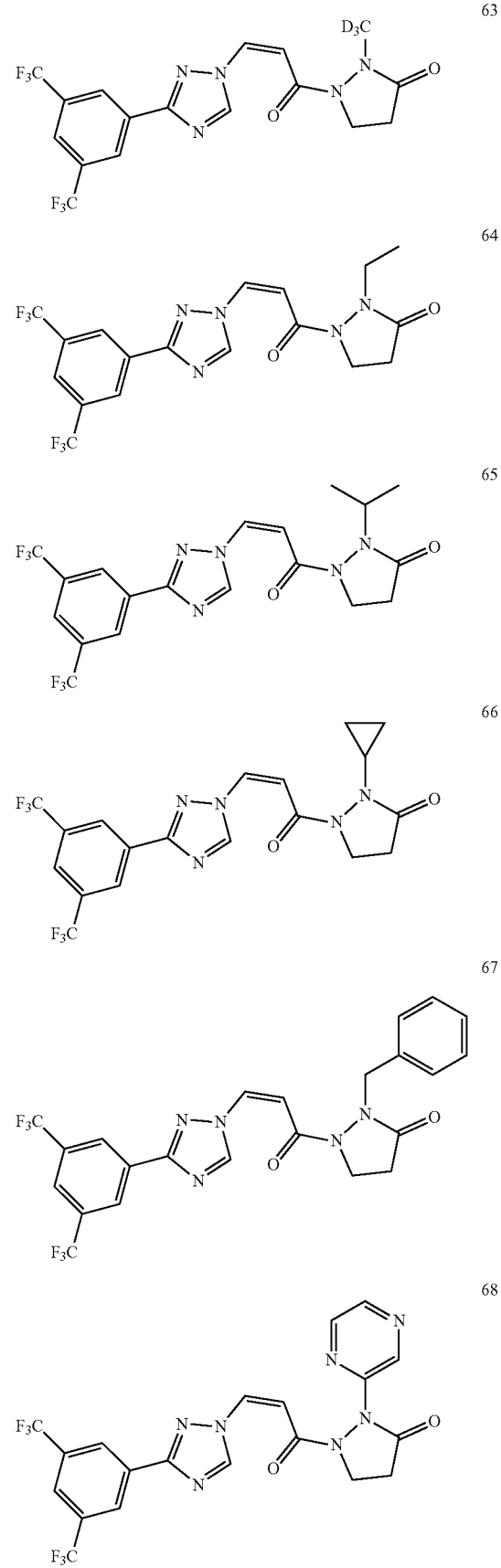

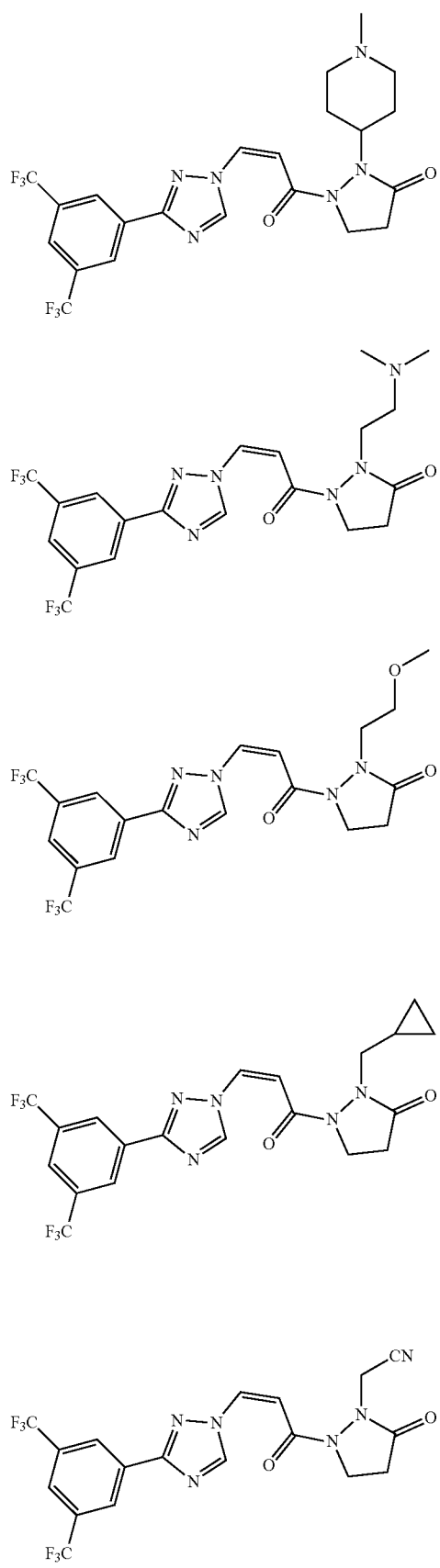
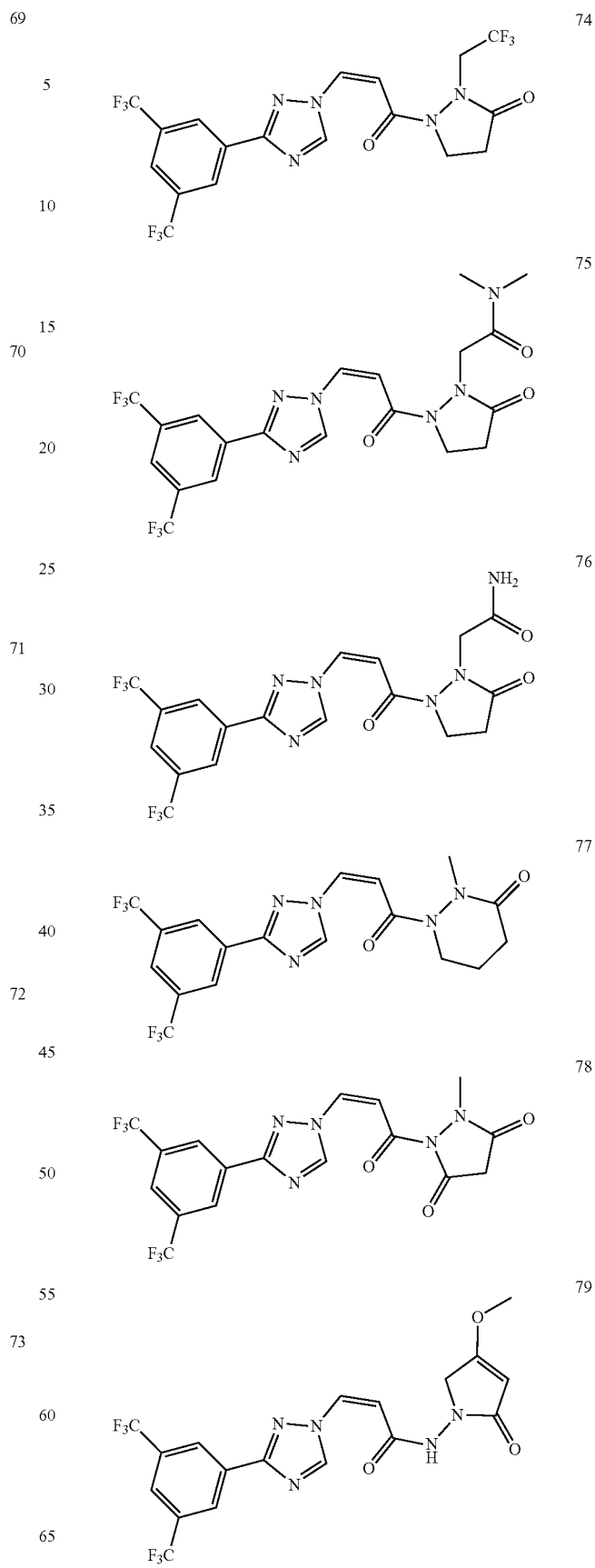

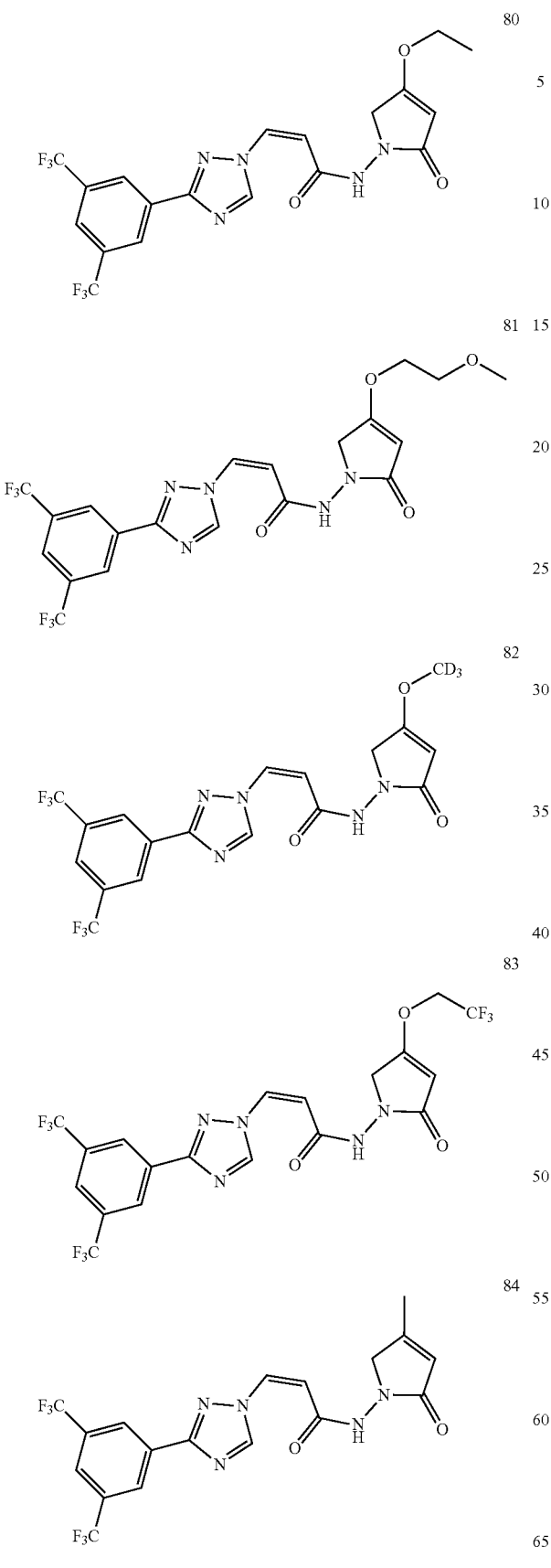
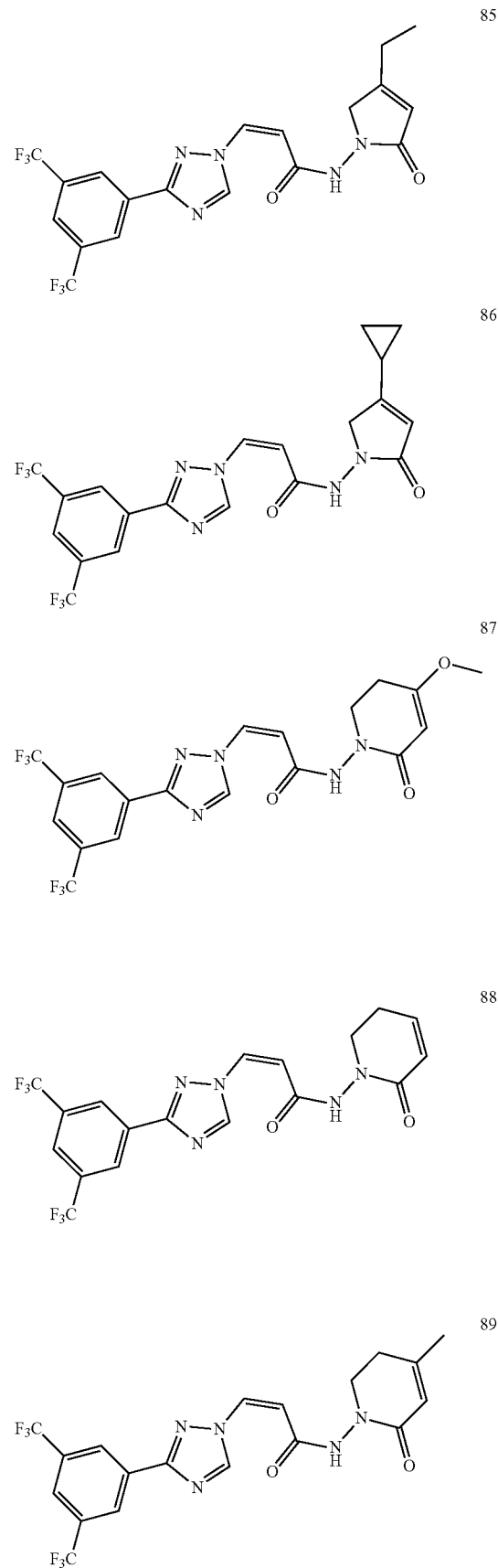

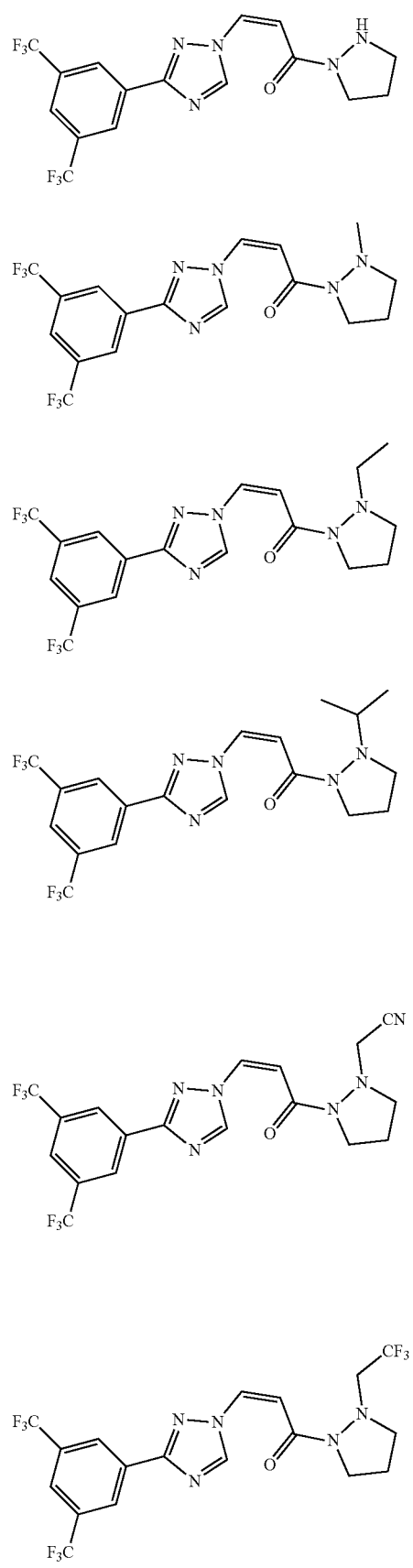
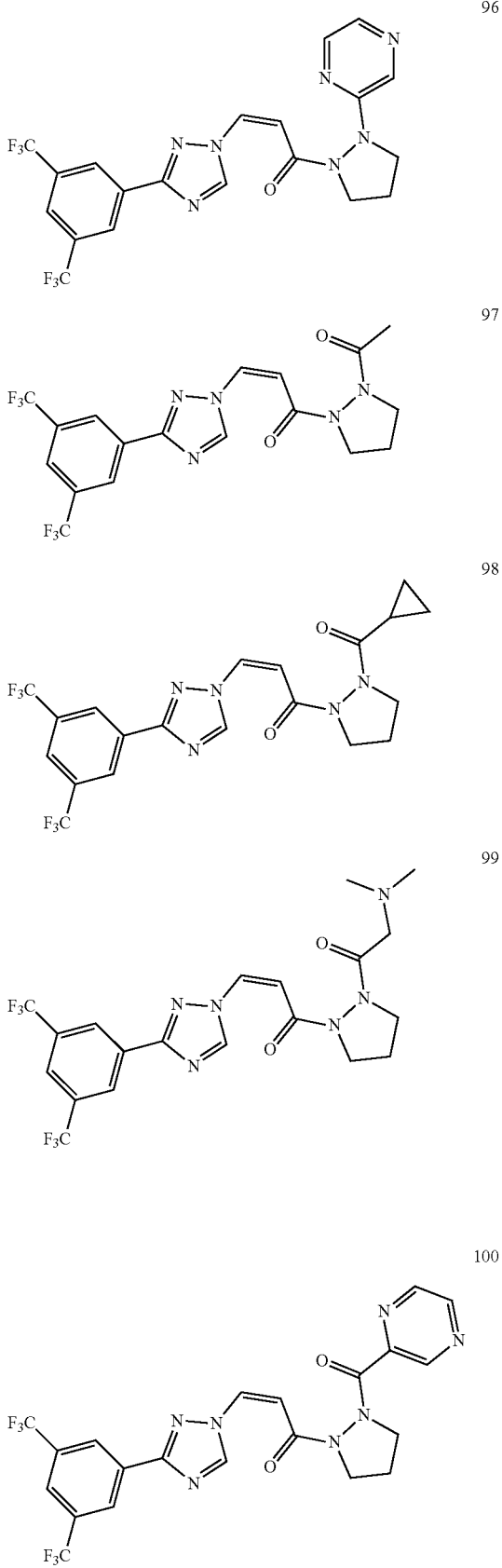

-continued

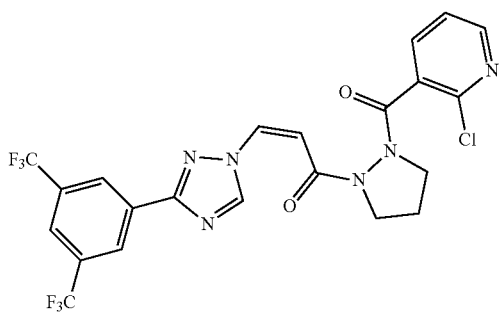

101

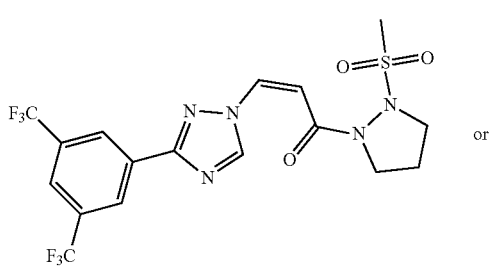

102

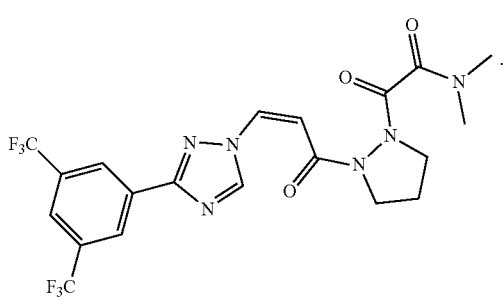

103 or

10. The compound according to claim 1, or a pharmaceutically acceptable salt thereof, wherein the pharmaceutically acceptable salt comprises a salt formed by the compound represented by the general formula (1) and an acid, the acid is an inorganic acid, an organic acid, or an acidic amino acid; the inorganic acid is selected from the group consisting of hydrochloric acid, hydrobromic acid, hydrofluoric acid, sulfuric acid, nitric acid and phosphoric acid; the organic acid is selected from the group consisting of formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, p-toluenesulfonic acid, ethanesulfonic acid and benzenesulfonic acid, and the acidic amino acid is selected from the group consisting of aspartic acid and glutamic acid.

11. A compound of the following formula, an optical isomer, a crystalline form, a pharmaceutically acceptable salt, a hydrate or a solvate thereof:

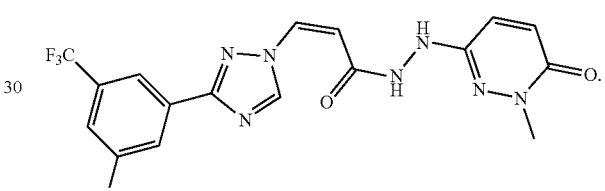

49

\* \* \* \* \*